(12) United States Patent
Ill et al.

(10) Patent No.: US 6,642,028 B1
(45) Date of Patent: Nov. 4, 2003

(54) VECTORS AND GENES EXHIBITING INCREASED EXPRESSION

(75) Inventors: Charles R. Ill, Encinitas, CA (US); Jose E. N. Gonzales, San Diego, CA (US); Claire Q. Yang, Carlsbad, CA (US); Scott Bidlingmaier, New Haven, CT (US)

(73) Assignee: The Immune Response Corporation, Carlsbad, CA (US)

( * ) Notice: Subject to any disclaimer, the term of this patent is extended or adjusted under 35 U.S.C. 154(b) by 0 days.

(21) Appl. No.: 09/205,817

(22) Filed: Dec. 4, 1998

Related U.S. Application Data

(63) Continuation of application No. PCT/US98/25354, filed on Nov. 25, 1998.
(60) Provisional application No. 60/071,596, filed on Jan. 16, 1998, and provisional application No. 60/067,614, filed on Dec. 5, 1997.

(51) Int. Cl.$^7$ .......................... C12P 21/00; C12N 15/00; C12N 15/09; C12N 15/10

(52) U.S. Cl. .................. 435/69.6; 435/69.1; 435/320.1; 435/212; 514/44

(58) Field of Search ............................. 435/69.1, 69.6, 435/320.1, 212; 514/44

(56) References Cited

U.S. PATENT DOCUMENTS

| | | | |
|---|---|---|---|
| 4,657,894 A | 4/1987 | Zimmerman et al. | 514/21 |
| 4,757,006 A | 7/1988 | Toole et al. | 435/70 |
| 4,868,112 A | 9/1989 | Toole et al. | 435/68 |
| 4,886,876 A | 12/1989 | Zimmerman et al. | 530/383 |
| 5,045,455 A | 9/1991 | Kuo et al. | 435/69.6 |
| 5,108,909 A * | 4/1992 | Haigwood | 435/69.2 |
| 5,171,844 A | 12/1992 | Van Ooyen et al. | 530/383 |
| 5,240,846 A | 8/1993 | Collins et al. | 435/240.1 |
| 5,439,824 A | 8/1995 | Brantly et al. | 435/320.1 |
| 5,618,788 A | 4/1997 | Capon et al. | 514/12 |
| 5,618,789 A | 4/1997 | Capon et al. | 514/12 |
| 5,639,661 A | 6/1997 | Welsh et al. | 435/252.3 |
| 5,683,905 A | 11/1997 | Capon et al. | 435/320.1 |
| 5,693,499 A * | 12/1997 | Yonemura et al. | 435/69.6 |
| 5,824,508 A * | 10/1998 | Spaete et al. | 435/69.3 |

FOREIGN PATENT DOCUMENTS

| | | |
|---|---|---|
| EP | 0 218 712 B1 | 11/1986 |
| EP | 0 227 064 A | 7/1987 |
| GB | 2197 321 A | 5/1988 |
| WO | WO9109122 A | 6/1991 |
| WO | WO9530000 A | 11/1995 |
| WO | WO9733994 | 9/1997 |
| WO | WO9749821 A | 12/1997 |
| WO | WO9800542 A | 1/1998 |

OTHER PUBLICATIONS

Economou et al. Detection of Mutations in the Factor VIII Gene Using Single–Stranded Conformational Polymorphism (SSCP), (1992) Genomics 13: 909–911.*

Kemball–Cook et al. The Factor VIII Mutation Database on the World Wide Web: the haemophilia A mutation search, test and resourse site, (1997) Nucleic Acids Research 25(1): 128–132, abstract only.*

Berget, S. "Exon Recognition in Vertebrate Splicing" *J. Bio Chem.*, vol. 270, No. 6 pp. 2411–2414 (1995).

Brinster, R. et al., "Introns Increase Transcriptional Efficiency in Transgenic Mice" *Proc. Natl. Acad. Sci.*, vol. 85, pp 836–840 (1998).

Connelly, S. et al., "High–Level Tissue–Specific Expression of Functional Human Factor VIII in Mice" *Human Gene Therapy*, vol. 7 pp. 183–195 (1996).

Gitschier, J. et al., "Characterization of the Human Factor VIII gene" *Nature*, vol. 312 (1984).

Robberson, B. et al., "Exon Definition May Facilitate Splice Site Selection in RNAs with Multiple Exons" *Mol. Cel. Biol.*, vol. 10, No. 1, pp. 84–94 (1990).

Toole, J. et al., "A Large Region (≈95 kDa) of Human Factor VIII is Dispensable for In Vitro Procoagulant Activity" *Proc. Natl. Acad. Sci.*, vol. 83, pp. 5939–5942 (1986).

Toole, J. et al., "Molecular Cloning of a cDNA encoding Human Antihaemophilic Factor" *Nature*, vol. 312, p. 342 (1984).

Vehar, G. et al., "Structure of Human Factor VIII", *Nature*, vol. 312, p. 337. (1984).

Wood, W. et al., "Expression of Active Human Factor VIII from Recombinant DNA clones" *Nature*, vol. 312, p. 330 (1984).

Yull, F. et al., "Fixing Human Factor IX (fIX): Corection of a Cryptic RNA Splice Enables the Production of Biologically active fIX in the Mammary Gland of Transgenic Mice" *Proc. Natl. Acad. Sci.*, vol. 92, pp. 10899–10903 (1995).

(List continued on next page.)

*Primary Examiner*—Christopher S. F. Low
*Assistant Examiner*—Holly Schnizer
(74) *Attorney, Agent, or Firm*—Lahive & Cockfield, LLP; Jane E. Remillard, Esq.

(57) ABSTRACT

Novel genes and vectors exhibiting increased expression and novel splicing patterns are disclosed. The gene can comprise one or more consensus or near consensus splice sites which have been corrected. The gene can alternatively or additionally comprise one or more introns within coding or noncoding sequences. The gene can still further comprise modified 5' and/or 3' untranslated regions optimized to provide high levels and duration of tissue-specific expression. In one embodiment, the gene comprises the coding region of a full-length Factor VIII gene modified by adding an intron within the portion of the gene encoding the β-domain, so that the gene is expressed as a β-domain deleted Factor VIII protein. The novel Factor VIII gene can also be modified to correct one or more consensus or near consensus splice sites within or outside of the coding region.

17 Claims, 41 Drawing Sheets

OTHER PUBLICATIONS

Aebi, M. et al. (1987) "5' cleavage site in eucaryotic pre–mRNA splicing is determined by the overall 5' splice region, not by the conserved 5' GU" *Cell*, 50: 237–246.

Chapman, B.S. et al. (1991) "Effect of intron A from human cytomegalovirus (Towne) immediate–early gene on heterologous expression in mammalian cells," *Nucl. Acids Res.*, 19(14): 3979–3986.

DelGatto, F. and Breathnach, R. (1995) "Exon and Intron sequences, respectively, repress and activate splicing of a fibroblast growth factor receptor 2 alternative exon," *J. Mol. Biol.*, 15(9): 4825–4834.

Dobkin, C. and Bank, A. (1985) "reversibilityof IVS 2 missplicing in a mutant human beta–globin gene," *J. Biol. Chem.*, 260(30): 16332–16337.

III, C. R. et al. (1997) Optimization of the human factor VIII complementary DNA expression plasmid for gene therapy of hemophilia A, *Blood Coag. Fibrinol.*, 8(S2): S23–S30.

III, C.R. et al. (1997) "Engineering the human factor VIII Cdna for targeted gene therapy," in Thrombosis and Hemostatis, ISSN:0340–6245, Shattauer: Stuttgart; Abstract.

Kaufman, R.J., et al. (1989) "Effect of von willebrand factor coexpression on the synthesis and secretion of factor VIII in Chinese hamster ovary cells," *Mol. Cell. Biol.*, 9(3): 1233–1242.

Kaufman, R.J., et al. (1991) "Improved vectors for stable expression of foreign genes in mammalian cells by use of the untranslated leader sequence from EMC virus," *Nucl. Acids Res.*, 19(16): 4485–4490.

Petitclerc, D., et al. (1995) "The effect of various introns and transcription terminators on the efficiency of expression vectors in various cultured cell lines and in the mammary gland of transgenic mice," *J. Biotech.*, 40(3): 169–178.

Weber, S. and Aebi, M. (1988) "In vitro splicing of Mrna precursors: 5' cleavage site can be predicted from the interaction between the 5' splice region and the 5' terminus of U1 snRNA," *Nucl. Acids Res.*, 16(2): 471–486.

Zhuang et al. (1987) "The natural 5' splice site of simian virus 40 large T antigen can be improved by increasing the base complementarity to U1 RNA," *Mol. Cell. Biol.*, 7(8): 3018–3020.

* cited by examiner

Anatomy of an Intron

5' Splice Site      Branch     3' Splice Site
(Splice Donor)                    (Splice Acceptor)

M = C or A
R = puRine (A or G)
Y = pYrimidine (C or T or U)

Conservative Mutagenesis of
Near Consensus 3' Splice sequence

Conserved Splice
Acceptor sequence

TTC TC[A G]GA GAA
Phe Ser Gly Glu

| Alternate Codons | |
|---|---|
| Ser | Gly |
| TCC<br>TCG<br>TCT | None |

*Fig. 2*

NC-Splice Donor Changes:

| Location in Bayer BDD-Factor VIII cDNA | Nucleotide Change | Codon | Amino Acid |
|---|---|---|---|
| 123 | T → A | GGA | G |
| 474 | G  A | CAA | Q |
| 552 | T  C | GTT | V |
| 778 | T  A | AGC | S |
| 779 | C  G | AGC | S |
| 780 | T  C | AGC | S |
| 789 | T  A | GGA | G |
| 828 | G  T | GTT | V |
| 831 | T  A | ATA | I |
| 876 | T  A | GGA | G |
| 891 | G  T | GTT | V |
| 894 | G  A | AGA | R |
| 1134 | G  A | AGA | R |
| 1317 | T  A | GGA | G |
| 1539 | T  A | GGA | G |
| 1956 | G  A | GAA | E |
| 1959 | G  A | GTA | V |
| 2115 | T  A | GGA | G |
| 2178 | G  A | AAA | K |
| 2184 | T  C | TCC | S |
| 2205 | T  A | GGA | G |
| 2694 | A  T | GTT | V |
| 2697 | T  C | ACC | T |
| 3318 | T  A | GGA | G |
| 3324 | T  C | TTC | F |
| 3591 | G  A | AAA | K |
| 3594 | G  T | GTT | V |
| 3597 | T  C | GAC | D |
| 4041 | G  A | CAA | Q |
| 4044 | G  T | GTT | V |
| 4047 | T  C | AAC | N |
| 4137 | C  T | TCT | S |
| 4143 | T  C | TAC | Y |
| 4218 | G  A | AAA | K |
| 4224 | T  C | TTC | F |
| 4254 | G  C | GTC | V |

*Fig. 4A*

NC-Splice Acceptor Changes

| Location in Bayer BDD-Factor VIII cDNA | Nucleotide change | | Codon | Amino Acid |
|---|---|---|---|---|
| 154 | A | → C | CGC | R |
| 156 | A | C | CGC | R |
| 288 | G | A | CAA | Q |
| 346 | A | T | TCC | S |
| 347 | G | C | TCC | S |
| 348 | T | C | TCC | S |
| 711 | G | A | CAA | Q |
| 1522 | A | C | CGC | R |
| 1524 | G | C | CGC | R |
| 1572 | A | C | CCC | P |
| 1851 | A | C | CCC | P |
| 2079 | A | C | TCC | S |
| 2343 | G | A | CAA | Q |
| 2574 | T | A | GTA | V |
| 2577 | T | A | GTA | V |
| 2610 | G | A | CAA | Q |
| 2737 | A | T | TCC | S |
| 2738 | G | C | TCC | S |
| 2742 | T | C | CTC | L |
| 2745 | T | A | ATA | I |
| 2748 | T | A | TCA | S |
| 3250 | A | T | TCC | S |
| 3251 | G | C | TCC | S |
| 3252 | T | C | TCC | S |
| 3315 | A | C | CCC | P |
| 3427 | A | T | TCC | S |
| 3428 | G | C | TCC | S |
| 3675 | G | A | CAA | Q |
| 4005 | T | A | CTA | L |
| 4011 | C | A | CTA | L |
| 4135 | A | T | TCT | S |
| 4136 | G | C | TCC | S |
| 4161 | C | A | ATA | I |
| 4164 | C | G | TCG | S |
| 4165 | A | T | TCG | S |
| 4166 | G | C | TCG | S |
| 4167 | C | G | TCG | S |
| 4168 | A | T | TCG | S |
| 4169 | G | C | TCG | S |
| 4170 | T | G | TCG | S |
| 4203 | G | A | CAA | Q |

*Fig. 4B*

Branch (lariat) sequence changes:

Location in Bayer
BDD-Factor VIII cDNA     Nucleotide change     Codon     Amino Acid

| Location | Nucleotide change | Codon | Amino Acid |
|---|---|---|---|
| 504  | T→C | TCC | S |
| 703  | T  C | CTC | L |
| 705  | G  C | CTC | L |
| 955  | T  C | CTC | L |
| 957  | G  C | CTC | L |
| 1110 | T  C | ACC | T |
| 1441 | T  C | CTC | L |
| 1443 | G  C | CTC | L |
| 1500 | T  C | ACC | T |
| 1668 | T  C | GTC | V |
| 1923 | T  C | TCC | S |
| 2406 | T  C | TCC | S |
| 2592 | T  C | ACC | T |
| 2892 | T  C | TCC | S |
| 2898 | T  C | GTC | V |
| 2955 | T  C | ACC | T |
| 3024 | T  C | TCC | S |
| 3696 | T  C | CTC | L |
| 3742 | T  C | CTC | L |
| 3744 | A  C | CTC | L |
| 3795 | T  C | TTC | F |
| 4281 | G  C | CTC | L |

*Fig. 4C*

```
                      5        10       15       20       25       30       35       40       45
                      *        *        *        *        *        *        *        *        *
pDJCcoding    ATG GAA ATA GAG CTC TCC ACC TGC TTC TTT CTG TGC CTT TTG CGA TTC
                  |                 |                 |                 |
1. p25Dcod        10                20                30                40
[ 16902 ]     ATG GAA ATA GAG CTC TCC ACC TGC TTC TTT CTG TGC CTT TTG CGA TTC>
              ^^^ ^^^ ^^^ ^^^ ^^^ ^^^ ^^^ ^^^ ^^^ ^^^ ^^^ ^^^ ^^^ ^^^ ^^^ ^^^
pDJCcoding    ATG GAA ATA GAG CTC TCC ACC TGC TTC TTT CTG TGC CTT TTG CGA TTC 50       55       60       65       70       75       80       85       90       95
                     *        *        *        *        *        *        *        *        *        *
pDJCcoding    TGC TTT AGT GCC ACC AGA AGA TAC TAC CTG GGT GCA GTG GAA CTG TCA
                  |                 |                 |                 |                 |
1. p25Dcod        50                60                70                80                90
[ 16902 ]     TGC TTT AGT GCC ACC AGA AGA TAC TAC CTG GGT GCA GTG GAA CTG TCA>
              ^^^ ^^^ ^^^ ^^^ ^^^ ^^^ ^^^ ^^^ ^^^ ^^^ ^^^ ^^^ ^^^ ^^^ ^^^ ^^^
pDJCcoding    TGC TTT AGT GCC ACC AGA AGA TAC TAC CTG GGT GCA GTG GAA CTG TCA 100      105      110      115      120      125      130      135      140
                  *        *        *        *        *        *        *        *        *
pDJCcoding    TGG GAC TAT ATG CAA AGT GAT CTC GGA GAG CTG CCT GTG GAC GCA AGA
                  |                 |                 |                 |                 |
1. p25Dcod    100                110               120               130               140
[ 16902 ]     TGG GAC TAT ATG CAA AGT GAT CTC GGt GAG CTG CCT GTG GAC GCA AGA>
              ^^^ ^^^ ^^^ ^^^ ^^^ ^^^ ^^^ ^^^ ^^v ^^^ ^^^ ^^^ ^^^ ^^^ ^^^ ^^^
pDJCcoding    TGG GAC TAT ATG CAA AGT GAT CTC GGA GAG CTG CCT GTG GAC GCA AGA 145      150      155      160      165      170      175      180      185      190
              *        *        *        *        *        *        *        *        *        *
pDJCcoding    TTT CCT CCT CGC GTG CCA AAA TCT TTT CCA TTC AAC ACC TCA GTC GTG
                  |                 |                 |                 |                 |
1. p25Dcod        150               160               170               180               190
[ 16902 ]     TTT CCT CCT aGa GTG CCA AAA TCT TTT CCA TTC AAC ACC TCA GTC GTG>
              ^^^ ^^^ ^^^ v^v ^^^ ^^^ ^^^ ^^^ ^^^ ^^^ ^^^ ^^^ ^^^ ^^^ ^^^ ^^^
pDJCcoding    TTT CCT CCT CGC GTG CCA AAA TCT TTT CCA TTC AAC ACC TCA GTC GTG 195      200      205      210.     215      220      225      230      235      240
                  *        *        *        *        *        *        *        *        *        *
pDJCcoding    TAC AAA AAG ACT CTG TTT GTA GAA TTC ACG GTT CAC CTT TTC AAC ATC
                  |                 |                 |                 |                 |
1. p25Dcod        200               210               220               230               240
[ 16902 ]     TAC AAA AAG ACT CTG TTT GTA GAA TTC ACG GTT CAC CTT TTC AAC ATC>
              ^^^ ^^^ ^^^ ^^^ ^^^ ^^^ ^^^ ^^^ ^^^ ^^^ ^^^ ^^^ ^^^ ^^^ ^^^ ^^^
pDJCcoding    TAC AAA AAG ACT CTG TTT GTA GAA TTC ACG GTT CAC CTT TTC AAC ATC 245      250      255      260      265      270      275      280      285
                     *        *        *        *        *        *        *        *        *
pDJCcoding    GCT AAG CCA AGG CCA CCC TGG ATG GGT CTG CTA GGT CCT ACC ATC CAA
                      |                 |                 |                 |
1. p25Dcod            250               260               270               280
[ 16902 ]     GCT AAG CCA AGG CCA CCC TGG ATG GGT CTG CTA GGT CCT ACC ATC CAg>
              ^^^ ^^^ ^^^ ^^^ ^^^ ^^^ ^^^ ^^^ ^^^ ^^^ ^^^ ^^^ ^^^ ^^^ ^^^ ^^v
pDJCcoding    GCT AAG CCA AGG CCA CCC TGG ATG GGT CTG CTA GGT CCT ACC ATC CAA
```

*Fig. 5A*

```
              290       295       300       305       310       315       320       325       330       335
                *         *         *         *         *         *         *         *         *         *
pDJCcoding   GCT GAG GTT TAT GAT ACA GTG GTC ATT ACA CTT AAG AAC ATG GCT TCC
                           |                   |                   |                   |
  1. p25Dco290             300                 310                 320                 330
[ 16902 ]    GCT GAG GTT TAT GAT ACA GTG GTC ATT ACA CTT AAG AAC ATG GCT TCC>
             ^^^ ^^^ ^^^ ^^^ ^^^ ^^^ ^^^ ^^^ ^^^ ^^^ ^^^ ^^^ ^^^ ^^^ ^^^ ^^^
pDJCcoding   GCT GAG GTT TAT GAT ACA GTG GTC ATT ACA CTT AAG AAC ATG GCT TCC 340       345       350       355       360       365       370       375       380
                    *         *         *         *         *         *         *         *         *
pDJCcoding   CAT CCT GTC TCC CTT CAT GCT GTT GGT GTA TCC TAC TGG AAA GCT TCT
                       |                   |                   |                   |
  1. p25Dcod  340                 350                 360                 370                 380
[ 16902 ]    CAT CCT GTC agt CTT CAT GCT GTT GGT GTA TCC TAC TGG AAA GCT TCT>
             ^^^ ^^^ ^^^ vvv ^^^ ^^^ ^^^ ^^^ ^^^ ^^^ ^^^ ^^^ ^^^ ^^^ ^^^ ^^^
pDJCcoding   CAT CCT GTC TCC CTT CAT GCT GTT GGT GTA TCC TAC TGG AAA GCT TCT 385       390       395       400       405       410       415       420       425       430
                *         *         *         *         *         *         *         *         *         *
pDJCcoding   GAG GGA GCT GAA TAT GAT GAT CAG ACC AGT CAA AGG GAG AAA GAA GAT
                           |                   |                   |                   |
  1. p25Dcod             390                 400                 410                 420                 430
[ 16902 ]    GAG GGA GCT GAA TAT GAT GAT CAG ACC AGT CAA AGG GAG AAA GAA GAT>
             ^^^ ^^^ ^^^ ^^^ ^^^ ^^^ ^^^ ^^^ ^^^ ^^^ ^^^ ^^^ ^^^ ^^^ ^^^ ^^^
pDJCcoding   GAG GGA GCT GAA TAT GAT GAT CAG ACC AGT CAA AGG GAG AAA GAA GAT 435       440       445       450       455       460       465       470       475       480
                    *         *         *         *         *         *         *         *         *         *
pDJCcoding   GAT AAA GTC TTC CCT GGT GGA AGC CAT ACA TAT GTC TGG CAA GTC CTG
                       |                   |                   |                   |                   |
  1. p25Dcod          440                 450                 460                 470                 480
[ 16902 ]    GAT AAA GTC TTC CCT GGT GGA AGC CAT ACA TAT GTC TGG CAg GTC CTG>
             ^^^ ^^^ ^^^ ^^^ ^^^ ^^^ ^^^ ^^^ ^^^ ^^^ ^^^ ^^^ ^^^ ^^v ^^^ ^^^
pDJCcoding   GAT AAA GTC TTC CCT GGT GGA AGC CAT ACA TAT GTC TGG CAA GTC CTG 485       490       495       500       505       510       515       520       525
                       *         *         *         *         *         *         *         *         *
pDJCcoding   AAA GAG AAT GGT CCA ATG GCC TCC GAC CCA CTG TGC CTT ACC TAC TCA
                           |                   |                   |                   |
  1. p25Dcod              490                 500                 510                 520
[ 16902 ]    AAA GAG AAT GGT CCA ATG GCC TCt GAC CCA CTG TGC CTT ACC TAC TCA>
             ^^^ ^^^ ^^^ ^^^ ^^^ ^^^ ^^^ ^^v ^^^ ^^^ ^^^ ^^^ ^^^ ^^^ ^^^ ^^^
pDJCcoding   AAA GAG AAT GGT CCA ATG GCC TCC GAC CCA CTG TGC CTT ACC TAC TCA 530       535       540       545       550       555       560       565       570       575
                  *         *         *         *         *         *         *         *         *         *
pDJCcoding   TAT CTT TCT CAT GTG GAC CTG GTT AAA GAC TTG AAT TCA GGC CTC ATT
                       |                   |                           |                   |
  1. p25Dco530        540                 550                         560                 570
[ 16902 ]    TAT CTT TCT CAT GTG GAC CTG GTa AAA GAC TTG AAT TCA GGC CTC ATT>
             ^^^ ^^^ ^^^ ^^^ ^^^ ^^^ ^^^ ^^v ^^^ ^^^ ^^^ ^^^ ^^^ ^^^ ^^^ ^^^
pDJCcoding   TAT CTT TCT CAT GTG GAC CTG GTT AAA GAC TTG AAT TCA GGC CTC ATT
```

*Fig. 5B*

```
                580     585     590     595     600     605     610     615     620
                 *       *       *       *       *       *       *       *       *
pDJCcoding      GGA GCC CTA CTA GTA TGT AGA GAA GGG AGT CTG GCC AAG GAA AAG ACA
                 |               |               |               |               |
  1. p25Dcod   580             590             600             610             620
[ 16902 ]       GGA GCC CTA CTA GTA TGT AGA GAA GGG AGT CTG GCC AAG GAA AAG ACA>
                ^^^ ^^^ ^^^ ^^^ ^^^ ^^^ ^^^ ^^^ ^^^ ^^^ ^^^ ^^^ ^^^ ^^^ ^^^ ^^^
pDJCcoding      GGA GCC CTA CTA GTA TGT AGA GAA GGG AGT CTG GCC AAG GAA AAG ACA 625     630     635     640     645     650     655     660     665     670
                 *       *       *       *       *       *       *       *       *       *
pDJCcoding      CAG ACC TTG CAC AAA TTT ATA CTA CTT TTT GCT GTA TTT GAT GAA GGG
                 |               |               |               |               |
  1. p25Dcod   630             640             650             660             670
[ 16902 ]       CAG ACC TTG CAC AAA TTT ATA CTA CTT TTT GCT GTA TTT GAT GAA GGG>
                ^^^ ^^^ ^^^ ^^^ ^^^ ^^^ ^^^ ^^^ ^^^ ^^^ ^^^ ^^^ ^^^ ^^^ ^^^ ^^^
pDJCcoding      CAG ACC TTG CAC AAA TTT ATA CTA CTT TTT GCT GTA TTT GAT GAA GGG 675     680     685     690     695     700     705     710     715     720
                 *       *       *       *       *       *       *       *       *       *
pDJCcoding      AAA AGT TGG CAC TCA GAA ACA AAG AAC TCC CTC ATG CAA GAT AGG GAT
                 |               |               |               |               |
  1. p25Dcod   680             690             700             710             720
[ 16902 ]       AAA AGT TGG CAC TCA GAA ACA AAG AAC TCC tTg ATG CAg GAT AGG GAT>
                ^^^ ^^^ ^^^ ^^^ ^^^ ^^^ ^^^ ^^^ ^^^ ^^^ v^v ^^^ ^^v ^^^ ^^^ ^^^
pDJCcoding      AAA AGT TGG CAC TCA GAA ACA AAG AAC TCC CTC ATG CAA GAT AGG GAT 725     730     735     740     745     750     755     760     765
                 *       *       *       *       *       *       *       *       *
pDJCcoding      GCT GCA TCT GCT CGG GCC TGG CCT AAA ATG CAC ACA GTC AAT GGT TAT
                 |               |               |               |               
  1. p25Dcod   730             740             750             760
[ 16902 ]       GCT GCA TCT GCT CGG GCC TGG CCT AAA ATG CAC ACA GTC AAT GGT TAT>
                ^^^ ^^^ ^^^ ^^^ ^^^ ^^^ ^^^ ^^^ ^^^ ^^^ ^^^ ^^^ ^^^ ^^^ ^^^ ^^^
pDJCcoding      GCT GCA TCT GCT CGG GCC TGG CCT AAA ATG CAC ACA GTC AAT GGT TAT 770     775     780     785     790     795     800     805     810     815
                 *       *       *       *       *       *       *       *       *       *
pDJCcoding      GTA AAC AGG AGC CTG CCA GGA CTG ATT GGA TGC CAC AGG AAA TCA GTC
                 |               |               |               |               |
  1. p25Dco770                 780             790             800             810
[ 16902 ]       GTA AAC AGG tct CTG CCA GGt CTG ATT GGA TGC CAC AGG AAA TCA GTC>
                ^^^ ^^^ ^^^ vvv ^^^ ^^^ ^^v ^^^ ^^^ ^^^ ^^^ ^^^ ^^^ ^^^ ^^^ ^^^
pDJCcoding      GTA AAC AGG AGC CTG CCA GGA CTG ATT GGA TGC CAC AGG AAA TCA GTC 820     825     830     835     840     845     850     855     860
                 *       *       *       *       *       *       *       *       *
pDJCcoding      TAT TGG CAT GTT ATA GGA ATG GGC ACC ACT CCT GAA GTG CAC TCA ATA
                 |               |               |               |               |
  1. p25Dcod   820             830             840             850             860
[ 16902 ]       TAT TGG CAT GTg ATt GGA ATG GGC ACC ACT CCT GAA GTG CAC TCA ATA>
                ^^^ ^^^ ^^^ ^^v ^^v ^^^ ^^^ ^^^ ^^^ ^^^ ^^^ ^^^ ^^^ ^^^ ^^^ ^^^
pDJCcoding      TAT TGG CAT GTT ATA GGA ATG GGC ACC ACT CCT GAA GTG CAC TCA ATA
```

*Fig. 5C*

```
              865       870       875       880       885       890       895       900       905       910
               *         *         *         *         *         *         *         *         *         *
pDJCcoding   TTC  CTC  GAA  GGA  CAC  ACA  TTT  CTT  GTT  AGA  AAC  CAT  CGC  CAG  GCG  TCC
              |                        |                        |                        |              |
1. p25Dcod    870                      880                      890                      900            910
[ 16902 ]    TTC  CTC  GAA  GGt  CAC  ACA  TTT  CTT  GTg  AGg  AAC  CAT  CGC  CAG  GCG  TCC>
             ^^^  ^^^  ^^^  ^^v  ^^^  ^^^  ^^^  ^^^  ^^v  ^^v  ^^^  ^^^  ^^^  ^^^  ^^^  ^^^
pDJCcoding   TTC  CTC  GAA  GGA  CAC  ACA  TTT  CTT  GTT  AGA  AAC  CAT  CGC  CAG  GCG  TCC 915       920       925       930       935       940       945       950       955       960
                    *         *         *         *         *         *         *         *         *         *
pDJCcoding        TTG  GAA  ATC  TCG  CCA  ATA  ACT  TTC  CTT  ACT  GCT  CAA  ACA  CTC  CTC  ATG
                   |                        |                        |                        |              |
1. p25Dcod         920                      930                      940                      950            960
[ 16902 ]         TTG  GAA  ATC  TCG  CCA  ATA  ACT  TTC  CTT  ACT  GCT  CAA  ACA  CTC  tTg  ATG>
                  ^^^  ^^^  ^^^  ^^^  ^^^  ^^^  ^^^  ^^^  ^^^  ^^^  ^^^  ^^^  ^^^  ^^^  v^v  ^^^
pDJCcoding        TTG  GAA  ATC  TCG  CCA  ATA  ACT  TTC  CTT  ACT  GCT  CAA  ACA  CTC  CTC  ATG 965       970       975       980       985       990       995      1000      1005
                         *         *         *         *         *         *         *         *         *
pDJCcoding             GAC  CTT  GGA  CAG  TTT  CTA  CTG  TTT  TGT  CAT  ATC  TCT  TCC  CAC  CAA  CAT
                        |                        |                        |                        |
1. p25Dcod              970                      980                      990                     1000
[ 16902 ]              GAC  CTT  GGA  CAG  TTT  CTA  CTG  TTT  TGT  CAT  ATC  TCT  TCC  CAC  CAA  CAT>
                       ^^^  ^^^  ^^^  ^^^  ^^^  ^^^  ^^^  ^^^  ^^^  ^^^  ^^^  ^^^  ^^^  ^^^  ^^^  ^^^
pDJCcoding             GAC  CTT  GGA  CAG  TTT  CTA  CTG  TTT  TGT  CAT  ATC  TCT  TCC  CAC  CAA  CAT 1010      1015      1020      1025      1030      1035      1040      1045 1050      1055
                    *         *         *         *         *         *         *         *    *         *
pDJCcoding        GAT  GGC  ATG  GAA  GCT  TAT  GTC  AAA  GTA  GAC  AGC  TGT  CCA  GAG  GAA  CCC
                   |                        |                        |                        |
1. p25Dc1010                                1020                     1030                     1040           1050
[ 16902 ]         GAT  GGC  ATG  GAA  GCT  TAT  GTC  AAA  GTA  GAC  AGC  TGT  CCA  GAG  GAA  CCC>
                  ^^^  ^^^  ^^^  ^^^  ^^^  ^^^  ^^^  ^^^  ^^^  ^^^  ^^^  ^^^  ^^^  ^^^  ^^^  ^^^
pDJCcoding        GAT  GGC  ATG  GAA  GCT  TAT  GTC  AAA  GTA  GAC  AGC  TGT  CCA  GAG  GAA  CCC 1060 1065      1070      1075      1080      1085      1090 1095      1100
                    *    *         *         *         *         *         *    *         *
pDJCcoding        CAA  CTA  CGA  ATG  AAA  AAT  AAT  GAA  GAA  GCG  GAA  GAC  TAT  GAT  GAT  GAT
                   |                        |                        |                        |
1. p25Dcod 1060                             1070                     1080                     1090           1100
[ 16902 ]         CAA  CTA  CGA  ATG  AAA  AAT  AAT  GAA  GAA  GCG  GAA  GAC  TAT  GAT  GAT  GAT>
                  ^^^  ^^^  ^^^  ^^^  ^^^  ^^^  ^^^  ^^^  ^^^  ^^^  ^^^  ^^^  ^^^  ^^^  ^^^  ^^^
pDJCcoding        CAA  CTA  CGA  ATG  AAA  AAT  AAT  GAA  GAA  GCG  GAA  GAC  TAT  GAT  GAT  GAT 1105 1110      1115      1120      1125      1130      1135 1140      1145      1150
                    *    *         *         *         *         *         *    *         *         *
pDJCcoding        CTT  ACC  GAT  TCT  GAA  ATG  GAT  GTG  GTC  AGA  TTT  GAT  GAT  GAC  AAC  TCT
                   |                        |                        |                        |              |
1. p25Dcod         1110                     1120                     1130                     1140           1150
[ 16902 ]         CTT  ACt  GAT  TCT  GAA  ATG  GAT  GTG  GTC  AGg  TTT  GAT  GAT  GAC  AAC  TCT>
                  ^^^  ^^v  ^^^  ^^^  ^^^  ^^^  ^^^  ^^^  ^^^  ^^v  ^^^  ^^^  ^^^  ^^^  ^^^  ^^^
pDJCcoding        CTT  ACC  GAT  TCT  GAA  ATG  GAT  GTG  GTC  AGA  TTT  GAT  GAT  GAC  AAC  TCT
```

*Fig. 5D*

```
              1155   1160   1165   1170   1175   1180   1185   1190   1195   1200
                *      *      *      *      *      *      *      *      *      *
pDJCcoding    CCT   TCC   TTT   ATC   CAA   ATT   CGC   TCA   GTT   GCC   AAG   AAG   CAT   CCT   AAA   ACT
               |                  |                  |                  |                  |
1. p25Dcod          1160                 1170                 1180                 1190                 1200
[ 16902 ]     CCT   TCC   TTT   ATC   CAA   ATT   CGC   TCA   GTT   GCC   AAG   AAG   CAT   CCT   AAA   ACT>
              ^^^   ^^^   ^^^   ^^^   ^^^   ^^^   ^^^   ^^^   ^^^   ^^^   ^^^   ^^^   ^^^   ^^^   ^^^   ^^^
pDJCcoding    CCT   TCC   TTT   ATC   CAA   ATT   CGC   TCA   GTT   GCC   AAG   AAG   CAT   CCT   AAA   ACT 1205   1210   1215   1220   1225   1230   1235   1240   1245
                    *      *      *      *      *      *      *      *      *
pDJCcoding        TGG   GTA   CAT   TAC   ATT   GCT   GCT   GAA   GAG   GAG   GAC   TGG   GAC   TAT   GCT   CCC
                   |                  |                  |                  |
1. p25Dcod              1210                 1220                 1230                 1240
[ 16902 ]         TGG   GTA   CAT   TAC   ATT   GCT   GCT   GAA   GAG   GAG   GAC   TGG   GAC   TAT   GCT   CCC>
                  ^^^   ^^^   ^^^   ^^^   ^^^   ^^^   ^^^   ^^^   ^^^   ^^^   ^^^   ^^^   ^^^   ^^^   ^^^   ^^^
pDJCcoding        TGG   GTA   CAT   TAC   ATT   GCT   GCT   GAA   GAG   GAG   GAC   TGG   GAC   TAT   GCT   CCC 1250   1255   1260   1265   1270   1275   1280   1285   1290   1295
                   *      *      *      *      *      *      *      *      *      *
pDJCcoding       TTA   GTC   CTC   GCC   CCC   GAT   GAC   AGA   AGT   TAT   AAA   AGT   CAA   TAT   TTG   AAC
                  |                  |                  |                  |                  |
1. p25Dc1250           1260                 1270                 1280                 1290
[ 16902 ]        TTA   GTC   CTC   GCC   CCC   GAT   GAC   AGA   AGT   TAT   AAA   AGT   CAA   TAT   TTG   AAC>
                 ^^^   ^^^   ^^^   ^^^   ^^^   ^^^   ^^^   ^^^   ^^^   ^^^   ^^^   ^^^   ^^^   ^^^   ^^^   ^^^
pDJCcoding       TTA   GTC   CTC   GCC   CCC   GAT   GAC   AGA   AGT   TAT   AAA   AGT   CAA   TAT   TTG   AAC 1300   1305   1310   1315   1320   1325   1330   1335   1340
                *      *      *      *      *      *      *      *      *
pDJCcoding    AAT   GGC   CCT   CAG   CGG   ATT   GGA   AGG   AAG   TAC   AAA   AAA   GTC   CGA   TTT   ATG
               |                  |                  |                  |                  |
1. p25Dcod 1300          1310                 1320                 1330                 1340
[ 16902 ]     AAT   GGC   CCT   CAG   CGG   ATT   GGt   AGG   AAG   TAC   AAA   AAA   GTC   CGA   TTT   ATG>
              ^^^   ^^^   ^^^   ^^^   ^^^   ^^^   ^^v   ^^^   ^^^   ^^^   ^^^   ^^^   ^^^   ^^^   ^^^   ^^^
pDJCcoding    AAT   GGC   CCT   CAG   CGG   ATT   GGA   AGG   AAG   TAC   AAA   AAA   GTC   CGA   TTT   ATG 1345   1350   1355   1360   1365   1370   1375   1380   1385   1390
                    *      *      *      *      *      *      *      *      *      *
pDJCcoding        GCA   TAC   ACA   GAT   GAA   ACC   TTT   AAG   ACT   CGT   GAA   GCT   ATT   CAG   CAT   GAA
                   |                  |                  |                  |                  |
1. p25Dcod              1350                 1360                 1370                 1380                 1390
[ 16902 ]         GCA   TAC   ACA   GAT   GAA   ACC   TTT   AAG   ACT   CGT   GAA   GCT   ATT   CAG   CAT   GAA>
                  ^^^   ^^^   ^^^   ^^^   ^^^   ^^^   ^^^   ^^^   ^^^   ^^^   ^^^   ^^^   ^^^   ^^^   ^^^   ^^^
pDJCcoding        GCA   TAC   ACA   GAT   GAA   ACC   TTT   AAG   ACT   CGT   GAA   GCT   ATT   CAG   CAT   GAA 1395   1400   1405   1410   1415   1420   1425   1430   1435   1440
                *      *      *      *      *      *      *      *      *      *
pDJCcoding    TCA   GGA   ATC   TTG   GGA   CCT   TTA   CTT   TAT   GGG   GAA   GTT   GGA   GAC   ACA   CTG
               |                  |                  |                  |                  |
1. p25Dcod          1400                 1410                 1420                 1430                 1440
[ 16902 ]     TCA   GGA   ATC   TTG   GGA   CCT   TTA   CTT   TAT   GGG   GAA   GTT   GGA   GAC   ACA   CTG>
              ^^^   ^^^   ^^^   ^^^   ^^^   ^^^   ^^^   ^^^   ^^^   ^^^   ^^^   ^^^   ^^^   ^^^   ^^^   ^^^
pDJCcoding    TCA   GGA   ATC   TTG   GGA   CCT   TTA   CTT   TAT   GGG   GAA   GTT   GGA   GAC   ACA   CTG
```

*Fig. 5E*

```
                   1445     1450    1455    1460    1465    1470    1475    1480    1485
                    *        *       *       *       *       *       *       *       *
pDJCcoding    CTC  ATT  ATA  TTT  AAG  AAT  CAA  GCA  AGC  AGA  CCA  TAT  AAC  ATC  TAC  CCT
                    |              |              |              |              |
 1. p25Dcod        1450           1460           1470           1480
 [ 16902 ]    tTg  ATT  ATA  TTT  AAG  AAT  CAA  GCA  AGC  AGA  CCA  TAT  AAC  ATC  TAC  CCT>
              v^v  ^^^  ^^^  ^^^  ^^^  ^^^  ^^^  ^^^  ^^^  ^^^  ^^^  ^^^  ^^^  ^^^  ^^^  ^^^
pDJCcoding    CTC  ATT  ATA  TTT  AAG  AAT  CAA  GCA  AGC  AGA  CCA  TAT  AAC  ATC  TAC  CCT 1490    1495    1500    1505    1510    1515    1520    1525    1530    1535
              *       *       *       *       *       *       *       *       *       *
pDJCcoding   CAC  GGA  ATC  ACC  GAT  GTC  CGT  CCT  TTG  TAT  TCA  CGC  AGA  TTA  CCA  AAA
              |              |              |              |              |
 1. p25Dc1490              1500           1510           1520           1530
 [ 16902 ]   CAC  GGA  ATC  ACt  GAT  GTC  CGT  CCT  TTG  TAT  TCA  aGg  AGA  TTA  CCA  AAA>
             ^^^  ^^^  ^^^  ^^v  ^^^  ^^^  ^^^  ^^^  ^^^  ^^^  ^^^  v^v  ^^^  ^^^  ^^^  ^^^
pDJCcoding   CAC  GGA  ATC  ACC  GAT  GTC  CGT  CCT  TTG  TAT  TCA  CGC  AGA  TTA  CCA  AAA 1540    1545    1550    1555    1560    1565    1570    1575    1580
               *       *       *       *       *       *       *       *       *
pDJCcoding   GGA  GTA  AAA  CAT  TTG  AAG  GAT  TTT  CCA  ATT  CTG  CCC  GGA  GAA  ATA  TTC
               |              |              |              |              |
 1. p25Dcod  1540           1550           1560           1570           1580
 [ 16902 ]   GGt  GTA  AAA  CAT  TTG  AAG  GAT  TTT  CCA  ATT  CTG  CCa  GGA  GAA  ATA  TTC>
             ^^v  ^^^  ^^^  ^^^  ^^^  ^^^  ^^^  ^^^  ^^^  ^^^  ^^^  ^^v  ^^^  ^^^  ^^^  ^^^
pDJCcoding   GGA  GTA  AAA  CAT  TTG  AAG  GAT  TTT  CCA  ATT  CTG  CCC  GGA  GAA  ATA  TTC 1585    1590    1595    1600    1605    1610    1615    1620    1625    1630
              *       *       *       *       *       *       *       *       *       *
pDJCcoding   AAA  TAT  AAA  TGG  ACA  GTG  ACT  GTA  GAA  GAT  GGG  CCA  ACT  AAA  TCA  GAT
              |              |              |              |              |
 1. p25Dcod  1590           1600           1610           1620           1630
 [ 16902 ]   AAA  TAT  AAA  TGG  ACA  GTG  ACT  GTA  GAA  GAT  GGG  CCA  ACT  AAA  TCA  GAT>
             ^^^  ^^^  ^^^  ^^^  ^^^  ^^^  ^^^  ^^^  ^^^  ^^^  ^^^  ^^^  ^^^  ^^^  ^^^  ^^^
pDJCcoding   AAA  TAT  AAA  TGG  ACA  GTG  ACT  GTA  GAA  GAT  GGG  CCA  ACT  AAA  TCA  GAT 1635    1640    1645    1650    1655    1660    1665    1670    1675    1680
              *       *       *       *       *       *       *       *       *       *
pDJCcoding   CCT  CGG  TGC  CTG  ACC  CGC  TAT  TAC  TCT  AGT  TTC  GTC  AAT  ATG  GAG  AGA
              |              |              |              |              |
 1. p25Dcod  1640           1650           1660           1670           1680
 [ 16902 ]   CCT  CGG  TGC  CTG  ACC  CGC  TAT  TAC  TCT  AGT  TTC  GTt  AAT  ATG  GAG  AGA>
             ^^^  ^^^  ^^^  ^^^  ^^^  ^^^  ^^^  ^^^  ^^^  ^^^  ^^^  ^^v  ^^^  ^^^  ^^^  ^^^
pDJCcoding   CCT  CGG  TGC  CTG  ACC  CGC  TAT  TAC  TCT  AGT  TTC  GTC  AAT  ATG  GAG  AGA 1685    1690    1695    1700    1705    1710    1715    1720    1725
              *       *       *       *       *       *       *       *       *
pDJCcoding   GAT  CTA  GCT  TCA  GGA  CTC  ATT  GGC  CCT  CTC  CTC  ATC  TGC  TAC  AAA  GAA
              |              |              |              |              |
 1. p25Dcod              1690           1700           1710           1720
 [ 16902 ]   GAT  CTA  GCT  TCA  GGA  CTC  ATT  GGC  CCT  CTC  CTC  ATC  TGC  TAC  AAA  GAA>
             ^^^  ^^^  ^^^  ^^^  ^^^  ^^^  ^^^  ^^^  ^^^  ^^^  ^^^  ^^^  ^^^  ^^^  ^^^  ^^^
pDJCcoding   GAT  CTA  GCT  TCA  GGA  CTC  ATT  GGC  CCT  CTC  CTC  ATC  TGC  TAC  AAA  GAA
```

*Fig. 5F*

```
                1730   1735   1740   1745   1750   1755   1760   1765   1770   1775
                  *      *      *      *      *      *      *      *      *      *
pDJCcoding      TCT    GTA    GAT    CAA    AGA    GGA    AAC    CAG    ATA    ATG    TCA    GAC    AAG    AGG    AAT    GTC
                 |                    |                    |                    |                    |
  1. p25Dc1730         1740                  1750                 1760                 1770
[ 16902 ]       TCT    GTA    GAT    CAA    AGA    GGA    AAC    CAG    ATA    ATG    TCA    GAC    AAG    AGG    AAT    GTC>
                ^^^    ^^^    ^^^    ^^^    ^^^    ^^^    ^^^    ^^^    ^^^    ^^^    ^^^    ^^^    ^^^    ^^^    ^^^    ^^^
pDJCcoding      TCT    GTA    GAT    CAA    AGA    GGA    AAC    CAG    ATA    ATG    TCA    GAC    AAG    AGG    AAT    GTC 1780   1785   1790   1795   1800   1805   1810   1815   1820
                *      *      *      *      *      *      *      *      *
pDJCcoding    ATC    CTG    TTT    TCT    GTA    TTT    GAT    GAG    AAC    CGA    AGC    TGG    TAC    CTC    ACA    GAG
               |                    |                    |                    |                    |
  1. p25Dcod 1780                  1790                 1800                 1810                 1820
[ 16902 ]     ATC    CTG    TTT    TCT    GTA    TTT    GAT    GAG    AAC    CGA    AGC    TGG    TAC    CTC    ACA    GAG>
              ^^^    ^^^    ^^^    ^^^    ^^^    ^^^    ^^^    ^^^    ^^^    ^^^    ^^^    ^^^    ^^^    ^^^    ^^^    ^^^
pDJCcoding    ATC    CTG    TTT    TCT    GTA    TTT    GAT    GAG    AAC    CGA    AGC    TGG    TAC    CTC    ACA    GAG 1825   1830   1835   1840   1845   1850   1855   1860   1865   1870
            *      *      *      *      *      *      *      *      *      *
pDJCcoding  AAT    ATA    CAA    CGC    TTT    CTC    CCC    AAT    CCC    GCT    GGA    GTG    CAG    CTT    GAG    GAT
             |                    |                    |                    |                    |
  1. p25Dcod  1830                1840                 1850                 1860                 1870
[ 16902 ]   AAT    ATA    CAA    CGC    TTT    CTC    CCC    AAT    CCa    GCT    GGA    GTG    CAG    CTT    GAG    GAT>
            ^^^    ^^^    ^^^    ^^^    ^^^    ^^^    ^^^    ^^^    ^^v    ^^^    ^^^    ^^^    ^^^    ^^^    ^^^    ^^^
pDJCcoding  AAT    ATA    CAA    CGC    TTT    CTC    CCC    AAT    CCC    GCT    GGA    GTG    CAG    CTT    GAG    GAT 1875   1880   1885   1890   1895   1900   1905   1910   1915   1920
              *      *      *      *      *      *      *      *      *      *
pDJCcoding   CCA    GAG    TTC    CAA    GCC    TCC    AAC    ATC    ATG    CAC    AGC    ATC    AAT    GGC    TAT    GTT
              |                    |                    |                    |                    |
  1. p25Dcod 1880                 1890                 1900                 1910                 1920
[ 16902 ]    CCA    GAG    TTC    CAA    GCC    TCC    AAC    ATC    ATG    CAC    AGC    ATC    AAT    GGC    TAT    GTT>
             ^^^    ^^^    ^^^    ^^^    ^^^    ^^^    ^^^    ^^^    ^^^    ^^^    ^^^    ^^^    ^^^    ^^^    ^^^    ^^^
pDJCcoding   CCA    GAG    TTC    CAA    GCC    TCC    AAC    ATC    ATG    CAC    AGC    ATC    AAT    GGC    TAT    GTT 1925   1930   1935   1940   1945   1950   1955   1960   1965
                  *      *      *      *      *      *      *      *      *
pDJCcoding      TTC    GAT    AGT    TTG    CAG    TTG    TCA    GTT    TGT    TTG    CAT    GAA    GTA    GCA    TAC    TGG
                 |                    |                    |                    |
  1. p25Dcod          1930                 1940                 1950                 1960
[ 16902 ]       TTt    GAT    AGT    TTG    CAG    TTG    TCA    GTT    TGT    TTG    CAT    GAg    GTg    GCA    TAC    TGG>
                ^^v    ^^^    ^^^    ^^^    ^^^    ^^^    ^^^    ^^^    ^^^    ^^^    ^^^    ^^v    ^^v    ^^^    ^^^    ^^^
pDJCcoding      TTC    GAT    AGT    TTG    CAG    TTG    TCA    GTT    TGT    TTG    CAT    GAA    GTA    GCA    TAC    TGG 1970   1975   1980   1985   1990   1995   2000   2005   2010   2015
                  *      *      *      *      *      *      *      *      *      *
pDJCcoding     TAC    ATT    CTA    AGC    ATT    GGA    GCA    CAG    ACT    GAC    TTC    CTT    TCT    GTC    TTC    TTC
                |                    |                    |                    |                    |
  1. p25Dc1970        1980                 1990                 2000                 2010
[ 16902 ]      TAC    ATT    CTA    AGC    ATT    GGA    GCA    CAG    ACT    GAC    TTC    CTT    TCT    GTC    TTC    TTC>
               ^^^    ^^^    ^^^    ^^^    ^^^    ^^^    ^^^    ^^^    ^^^    ^^^    ^^^    ^^^    ^^^    ^^^    ^^^    ^^^
pDJCcoding     TAC    ATT    CTA    AGC    ATT    GGA    GCA    CAG    ACT    GAC    TTC    CTT    TCT    GTC    TTC    TTC
```

*Fig. 5G*

```
                   2020  2025  2030  2035  2040  2045  2050  2055  2060
                     *     *     *     *     *     *     *     *     *
pDJCcoding    TCT   GGA   TAT   ACC   TTC   AAA   CAC   AAA   ATG   GTC   TAT   GAA   GAC   ACA   CTC   ACC
                    |                 |                 |                 |                 |
1. p25Dcod 2020              2030              2040              2050              2060
[ 16902 ]     TCT   GGA   TAT   ACC   TTC   AAA   CAC   AAA   ATG   GTC   TAT   GAA   GAC   ACA   CTC   ACC>
              ^^^   ^^^   ^^^   ^^^   ^^^   ^^^   ^^^   ^^^   ^^^   ^^^   ^^^   ^^^   ^^^   ^^^   ^^^   ^^^
pDJCcoding    TCT   GGA   TAT   ACC   TTC   AAA   CAC   AAA   ATG   GTC   TAT   GAA   GAC   ACA   CTC   ACC 2065  2070  2075  2080  2085  2090  2095  2100  2105  2110
              *     *     *     *     *     *     *     *     *     *
pDJCcoding    CTA   TTC   CCA   TTC   TCC   GGA   GAA   ACT   GTC   TTC   ATG   TCG   ATG   GAA   AAC   CCA
               |                 |                 |                 |                 |
1. p25Dcod  2070              2080              2090              2100              2110
[ 16902 ]     CTA   TTC   CCA   TTC   TCa   GGA   GAA   ACT   GTC   TTC   ATG   TCG   ATG   GAA   AAC   CCA>
              ^^^   ^^^   ^^^   ^^^   ^^v   ^^^   ^^^   ^^^   ^^^   ^^^   ^^^   ^^^   ^^^   ^^^   ^^^   ^^^
pDJCcoding    CTA   TTC   CCA   TTC   TCC   GGA   GAA   ACT   GTC   TTC   ATG   TCG   ATG   GAA   AAC   CCA 2115  2120  2125  2130  2135  2140  2145  2150  2155  2160
              *     *     *     *     *     *     *     *     *     *
pDJCcoding    GGA   CTA   TGG   ATT   CTG   GGG   TGC   CAC   AAC   TCA   GAC   TTT   CGG   AAC   AGA   GGC
               |                 |                 |                 |                 |
1. p25Dcod  2120              2130              2140              2150              2160
[ 16902 ]     GGt   CTA   TGG   ATT   CTG   GGG   TGC   CAC   AAC   TCA   GAC   TTT   CGG   AAC   AGA   GGC>
              ^^v   ^^^   ^^^   ^^^   ^^^   ^^^   ^^^   ^^^   ^^^   ^^^   ^^^   ^^^   ^^^   ^^^   ^^^   ^^^
pDJCcoding    GGA   CTA   TGG   ATT   CTG   GGG   TGC   CAC   AAC   TCA   GAC   TTT   CGG   AAC   AGA   GGC 2165  2170  2175  2180  2185  2190  2195  2200  2205
              *     *     *     *     *     *     *     *     *
pDJCcoding    ATG   ACC   GCC   TTA   CTG   AAA   GTT   TCC   AGT   TGT   GAC   AAG   AAC   ACT   GGA   GAT
                                 |                 |                 |                 |
1. p25Dcod                    2170              2180              2190              2200
[ 16902 ]     ATG   ACC   GCC   TTA   CTG   AAg   GTT   TCt   AGT   TGT   GAC   AAG   AAC   ACT   GGt   GAT>
              ^^^   ^^^   ^^^   ^^^   ^^^   ^^v   ^^^   ^^v   ^^^   ^^^   ^^^   ^^^   ^^^   ^^^   ^^v   ^^^
pDJCcoding    ATG   ACC   GCC   TTA   CTG   AAA   GTT   TCC   AGT   TGT   GAC   AAG   AAC   ACT   GGA   GAT 2210  2215  2220  2225  2230  2235  2240  2245  2250  2255
                *     *     *     *     *     *     *     *     *     *
pDJCcoding    TAT   TAC   GAG   GAC   AGT   TAT   GAA   GAT   ATT   TCA   GCA   TAC   TTG   CTG   AGT   AAA
               |                 |                 |                 |                 |
1. p25Dc2210                  2220              2230              2240              2250
[ 16902 ]     TAT   TAC   GAG   GAC   AGT   TAT   GAA   GAT   ATT   TCA   GCA   TAC   TTG   CTG   AGT   AAA>
              ^^^   ^^^   ^^^   ^^^   ^^^   ^^^   ^^^   ^^^   ^^^   ^^^   ^^^   ^^^   ^^^   ^^^   ^^^   ^^^
pDJCcoding    TAT   TAC   GAG   GAC   AGT   TAT   GAA   GAT   ATT   TCA   GCA   TAC   TTG   CTG   AGT   AAA 2260  2265  2270  2275  2280  2285  2290  2295  2300
                *     *     *     *     *     *     *     *     *
pDJCcoding    AAC   AAT   GCC   ATT   GAA   CCA   AGA   AGC   TTC   TCC   CAG   AAC   CCA   CCA   GTC   TTG
               |                 |                 |                 |                 |
1. p25Dcod  2260              2270              2280              2290              2300
[ 16902 ]     AAC   AAT   GCC   ATT   GAA   CCA   AGA   AGC   TTC   TCC   CAG   AAC   CCA   CCA   GTC   TTG>
              ^^^   ^^^   ^^^   ^^^   ^^^   ^^^   ^^^   ^^^   ^^^   ^^^   ^^^   ^^^   ^^^   ^^^   ^^^   ^^^
pDJCcoding    AAC   AAT   GCC   ATT   GAA   CCA   AGA   AGC   TTC   TCC   CAG   AAC   CCA   CCA   GTC   TTG
```

*Fig. 5H*

```
              2305  2310  2315  2320  2325  2330  2335  2340  2345  2350
               *     *     *     *     *     *     *     *     *     *
pDJCcoding   AAA   CGC   CAT   CAA   CGG   GAA   ATA   ACT   CGT   ACT   ACT   CTT   CAA   TCA   GAT   CAA
                    |                       |                       |                       |
1. p25Dcod   2310                    2320                    2330                    2340                    2350
[ 16902 ]    AAA   CGC   CAT   CAA   CGG   GAA   ATA   ACT   CGT   ACT   ACT   CTT   CAg   TCA   GAT   CAA>
             ^^^   ^^^   ^^^   ^^^   ^^^   ^^^   ^^^   ^^^   ^^^   ^^^   ^^^   ^^^   ^^v   ^^^   ^^^   ^^^
pDJCcoding   AAA   CGC   CAT   CAA   CGG   GAA   ATA   ACT   CGT   ACT   ACT   CTT   CAA   TCA   GAT   CAA 2355  2360  2365  2370  2375  2380  2385  2390  2395  2400
               *     *     *     *     *     *     *     *     *     *
pDJCcoding   GAG   GAA   ATT   GAC   TAT   GAT   GAT   ACC   ATA   TCA   GTT   GAA   ATG   AAG   AAG   GAA
                    |                       |                       |                       |                       |
1. p25Dcod          2360                    2370                    2380                    2390                    2400
[ 16902 ]    GAG   GAA   ATT   GAC   TAT   GAT   GAT   ACC   ATA   TCA   GTT   GAA   ATG   AAG   AAG   GAA>
             ^^^   ^^^   ^^^   ^^^   ^^^   ^^^   ^^^   ^^^   ^^^   ^^^   ^^^   ^^^   ^^^   ^^^   ^^^   ^^^
pDJCcoding   GAG   GAA   ATT   GAC   TAT   GAT   GAT   ACC   ATA   TCA   GTT   GAA   ATG   AAG   AAG   GAA 2405  2410  2415  2420  2425  2430  2435  2440  2445
               *     *     *     *     *     *     *     *     *
pDJCcoding   GAT   TTC   GAC   ATT   TAT   GAT   GAG   GAT   GAA   AAT   CAG   AGC   CCC   CGC   AGC   TTT
                          |                       |                       |                       |
1. p25Dcod                2410                    2420                    2430                    2440
[ 16902 ]    GAT   TTt   GAC   ATT   TAT   GAT   GAG   GAT   GAA   AAT   CAG   AGC   CCC   CGC   AGC   TTT>
             ^^^   ^^v   ^^^   ^^^   ^^^   ^^^   ^^^   ^^^   ^^^   ^^^   ^^^   ^^^   ^^^   ^^^   ^^^   ^^^
pDJCcoding   GAT   TTC   GAC   ATT   TAT   GAT   GAG   GAT   GAA   AAT   CAG   AGC   CCC   CGC   AGC   TTT 2450  2455  2460  2465  2470  2475  2480  2485  2490  2495
               *     *     *     *     *     *     *     *     *     *
pDJCcoding   CAA   AAG   AAA   ACA   CGA   CAC   TAT   TTT   ATT   GCT   GCA   GTG   GAG   AGG   CTC   TGG
              |                       |                       |                       |
1. p25Dc2450                         2460                    2470                    2480                    2490
[ 16902 ]    CAA   AAG   AAA   ACA   CGA   CAC   TAT   TTT   ATT   GCT   GCA   GTG   GAG   AGG   CTC   TGG>
             ^^^   ^^^   ^^^   ^^^   ^^^   ^^^   ^^^   ^^^   ^^^   ^^^   ^^^   ^^^   ^^^   ^^^   ^^^   ^^^
pDJCcoding   CAA   AAG   AAA   ACA   CGA   CAC   TAT   TTT   ATT   GCT   GCA   GTG   GAG   AGG   CTC   TGG 2500  2505  2510  2515  2520  2525  2530  2535  2540
               *     *     *     *     *     *     *     *     *
pDJCcoding   GAT   TAT   GGG   ATG   AGT   AGC   TCC   CCA   CAT   GTT   CTA   AGA   AAC   AGG   GCT   CAG
              |                       |                       |                       |
1. p25Dcod   2500                    2510                    2520                    2530                    2540
[ 16902 ]    GAT   TAT   GGG   ATG   AGT   AGC   TCC   CCA   CAT   GTT   CTA   AGA   AAC   AGG   GCT   CAG>
             ^^^   ^^^   ^^^   ^^^   ^^^   ^^^   ^^^   ^^^   ^^^   ^^^   ^^^   ^^^   ^^^   ^^^   ^^^   ^^^
pDJCcoding   GAT   TAT   GGG   ATG   AGT   AGC   TCC   CCA   CAT   GTT   CTA   AGA   AAC   AGG   GCT   CAG 2545  2550  2555  2560  2565  2570  2575  2580  2585  2590
               *     *     *     *     *     *     *     *     *     *
pDJCcoding   AGT   GGC   AGT   GTC   CCT   CAG   TTC   AAG   AAA   GTA   GTA   TTC   CAG   GAA   TTT   ACC
                    |                       |                       |                       |                       |
1. p25Dcod          2550                    2560                    2570                    2580                    2590
[ 16902 ]    AGT   GGC   AGT   GTC   CCT   CAG   TTC   AAG   AAA   GTt   GTt   TTC   CAG   GAA   TTT   ACt>
             ^^^   ^^^   ^^^   ^^^   ^^^   ^^^   ^^^   ^^^   ^^^   ^^v   ^^v   ^^^   ^^^   ^^^   ^^^   ^^v
pDJCcoding   AGT   GGC   AGT   GTC   CCT   CAG   TTC   AAG   AAA   GTA   GTA   TTC   CAG   GAA   TTT   ACC
```

*Fig. 51*

```
              2595   2600   2605   2610   2615   2620   2625   2630   2635   2640
                *      *      *      *      *      *      *      *      *      *
pDJCcoding    GAT    GGC    TCC    TTT    ACT    CAA    CCC    TTA    TAC    CGT    GGA    GAA    CTA    AAT    GAA    CAT
               |                    |                    |                    |                    |
1. p25Dcod          2600                  2610                  2620                  2630                  2640
[ 16902 ]     GAT    GGC    TCC    TTT    ACT    CAg    CCC    TTA    TAC    CGT    GGA    GAA    CTA    AAT    GAA    CAT>
              ^^^    ^^^    ^^^    ^^^    ^^^    ^^v    ^^^    ^^^    ^^^    ^^^    ^^^    ^^^    ^^^    ^^^    ^^^    ^^^
pDJCcoding    GAT    GGC    TCC    TTT    ACT    CAA    CCC    TTA    TAC    CGT    GGA    GAA    CTA    AAT    GAA    CAT 2645   2650   2655   2660   2665   2670   2675   2680   2685
                *      *      *      *      *      *      *      *      *
pDJCcoding    TTG    GGA    CTC    CTG    GGG    CCA    TAT    ATA    AGA    GCA    GAA    GTT    GAA    GAT    AAT    ATC
               |                    |                    |                    |
1. p25Dcod          2650                  2660                  2670                  2680
[ 16902 ]     TTG    GGA    CTC    CTG    GGG    CCA    TAT    ATA    AGA    GCA    GAA    GTT    GAA    GAT    AAT    ATC>
              ^^^    ^^^    ^^^    ^^^    ^^^    ^^^    ^^^    ^^^    ^^^    ^^^    ^^^    ^^^    ^^^    ^^^    ^^^    ^^^
pDJCcoding    TTG    GGA    CTC    CTG    GGG    CCA    TAT    ATA    AGA    GCA    GAA    GTT    GAA    GAT    AAT    ATC 2690   2695   2700   2705   2710   2715   2720   2725   2730   2735
                *      *      *      *      *      *      *      *      *      *
pDJCcoding    ATG    GTT    ACC    TTC    AGA    AAT    CAG    GCC    TCT    CGT    CCC    TAT    TCC    TTC    TAT    TCT
               |                    |                    |                    |                    |
1. p25Dc2690        2700                  2710                  2720                  2730
[ 16902 ]     ATG    GTa    ACt    TTC    AGA    AAT    CAG    GCC    TCT    CGT    CCC    TAT    TCC    TTC    TAT    TCT>
              ^^^    ^^v    ^^v    ^^^    ^^^    ^^^    ^^^    ^^^    ^^^    ^^^    ^^^    ^^^    ^^^    ^^^    ^^^    ^^^
pDJCcoding    ATG    GTT    ACC    TTC    AGA    AAT    CAG    GCC    TCT    CGT    CCC    TAT    TCC    TTC    TAT    TCT 2740   2745   2750   2755   2760   2765   2770   2775   2780
                *      *      *      *      *      *      *      *      *
pDJCcoding    TCC    CTC    ATA    TCA    TAT    GAG    GAA    GAT    CAG    AGG    CAA    GGA    GCA    GAA    CCT    AGA
               |                    |                    |                    |
1. p25Dcod   2740                  2750                  2760                  2770                  2780
[ 16902 ]     agC    CTt    ATt    TCt    TAT    GAG    GAA    GAT    CAG    AGG    CAA    GGA    GCA    GAA    CCT    AGA>
              vv^    ^^v    ^^v    ^^v    ^^^    ^^^    ^^^    ^^^    ^^^    ^^^    ^^^    ^^^    ^^^    ^^^    ^^^    ^^^
pDJCcoding    TCC    CTC    ATA    TCA    TAT    GAG    GAA    GAT    CAG    AGG    CAA    GGA    GCA    GAA    CCT    AGA 2785   2790   2795   2800   2805   2810   2815   2820   2825   2830
                *      *      *      *      *      *      *      *      *      *
pDJCcoding    AAA    AAC    TTT    GTC    AAG    CCT    AAT    GAA    ACC    AAA    ACT    TAC    TTT    TGG    AAA    GTG
               |                    |                    |                    |                    |
1. p25Dcod          2790                  2800                  2810                  2820                  2830
[ 16902 ]     AAA    AAC    TTT    GTC    AAG    CCT    AAT    GAA    ACC    AAA    ACT    TAC    TTT    TGG    AAA    GTG>
              ^^^    ^^^    ^^^    ^^^    ^^^    ^^^    ^^^    ^^^    ^^^    ^^^    ^^^    ^^^    ^^^    ^^^    ^^^    ^^^
pDJCcoding    AAA    AAC    TTT    GTC    AAG    CCT    AAT    GAA    ACC    AAA    ACT    TAC    TTT    TGG    AAA    GTG 2835   2840   2845   2850   2855   2860   2865   2870   2875   2880
                *      *      *      *      *      *      *      *      *      *
pDJCcoding    CAA    CAT    CAT    ATG    GCA    CCC    ACT    AAA    GAT    GAG    TTT    GAC    TGC    AAA    GCC    TGG
               |                    |                    |                    |                    |
1. p25Dcod          2840                  2850                  2860                  2870                  2880
[ 16902 ]     CAA    CAT    CAT    ATG    GCA    CCC    ACT    AAA    GAT    GAG    TTT    GAC    TGC    AAA    GCC    TGG>
              ^^^    ^^^    ^^^    ^^^    ^^^    ^^^    ^^^    ^^^    ^^^    ^^^    ^^^    ^^^    ^^^    ^^^    ^^^    ^^^
pDJCcoding    CAA    CAT    CAT    ATG    GCA    CCC    ACT    AAA    GAT    GAG    TTT    GAC    TGC    AAA    GCC    TGG 2885   2890   2895   2900   2905   2910   2915   2920   2925
                *      *      *      *      *      *      *      *      *
pDJCcoding    GCT    TAT    TTC    TCC    GAT    GTC    GAC    CTG    GAA    AAA    GAT    GTG    CAC    TCA    GGC    CTG
               |                    |                    |                    |
1. p25Dcod          2890                  2900                  2910                  2920
[ 16902 ]     GCT    TAT    TTC    TCt    GAT    GTt    GAC    CTG    GAA    AAA    GAT    GTG    CAC    TCA    GGC    CTG>
              ^^^    ^^^    ^^^    ^^v    ^^^    ^^v    ^^^    ^^^    ^^^    ^^^    ^^^    ^^^    ^^^    ^^^    ^^^    ^^^
pDJCcoding    GCT    TAT    TTC    TCC    GAT    GTC    GAC    CTG    GAA    AAA    GAT    GTG    CAC    TCA    GGC    CTG
```

*Fig. 5J*

```
            2930  2935  2940  2945  2950  2955  2960  2965  2970  2975
              *     *     *     *     *     *     *     *     *     *
pDJCcoding  ATT GGA CCC CTT CTG GTC TGC CAC ACC AAC ACA CTG AAC CCT GCT CAT
             |                     |                 |             |
1. p25Dc2930            2940              2950            2960           2970
[ 16902 ]   ATT GGA CCC CTT CTG GTC TGC CAC ACt AAC ACA CTG AAC CCT GCT CAT>
            ^^^ ^^^ ^^^ ^^^ ^^^ ^^^ ^^^ ^^^ ^^v ^^^ ^^^ ^^^ ^^^ ^^^ ^^^ ^^^
pDJCcoding  ATT GGA CCC CTT CTG GTC TGC CAC ACC AAC ACA CTG AAC CCT GCT CAT 2980  2985  2990  2995  3000  3005  3010  3015  3020
              *     *     *     *     *     *     *     *     *
pDJCcoding  GGG AGA CAA GTG ACA GTA CAG GAA TTT GCT CTG TTT TTC ACC ATC TTC
             |                 |             |             |             |
1. p25Dcod 2980           2990             3000          3010          3020
[ 16902 ]   GGG AGA CAA GTG ACA GTA CAG GAA TTT GCT CTG TTT TTC ACC ATC TTt>
            ^^^ ^^^ ^^^ ^^^ ^^^ ^^^ ^^^ ^^^ ^^^ ^^^ ^^^ ^^^ ^^^ ^^^ ^^^ ^^v
pDJCcoding  GGG AGA CAA GTG ACA GTA CAG GAA TTT GCT CTG TTT TTC ACC ATC TTC 3025 3030  3035  3040  3045  3050  3055  3060  3065  3070
           *    *     *     *     *     *     *     *     *     *
pDJCcoding  GAT GAG ACC AAA AGC TGG TAC TTC ACT GAA AAT ATG GAA AGA AAC TGC
             |             |             |             |             |
1. p25Dcod  3030          3040          3050          3060          3070
[ 16902 ]   GAT GAG ACC AAA AGC TGG TAC TTC ACT GAA AAT ATG GAA AGA AAC TGC>
            ^^^ ^^^ ^^^ ^^^ ^^^ ^^^ ^^^ ^^^ ^^^ ^^^ ^^^ ^^^ ^^^ ^^^ ^^^ ^^^
pDJCcoding  GAT GAG ACC AAA AGC TGG TAC TTC ACT GAA AAT ATG GAA AGA AAC TGC 3075  3080  3085  3090  3095  3100  3105  3110  3115 3120
              *     *     *     *     *     *     *     *     *    *
pDJCcoding  AGG GCT CCC TGC AAT ATC CAG ATG GAA GAT CCC ACT TTT AAA GAG AAT
             |             |             |             |             |
1. p25Dcod            3080          3090          3100          3110          3120
[ 16902 ]   AGG GCT CCC TGC AAT ATC CAG ATG GAA GAT CCC ACT TTT AAA GAG AAT>
            ^^^ ^^^ ^^^ ^^^ ^^^ ^^^ ^^^ ^^^ ^^^ ^^^ ^^^ ^^^ ^^^ ^^^ ^^^ ^^^
pDJCcoding  AGG GCT CCC TGC AAT ATC CAG ATG GAA GAT CCC ACT TTT AAA GAG AAT 3125  3130 3135  3140  3145 3150  3155  3160  3165
              *     *    *     *     *    *     *     *     *
pDJCcoding  TAT CGC TTC CAT GCA ATC AAT GGC TAC ATA ATG GAT ACA CTA CCT GGC
             |             |             |             |
1. p25Dcod              3130          3140          3150          3160
[ 16902 ]   TAT CGC TTC CAT GCA ATC AAT GGC TAC ATA ATG GAT ACA CTA CCT GGC>
            ^^^ ^^^ ^^^ ^^^ ^^^ ^^^ ^^^ ^^^ ^^^ ^^^ ^^^ ^^^ ^^^ ^^^ ^^^ ^^^
pDJCcoding  TAT CGC TTC CAT GCA ATC AAT GGC TAC ATA ATG GAT ACA CTA CCT GGC 3170  3175 3180  3185  3190  3195  3200  3205  3210  3215
              *     *    *     *     *     *     *     *     *     *
pDJCcoding  TTA GTA ATG GCT CAG GAT CAA AGG ATT CGA TGG TAT CTG CTC AGC ATG
             |             |             |             |             |
1. p25Dc3170           3180          3190          3200          3210
[ 16902 ]   TTA GTA ATG GCT CAG GAT CAA AGG ATT CGA TGG TAT CTG CTC AGC ATG>
            ^^^ ^^^ ^^^ ^^^ ^^^ ^^^ ^^^ ^^^ ^^^ ^^^ ^^^ ^^^ ^^^ ^^^ ^^^ ^^^
pDJCcoding  TTA GTA ATG GCT CAG GAT CAA AGG ATT CGA TGG TAT CTG CTC AGC ATG
```

*Fig. 5K*

```
              3220   3225  3230  3235  3240  3245  3250  3255  3260
                *     *     *     *     *     *     *     *     *
pDJCcoding    GGC   AGC   AAT   GAA   AAC   ATC   CAT   TCT   ATT   CAT   TTC   TCC   GGA   CAT   GTG   TTC
               |                 |                 |                 |                 |
1. p25Dcod   3220               3230              3240              3250              3260
[ 16902 ]    GGC   AGC   AAT   GAA   AAC   ATC   CAT   TCT   ATT   CAT   TTC   agt   GGA   CAT   GTG   TTC>
             ^^^   ^^^   ^^^   ^^^   ^^^   ^^^   ^^^   ^^^   ^^^   ^^^   ^^^   vvv   ^^^   ^^^   ^^^   ^^^
pDJCcoding   GGC   AGC   AAT   GAA   AAC   ATC   CAT   TCT   ATT   CAT   TTC   TCC   GGA   CAT   GTG   TTC 3265  3270  3275  3280  3285  3290  3295  3300  3305  3310
              *     *     *     *     *     *     *     *     *     *
pDJCcoding   ACT   GTA   CGA   AAA   AAA   GAG   GAG   TAT   AAA   ATG   GCA   CTG   TAC   AAT   CTC   TAT
              |                 |                 |                 |                 |
1. p25Dcod   3270              3280              3290              3300              3310
[ 16902 ]    ACT   GTA   CGA   AAA   AAA   GAG   GAG   TAT   AAA   ATG   GCA   CTG   TAC   AAT   CTC   TAT>
             ^^^   ^^^   ^^^   ^^^   ^^^   ^^^   ^^^   ^^^   ^^^   ^^^   ^^^   ^^^   ^^^   ^^^   ^^^   ^^^
pDJCcoding   ACT   GTA   CGA   AAA   AAA   GAG   GAG   TAT   AAA   ATG   GCA   CTG   TAC   AAT   CTC   TAT 3315  3320  3325  3330  3335  3340  3345  3350  3355  3360
                *     *     *     *     *     *     *     *     *     *
pDJCcoding    CCC   GGA   GTT   TTC   GAG   ACA   GTG   GAA   ATG   TTA   CCA   TCC   AAA   GCT   GGA   ATT
               |                 |                 |                 |                 |
1. p25Dcod   3320               3330              3340              3350              3360
[ 16902 ]    CCa   GGt   GTT   TTt   GAG   ACA   GTG   GAA   ATG   TTA   CCA   TCC   AAA   GCT   GGA   ATT>
             ^^v   ^^v   ^^^   ^^v   ^^^   ^^^   ^^^   ^^^   ^^^   ^^^   ^^^   ^^^   ^^^   ^^^   ^^^   ^^^
pDJCcoding   CCC   GGA   GTT   TTC   GAG   ACA   GTG   GAA   ATG   TTA   CCA   TCC   AAA   GCT   GGA   ATT 3365 3370  3375  3380  3385  3390  3395  3400  3405
                *    *     *     *     *     *     *     *     *
pDJCcoding    TGG   CGG   GTG   GAA   TGC   CTT   ATT   GGC   GAG   CAT   CTA   CAT   GCT   GGG   ATG   AGC
               |                 |                 |                 |
1. p25Dcod   3370               3380              3390              3400
[ 16902 ]    TGG   CGG   GTG   GAA   TGC   CTT   ATT   GGC   GAG   CAT   CTA   CAT   GCT   GGG   ATG   AGC>
             ^^^   ^^^   ^^^   ^^^   ^^^   ^^^   ^^^   ^^^   ^^^   ^^^   ^^^   ^^^   ^^^   ^^^   ^^^   ^^^
pDJCcoding   TGG   CGG   GTG   GAA   TGC   CTT   ATT   GGC   GAG   CAT   CTA   CAT   GCT   GGG   ATG   AGC 3410  3415  3420  3425  3430  3435  3440  3445  3450  3455
                *     *     *     *     *     *     *     *     *     *
pDJCcoding    ACA   CTT   TTT   CTG   GTG   TAC   TCC   AAT   AAG   TGT   CAG   ACT   CCC   CTG   GGA   ATG
               |                 |                 |                 |                 |
1. p25Dc3410                    3420              3430              3440              3450
[ 16902 ]    ACA   CTT   TTT   CTG   GTG   TAC   agC   AAT   AAG   TGT   CAG   ACT   CCC   CTG   GGA   ATG>
             ^^^   ^^^   ^^^   ^^^   ^^^   ^^^   vv^   ^^^   ^^^   ^^^   ^^^   ^^^   ^^^   ^^^   ^^^   ^^^
pDJCcoding   ACA   CTT   TTT   CTG   GTG   TAC   TCC   AAT   AAG   TGT   CAG   ACT   CCC   CTG   GGA   ATG 3460  3465  3470  3475  3480  3485  3490  3495  3500
                *     *     *     *     *     *     *     *     *
pDJCcoding    GCT   TCT   GGA   CAC   ATT   AGA   GAT   TTT   CAG   ATT   ACA   GCT   TCA   GGA   CAA   TAT
               |                 |                 |                 |                 |
1. p25Dcod   3460               3470              3480              3490              3500
[ 16902 ]    GCT   TCT   GGA   CAC   ATT   AGA   GAT   TTT   CAG   ATT   ACA   GCT   TCA   GGA   CAA   TAT>
             ^^^   ^^^   ^^^   ^^^   ^^^   ^^^   ^^^   ^^^   ^^^   ^^^   ^^^   ^^^   ^^^   ^^^   ^^^   ^^^
pDJCcoding   GCT   TCT   GGA   CAC   ATT   AGA   GAT   TTT   CAG   ATT   ACA   GCT   TCA   GGA   CAA   TAT
```

*Fig. 5L*

```
              3505   3510   3515   3520  3525   3530   3535   3540   3545   3550
                *      *      *      *     *      *      *      *      *      *
pDJCcoding    GGA    CAG    TGG    GCC   CCA    AAG    CTG    GCC    AGA    CTT    CAT    TAT    TCC    GGA    TCA    ATC
                                          |                   |                    |                           |
1. p25Dcod    3510                       3520                3530                 3540                        3550
[ 16902 ]     GGA    CAG    TGG    GCC   CCA    AAG    CTG    GCC    AGA    CTT    CAT    TAT    TCC    GGA    TCA    ATC>
              ^^^    ^^^    ^^^    ^^^   ^^^    ^^^    ^^^    ^^^    ^^^    ^^^    ^^^    ^^^    ^^^    ^^^    ^^^    ^^^
pDJCcoding    GGA    CAG    TGG    GCC   CCA    AAG    CTG    GCC    AGA    CTT    CAT    TAT    TCC    GGA    TCA    ATC 3555   3560   3565   3570  3575   3580   3585   3590   3595   3600
                *      *      *      *     *      *      *      *      *      *
pDJCcoding    AAT    GCC    TGG    AGC   ACC    AAG    GAG    CCC    TTT    TCT    TGG    ATC    AAA    GTT    GAC    CTG
                            |                   |                    |                           |                     |
1. p25Dcod                 3560                3570                 3580                        3590                  3600
[ 16902 ]     AAT    GCC    TGG    AGC   ACC    AAG    GAG    CCC    TTT    TCT    TGG    ATC    AAg    GTg    GAt    CTG>
              ^^^    ^^^    ^^^    ^^^   ^^^    ^^^    ^^^    ^^^    ^^^    ^^^    ^^^    ^^^    ^^v    ^^v    ^^v    ^^^
pDJCcoding    AAT    GCC    TGG    AGC   ACC    AAG    GAG    CCC    TTT    TCT    TGG    ATC    AAA    GTT    GAC    CTG 3605   3610   3615   3620  3625   3630   3635   3640   3645
                *      *      *      *     *      *      *      *      *
pDJCcoding    TTG    GCA    CCA    ATG   ATT    ATT    CAC    GGC    ATC    AAG    ACC    CAG    GGT    GCC    CGT    CAG
                            |                   |                    |                           |
1. p25Dcod                 3610                3620                 3630                        3640
[ 16902 ]     TTG    GCA    CCA    ATG   ATT    ATT    CAC    GGC    ATC    AAG    ACC    CAG    GGT    GCC    CGT    CAG>
              ^^^    ^^^    ^^^    ^^^   ^^^    ^^^    ^^^    ^^^    ^^^    ^^^    ^^^    ^^^    ^^^    ^^^    ^^^    ^^^
pDJCcoding    TTG    GCA    CCA    ATG   ATT    ATT    CAC    GGC    ATC    AAG    ACC    CAG    GGT    GCC    CGT    CAG 3650   3655   3660   3665  3670   3675   3680   3685   3690   3695
                *      *      *      *     *      *      *      *      *      *
pDJCcoding    AAG    TTC    TCC    AGC   CTC    TAC    ATC    TCT    CAA    TTT    ATC    ATC    ATG    TAT    AGT    CTC
                     |                          |                    |                           |
1. p25Dc3650        3660                       3670                 3680                        3690
[ 16902 ]     AAG    TTC    TCC    AGC   CTC    TAC    ATC    TCT    CAg    TTT    ATC    ATC    ATG    TAT    AGT    CTt>
              ^^^    ^^^    ^^^    ^^^   ^^^    ^^^    ^^^    ^^^    ^^v    ^^^    ^^^    ^^^    ^^^    ^^^    ^^^    ^^v
pDJCcoding    AAG    TTC    TCC    AGC   CTC    TAC    ATC    TCT    CAA    TTT    ATC    ATC    ATG    TAT    AGT    CTC 3700   3705   3710   3715  3720   3725   3730   3735   3740
                *      *      *      *     *      *      *      *      *
pDJCcoding    GAT    GGG    AAG    AAG   TGG    CAG    ACT    TAT    CGA    GGA    AAT    TCC    ACT    GGA    ACC    CTC
                     |                   |                    |                           |                    |
1. p25Dcod  3700                        3710                 3720                        3730                 3740
[ 16902 ]     GAT    GGG    AAG    AAG   TGG    CAG    ACT    TAT    CGA    GGA    AAT    TCC    ACT    GGA    ACC    tTa>
              ^^^    ^^^    ^^^    ^^^   ^^^    ^^^    ^^^    ^^^    ^^^    ^^^    ^^^    ^^^    ^^^    ^^^    ^^^    v^v
pDJCcoding    GAT    GGG    AAG    AAG   TGG    CAG    ACT    TAT    CGA    GGA    AAT    TCC    ACT    GGA    ACC    CTC 3745   3750   3755   3760  3765   3770   3775   3780   3785   3790
                *      *      *      *     *      *      *      *      *      *
pDJCcoding    ATG    GTC    TTC    TTT   GGC    AAT    GTG    GAT    TCA    TCT    GGG    ATA    AAA    CAC    AAT    ATT
                            |                   |                    |                           |
1. p25Dcod                 3750                3760                 3770                        3780                  3790
[ 16902 ]     ATG    GTC    TTC    TTT   GGC    AAT    GTG    GAT    TCA    TCT    GGG    ATA    AAA    CAC    AAT    ATT>
              ^^^    ^^^    ^^^    ^^^   ^^^    ^^^    ^^^    ^^^    ^^^    ^^^    ^^^    ^^^    ^^^    ^^^    ^^^    ^^^
pDJCcoding    ATG    GTC    TTC    TTT   GGC    AAT    GTG    GAT    TCA    TCT    GGG    ATA    AAA    CAC    AAT    ATT
```

*Fig. 5M*

```
             3795      3800      3805      3810      3815  3820      3830      3835  3840
               *         *         *         *         *     *         *         *     *
pDJCcoding   TTC AAC CCT CCA ATT ATT GCT CGA TAC ATC CGT TTG CAC CCA ACT CAT
                 |           3810        |             3820            |           3830          |           3840
  1. p25Dcod    3800
[ 16902 ]    TTt AAC CCT CCA ATT ATT GCT CGA TAC ATC CGT TTG CAC CCA ACT CAT>
             ^^v ^^^ ^^^ ^^^ ^^^ ^^^ ^^^ ^^^ ^^^ ^^^ ^^^ ^^^ ^^^ ^^^ ^^^ ^^^
pDJCcoding   TTC AAC CCT CCA ATT ATT GCT CGA TAC ATC CGT TTG CAC CCA ACT CAT 3845      3850      3855      3860      3865  3870      3875      3880      3885
               *         *         *         *         *     *         *         *         *
pDJCcoding   TAT AGC ATT CGC AGC ACT CTT CGC ATG GAG TTG ATG GGC TGT GAT TTA
                 |           3850        |             3860            |           3870          |           3880
  1. p25Dcod
[ 16902 ]    TAT AGC ATT CGC AGC ACT CTT CGC ATG GAG TTG ATG GGC TGT GAT TTA>
             ^^^ ^^^ ^^^ ^^^ ^^^ ^^^ ^^^ ^^^ ^^^ ^^^ ^^^ ^^^ ^^^ ^^^ ^^^ ^^^
pDJCcoding   TAT AGC ATT CGC AGC ACT CTT CGC ATG GAG TTG ATG GGC TGT GAT TTA 3890      3895 3900      3905      3910 3915      3920      3925      3930      3935
               *         *    *         *         *    *         *         *         *         *
pDJCcoding   AAT AGT TGC AGC ATG CCA TTG GGA ATG GAG AGT AAA GCA ATA TCA GAT
                 |           3900        |             3910            |           3920          |           3930
  1. p25Dc3890
[ 16902 ]    AAT AGT TGC AGC ATG CCA TTG GGA ATG GAG AGT AAA GCA ATA TCA GAT>
             ^^^ ^^^ ^^^ ^^^ ^^^ ^^^ ^^^ ^^^ ^^^ ^^^ ^^^ ^^^ ^^^ ^^^ ^^^ ^^^
pDJCcoding   AAT AGT TGC AGC ATG CCA TTG GGA ATG GAG AGT AAA GCA ATA TCA GAT 3940 3945      3950      3955      3960  3965      3970 3975      3980
               *    *         *         *         *     *         *    *         *
pDJCcoding   GCA CAG ATT ACT GCT TCA TCC TAC TTT ACC AAT ATG TTT GCC ACC TGG
                 |           3950        |             3960            |           3970          |           3980
  1. p25Dcod 3940
[ 16902 ]    GCA CAG ATT ACT GCT TCA TCC TAC TTT ACC AAT ATG TTT GCC ACC TGG>
             ^^^ ^^^ ^^^ ^^^ ^^^ ^^^ ^^^ ^^^ ^^^ ^^^ ^^^ ^^^ ^^^ ^^^ ^^^ ^^^
pDJCcoding   GCA CAG ATT ACT GCT TCA TCC TAC TTT ACC AAT ATG TTT GCC ACC TGG 3985 3990      3995      4000      4005  4010      4015      4020      4025      4030
               *    *         *         *         *     *         *         *         *         *
pDJCcoding   TCT CCT TCA AAA GCT CGA CTA CAC CTA CAA GGG AGG AGT AAT GCC TGG
                 |           4000        |             4010            |           4020          |           4030
  1. p25Dcod 3990
[ 16902 ]    TCT CCT TCA AAA GCT CGA CTt CAC CTc CAA GGG AGG AGT AAT GCC TGG>
             ^^^ ^^^ ^^^ ^^^ ^^^ ^^^ ^^v ^^^ ^^v ^^^ ^^^ ^^^ ^^^ ^^^ ^^^ ^^^
pDJCcoding   TCT CCT TCA AAA GCT CGA CTA CAC CTA CAA GGG AGG AGT AAT GCC TGG 4035      4040      4045      4050      4055  4060      4065      4070      4075 4080
               *         *         *         *         *     *         *         *         *    *
pDJCcoding   AGA CCT CAA GTT AAC AAT CCA AAA GAG TGG CTG CAA GTG GAC TTC CAG
                 |           4040        |             4050            |           4060          |           4070          |           4080
  1. p25Dcod
[ 16902 ]    AGA CCT CAg GTg AAt AAT CCA AAA GAG TGG CTG CAA GTG GAC TTC CAG>
             ^^^ ^^^ ^^v ^^v ^^v ^^^ ^^^ ^^^ ^^^ ^^^ ^^^ ^^^ ^^^ ^^^ ^^^ ^^^
pDJCcoding   AGA CCT CAA GTT AAC AAT CCA AAA GAG TGG CTG CAA GTG GAC TTC CAG 4085      4090 4095      4100      4105  4110      4115      4120 4125
               *         *    *         *         *     *         *         *    *
pDJCcoding   AAG ACA ATG AAA GTC ACA GGA GTA ACT ACT CAG GGA GTA AAA TCT CTG
                 |           4090        |             4100            |           4110          |           4120
  1. p25Dcod
[ 16902 ]    AAG ACA ATG AAA GTC ACA GGA GTA ACT ACT CAG GGA GTA AAA TCT CTG>
             ^^^ ^^^ ^^^ ^^^ ^^^ ^^^ ^^^ ^^^ ^^^ ^^^ ^^^ ^^^ ^^^ ^^^ ^^^ ^^^
pDJCcoding   AAG ACA ATG AAA GTC ACA GGA GTA ACT ACT CAG GGA GTA AAA TCT CTG
```

*Fig. 5N*

```
              4130      4135      4140      4145      4150      4155      4160      4165      4170      4175
                *         *         *         *         *         *         *         *         *         *
pDJCcoding    CTT ACC TCT ATG TAC GTG AAG GAG TTC CTC ATA TCG TCG TCG CAA GAT
               |             |             |             |             |
  1. p25Dc4130              4140          4150          4160          4170
[ 16902 ]     CTT ACC agc ATG TAt GTG AAG GAG TTC CTC ATc TCc agc agt CAA GAT>
              ^^^ ^^^ vvv ^^^ ^^v ^^^ ^^^ ^^^ ^^^ ^^^ ^^v ^^v vvv vvv ^^^ ^^^
pDJCcoding    CTT ACC TCT ATG TAC GTG AAG GAG TTC CTC ATA TCG TCG TCG CAA GAT 4180      4185      4190      4195      4200      4205      4210      4215      4220
                     *         *         *         *         *         *         *         *         *
pDJCcoding         GGC CAT CAG TGG ACT CTC TTT TTT CAA AAT GGC AAA GTA AAA GTT TTC
                    |             |             |             |             |
  1. p25Dcod      4180          4190          4200          4210          4220
[ 16902 ]          GGC CAT CAG TGG ACT CTC TTT TTT CAg AAT GGC AAA GTA AAg GTT TTt>
                   ^^^ ^^^ ^^^ ^^^ ^^^ ^^^ ^^^ ^^^ ^^v ^^^ ^^^ ^^^ ^^^ ^^v ^^^ ^^v
pDJCcoding         GGC CAT CAG TGG ACT CTC TTT TTT CAA AAT GGC AAA GTA AAA GTT TTC 4225  4230      4235      4240      4245      4250      4255      4260      4265      4270
                *     *         *         *         *         *         *         *         *         *
pDJCcoding    CAG GGA AAT CAA GAC TCC TTC ACA CCT GTC GTG AAC TCT CTA GAC CCA
               |             |             |             |             |
  1. p25Dcod  4230          4240          4250          4260          4270
[ 16902 ]     CAG GGA AAT CAA GAC TCC TTC ACA CCT GTg GTG AAC TCT CTA GAC CCA>
              ^^^ ^^^ ^^^ ^^^ ^^^ ^^^ ^^^ ^^^ ^^^ ^^v ^^^ ^^^ ^^^ ^^^ ^^^ ^^^
pDJCcoding    CAG GGA AAT CAA GAC TCC TTC ACA CCT GTC GTG AAC TCT CTA GAC CCA 4275      4280      4285      4290      4295      4300      4305      4310      4315      4320
                *         *         *         *         *         *         *         *         *         *
pDJCcoding    CCG TTA CTC ACT CGC TAC CTT CGA ATT CAC CCC CAG AGT TGG GTG CAC
               |             |             |             |             |
  1. p25Dcod              4280          4290          4300          4310          4320
[ 16902 ]     CCG TTA CTg ACT CGC TAC CTT CGA ATT CAC CCC CAG AGT TGG GTG CAC>
              ^^^ ^^^ ^^v ^^^ ^^^ ^^^ ^^^ ^^^ ^^^ ^^^ ^^^ ^^^ ^^^ ^^^ ^^^ ^^^
pDJCcoding    CCG TTA CTC ACT CGC TAC CTT CGA ATT CAC CCC CAG AGT TGG GTG CAC 4325      4330      4335      4340      4345      4350      4355      4360      4365
                     *         *         *         *         *         *         *         *         *
pDJCcoding         CAG ATT GCC CTG AGG ATG GAG GTT CTG GGC TGC GAG GCA CAG GAC CTC
                    |             |             |             |             |
  1. p25Dcod                    4330          4340          4350          4360
[ 16902 ]          CAG ATT GCC CTG AGG ATG GAG GTT CTG GGC TGC GAG GCA CAG GAC CTC>
                   ^^^ ^^^ ^^^ ^^^ ^^^ ^^^ ^^^ ^^^ ^^^ ^^^ ^^^ ^^^ ^^^ ^^^ ^^^ ^^^
pDJCcoding         CAG ATT GCC CTG AGG ATG GAG GTT CTG GGC TGC GAG GCA CAG GAC CTC 4370
                *
pDJCcoding    TAC TGA
               |
  1. p25Dc4370
[ 16902 ]     TAC TGA>
              ^^^ ^^^
pDJCcoding    TAC TGA
```

*Fig. 50*

A 218-bp Fragment of the Human Thyroxin-Binding Globulin (TBG) Gene Contains Full Promoter Activity

5' CTTTCTCT TTTCTTTAC ATGAA GGGTCTGGCAGCCAAA GCAAT CACT CAAAGTTCAAA
                                  CTF/NF1            AP-1      HNF-3
CCTTATCATT TTTGCTTTGT TCCTCTGG CCTTGGTTTG TACATCAG CTTTGAAAAT
    HNF-3                         HNF-3
ACCATCCCAG GGTAATGCT GGG GTTAATTATAAC TAAGAGTGCTCTAG TTTT GCAAT
                          HNF-1
ACAGGACATGC TATAA AAATGGAAAGATGTTGCTTTCTGAGAGATA 3'

From: Y. Hayashi....S. Refetoff. (1993). Molec. Endo. 7 No. 8, pp. 1049-1060

The Immune Response Corporation

*Fig. 21*

```
                                                      KOZAK LEADER/RABBIT B-GLOBIN INTRON1
             850      860      870      880      890      900      910      920      930      940
              *        *        *        *        *        *        *        *        *        *
              a       10_a     20_a                       260      270      280       70_a     80_a     90_>
              |        |        |                          |        |        |         |        |        |
1. rabbit     230|     240|     250|                      260|     270|     280|      290|     300|     310|
[ 462 ]     G TtggTATCCT TTTTACAGCA CAACTTAATG AGACAGATAG AAACTGGTCT TGTAGAAACA GAGTAGTCGC CTGCTTTTCT GCCAGGTGCT
            ^^vv^^^^^^^^ ^^^^^^^^^^

ABP2TBGKLr  G TAAGTATCCT TTTTACAGCA CAACTTAATG AGACAGATAG AAACTGGTCT TGTAGAAACA GAGTAGTCGC CTGCTTTTCT GCCAGGTGCT
(pcy2)

950      960      970
              *        *        *
                        |        |
             320|     330|     340|
1. rabbit    GACTTCTCTC CCCTgggCTg TTTTCaTTTT CTCAG>
[ 462 ]      ^^^^^^^^^^ ^^^^vvv^^v ^^^^v^^^^

ABP2TBGKLr   GACTTCTCTC CCCTTCTCTT TTTTCCTTTT CTCAG
```

*Fig. 23*

Endothelium-Specific Promoters and Enhancers

Enh  Enh  Pro → Human Factor VIII cDNA

| Promoter Name | Characteristics | Reference |
|---|---|---|
| 1) Endothelin-1 | 204 bp; has enhancer seq, TATAA box, TS mapped | Lee et. al. *JBC* 265 No. 18, 1990. |
| 2) Flt-1 (fms-like tyrosine kinase) | ~1 kb, no enhancer, TATAA box, TS mapped | Morishita et. al. *JBC* 270 No. 46, 1995 |
| 3) Nitric Oxide Synthase | ~1 kb, GATAA box, TS mapped | Zhang et. al. *JBC* 270 No. 25, 1995 |

Enhancers

| | | |
|---|---|---|
| 1) c-Fos SRE | 60 nt's, non-tissue specific, active in resting or dividing cells | Treisman, *Cell* 46, 1986 |
| 2) hTF/mTie-2 | Hybrid design, 72 nt's, all endo's | 1998 |

*Fig. 24*

VECTORS AND GENES EXHIBITING INCREASED EXPRESSION

RELATED APPLICATIONS

This application is a continuation of PCT US 98/25354, filed Nov. 25, 1998.

This application claims priority to U.S. Ser. No. 60/071,596, filed on Jan. 16, 1998, and to U.S. Ser. No. 60/067,614, filed Dec. 5, 1997, the entire contents both of which are incorporated herein by reference.

BACKGROUND OF THE INVENTION

Recombinant DNA technology is currently the most valuable tool known for producing highly pure therapeutic proteins both in vitro and in vivo to treat clinical diseases. Accordingly, a vast number of genes encoding therapeutic proteins have been identified and cloned to date, providing valuable sources of protein. The value of these genes is, however, often limited by low expression levels.

This problem has traditionally been addressed using regulatory elements, such as optimal promoters and enhancers, which increase transcription/expression levels of genes. Additional techniques, particularly those which do not rely on foreign sequences (e.g., viral or other foreign regulatory elements) for increasing transcription efficiency of cloned genes, resulting in higher expression, would be of great value.

Accordingly, the present invention provides novel methods for increasing gene expression, and novel genes which exhibit such increased expression.

Gene expression begins with the process of transcription. Factors present in the cell nucleus bind to and transcribe DNA into RNA. This RNA (known as pre-mRNA) is then processed via splicing to remove non-coding regions, referred to as introns, prior to being exported out of the cell nucleus into the cytoplasm (where they are translated into protein). Thus, once spliced, pre-mRNA becomes mRNA which is free of introns and contains only coding sequences (i.e., exons) within its translated region.

Splicing of vertebrate pre-mRNAs occurs via a two step process involving splice site selection and subsequent excision of introns. Splice site selection is governed by definition of exons (Berget et al. (1995) *J. Biol. Chem.* 270(6):2411–2414), and begins with recognition by splicing factors, such as small nuclear ribonucleoproteins (snRNPs), of consensus sequences located at the 3' end of an intron (Green et al. (1986) *Annu. Rev. Genet.* 20:671–708). These sequences include a 3' splice acceptor site, and associated branch and pyrimidine sequences located closely upstream of 3' splice acceptor site (Langford et al. (1983) *Cell* 33:519–527). Once bound to the 3' splice acceptor site, splicing factors search downstream through the neighboring exon for a 5' splice donor site. For internal introns, if a 5' splice donor site is found within about 50 to 300 nucleotides downstream of the 3' splice acceptor site, then the 5' splice donor site will generally be selected to define the exon (Robberson et al. (1990) *Mol. Cell. Biol.* 10(1):84–94), beginning the process of spliceosome assembly.

Accordingly, splicing factors which bind to 3' splice acceptor and 5' splice donor sites communicate across exons to define these exons as the original units of spliceosome assembly, preceding excision of introns. Typically, stable exon complexes will only form and internal introns thereafter be defined if the exon is flanked by both a 3' splice acceptor site and 5' splice donor site, positioned in the correct orientation and within 50 to 300 nucleotides of one another.

It has also been shown that the searching mechanism defining exons is not a strict 5' to 3' (i.e., downstream) scan, but instead operates to find the "best fit" to consensus sequence (Robberson et al., supra. at page 92). For example, if a near-consensus 5' splice donor site is located between about 50 to 300 nucleotides downstream of a 3' splice acceptor site, it may still be selected to define an exon, even if it is not consensus. This may explain the variety of different splicing patterns (referred to as "alternative splicing") which is observed for many genes.

SUMMARY OF THE INVENTION

The present invention provides novel DNAs which exhibit increased expression of a protein of interest. The novel DNAs also can be characterized by increased levels of cytoplasmic mRNA accumulation following transcription within a cell, and by novel splicing patterns. The present invention also provides expression vectors which provide high tissue-specific expression of DNAs, and compositions for delivering such vectors to cells. The invention further provides methods of increasing gene expression and/or modifying the transcription pattern of a gene. The invention still further provides methods of producing a protein by recombinant expression of a novel DNA of the invention.

In one embodiment, a novel DNA of the invention comprises an isolated DNA (e.g., gene clone or cDNA) containing one or more consensus or near consensus splice sites (3' splice acceptor or 5' splice donor) which have been corrected. Such consensus or near consensus splice sites can be corrected by, for example, mutation (e.g., substitution) of at least one consensus nucleotide with a different, preferably non-consensus, nucleotide. These consensus nucleotides can be located within a consensus or near consensus splice site, or within an associated branch sequence (e.g., located upstream of a 3' splice acceptor site). Preferred consensus nucleotides for correction include invariant (i.e., conserved) nucleotides, including one or both of the invariant bases (AG) present in a 3' splice acceptor site; one or both of the invariant bases (GT) present in a 5' splice donor site; or the invariant A present in the branch sequence of a 3' splice acceptor site.

If the consensus or near consensus splice site is located within the coding region of a gene, then the correction is preferably achieved by conservative mutation. In a particularly preferred embodiment, all possible conservative mutations are made within a given consensus or near consensus splice site, so that the consensus or near consensus splice site is as far from consensus as possible (i.e., has the least homology to consensus as is possible) without changing the coding sequence of the consensus or near consensus splice site.

In another embodiment, a novel DNA of the invention comprises at least one non-naturally occurring intron, either within a coding sequence or within a 5' and/or 3' non-coding sequence of the DNA. Novel DNAs comprising one or more non-naturally occurring introns may further comprise one or more consensus or near consensus splice sites which have been corrected as previously summarized.

In a particular embodiment of the invention, the present invention provides a novel gene encoding a human Factor VIII protein. This novel gene comprises one or more non-naturally occurring introns which serve to increase transcription of the gene, or to alter splicing of the gene. The gene may alternatively or additionally comprise one or more consensus splice sites or near consensus splice sites which have been corrected, also to increase transcription of the gene, or to alter splicing of the gene. In one embodiment, the Factor VIII gene comprises the coding region of the full-length human Factor VIII gene, except that the coding region has been modified to contain an intron spanning, overlapping or within the region of the gene encoding the β-domain. This novel gene is therefore expressed as a β-domain deleted human Factor VIII protein, since all or a portion of the β-domain coding sequence (defined by an intron) is spliced out during transcription.

A particular novel human Factor VIII gene of the invention comprises the nucleotide sequence shown in SEQ ID NO:1. Another particular novel human Factor VIII gene of the invention comprises the coding region of the nucleotide sequence shown in SEQ ID NO:3 (nucleotides 1006–8237). Particular novel expression vectors of the invention comprise the complete nucleotide sequences shown in SEQ ID NOS: 2, 3 and 4. These vectors include novel 5' untranslated regulatory regions designed to provide high liver-specific expression of human Factor VIII protein.

In still other embodiments, the invention provides a method of increasing expression of a DNA sequence (e.g., a gene, such as a human Factor VIII gene), and a method of increasing the amount of mRNA which accumulates in the cytoplasm following transcription of a DNA sequence. In addition, the invention provides a method of altering the transcription pattern (e.g., splicing) of a DNA sequence. The methods of the present invention each involve correcting one or more consensus or near consensus splice sites within the nucleotide sequence of a DNA, and/or adding one or more non-naturally occurring introns into the nucleotide sequence of a DNA.

In a particular embodiment, the invention provides a method of simultaneously increasing expression of a gene encoding human Factor VIII protein, while also altering the gene's splicing pattern. The method involves inserting into the coding region of the gene an intron which spans, overlaps or is contained within the portion of the gene encoding the β-domain. The method may additionally or alternatively comprise correcting within either the coding sequence or the 5' or 3' untranslated regions of the novel Factor VIII gene, one or more consensus or near consensus splice sites.

In yet another embodiment, the invention provides a method of producing a human Factor VIII protein, such as a β-domain deleted Factor VIII protein, by introducing an expression vector containing a novel human Factor VIII gene of the invention into a host cell capable of expressing the vector, under conditions appropriate for expression, and allowing for expression of the vector to occur.

BRIEF DESCRIPTION OF THE FIGURES

FIG. 2 shows the conservative correction of a near consensus 3' splice acceptor site. The correction is made by silently mutating the A of the invariant (conserved) AG base pair to C, G, or T which does not affect the coding sequence of the intron because Ser is encoded by three alternate codons.

FIGS. 4A–4C shows the silent nucleotide substitution made at each of the 99 positions maked by arrows in FIG. 3, as well as the codon containing the substitution and the amino acid encoded.

FIGS. 5A–5O is a comparison of the coding sequence of (a) plasmid pDJC (top) containing the coding region of the human β-domain deleted Factor VIII cDNA modified by making 99 conservative point mutations to correct all near consensus splice sites within the coding region, and (b) plasmid p25D (bottom) containing the same coding sequence prior to making the 99 point mutations. Point mutations (substitutions) are indicated by a "v" between the two aligned sequences and correspond to the positions within the pDJC coding sequence shown in FIG. 3. Plasmid p25D contains the same coding region as does plasmid pCY-2 shown in FIG. 7 and referred to throughout the text.

FIG. 21 shows the nucleotide sequence of the human thyroxin binding globulin (TBG) promoter, also containing clustered liver-specific enhancer elements.

FIG. 23 is a comparison of the nucleotide sequences of the rabbit β-globin IVS before (top line) and after (bottom line) optimization to contain consensus 5' splice donor, 3' splice acceptor, branch, and translation initiation sites. Five nucleotides were also changed from purines to pyrimidines to optimize the pyrimidine track.

FIG. 24 contains a list of various endothelium-specific promoters and enhancers, and characteristics associated with these promoters and enhancers.

DETAILED DESCRIPTION OF THE INVENTION

Definitions

Figure 1:
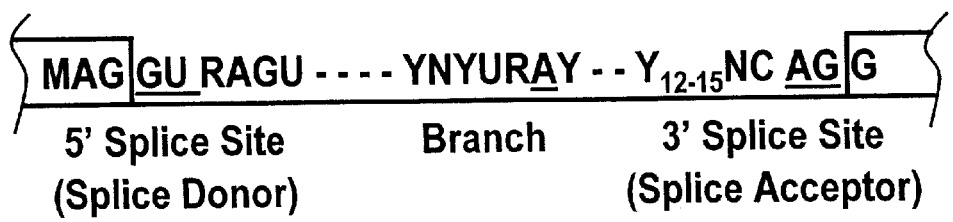
FIG. 1 shows the nucleotide sequence of an RNA intron. The GU of the 5' splice donor site, the AG of the 3' splice acceptor site, and the A of the Branch are invariant bases (100% conserved and essential for recognition as splice sites). U is T in a DNA intron. The Branch sequence is located upstream from the 3' splice acceptor site at a distance sufficient to allow for lariat formation during spliceosome assembly (typically within 30–60 nucleotides). N is any nucleotide. Splicing will occur 5' of the GT base pair within the 5' splice donor site, and 3' of the AG base pair.

The present invention is described herein using the following terms which shall be understood to have the following meanings:

An "isolated DNA" means a DNA molecule removed from its natural sequence context (i.e., from its natural genome). The isolated DNA can be any DNA which is capable of being transcribed in a cell, including for example, a cloned gene (genomic or cDNA clone) encoding a protein of interest, operably linked to a promoter. Alternatively, the isolated DNA can encode an antisense RNA.

A "5' consensus splice site" means a nucleotide sequence comprising the following bases: MAGGTRAGT, wherein M is (C or A), wherein R is (A or G) and wherein GT is essential for recognition as a 5' splice site (hereafter referred to as the "essential GT pair" or the "invariant GT pair").

A "3' consensus splice site" means a nucleotide sequence comprising the following bases (Y>8)NYAGG, wherein Y>8 is a pyrimidine track containing at least eight (most commonly twelve to fifteen or more) tandem pyrimidines (i.e., C or T (U if RNA)), wherein N comprises any nucleotide, wherein Y is a is a pyrimidine, and wherein the AG is essential for recognition as a 3' splice site (hereafter referred to as the "essential AG pair" or the "invariant AG pair"). A "3' consensus splice site" is also preceded upstream (at a sufficient distance to allow for lariat formation, typically at least about 40 bases) by a "branch sequence" comprising the following seven nucleotide bases: YNYTRAY, wherein Y is a pyrimidine (C or T), N is any nucleotide, R is a purine (A or G), and A is essential for recognition as a branch sequence (hereafter referred to as "the essential A" or the "invariant A"). When all seven branch nucleotides are located consecutively in a row, the branch sequence is a "consensus branch sequence."

A "near consensus splice site" means a nucleotide sequence which:

(a) comprises the essential 3' AT pair, and is at least about 50% homologous, more preferably at least about 60–70% homologous, and most preferably greater than 70% homologous to a 3' consensus splice site, when aligned with the consensus splice site for purposes of comparison; or (b) comprises the essential 5' GT pair, and is at least about 50% homologous, more preferably at least about 60–70% homologous, and most preferably greater than 70% homologous to a 5' consensus splice site, when aligned with the consensus splice site for purposes of comparison.

Homology refers to sequence similarity between two nucleic acids. Homology can be determined by comparing a position in each sequence which may be aligned for purposes of comparison. When a position in the compared sequence is occupied by the same nucleotide base, then the molecules are homologous at that position. A degree of homology between sequences is a function of the number of matching or homologous positions shared by the sequences.

As will be described in more detail below, additional criteria for selecting "near consensus splice sites" can be used, adding to the definition provided above. For example, if a near consensus splice site shares homology with a 5' consensus splice site in only 5 out of 9 bases (i.e., about 55% homology), then these bases can be required to be located consecutively in a row. It can additionally or alternatively be required that a 3' near consensus splice site be preceded by a consensus branch sequence (i.e., no mismatches allowed), or followed downstream by a consensus or near consensus 5' splice donor site, to make the selection more stringent.

The term "corrected" as used herein refers to a near consensus splice site mutated by substitution of at least one nucleotide shared with a consensus splice site, hereafter referred to as a "consensus nucleotide". The consensus nucleotide within the near consensus splice site is substituted with a different, preferably non-consensus nucleotide. This makes the near consensus splice site "farther from consensus."

If the near consensus splice site is within a coding region of a gene, then the correction is preferably a conservative mutation. A "conservative mutation" means a base mutation which does not affect the amino acid sequence coded for, also known as a "silent mutation." Accordingly, in a preferred embodiment of the invention, correction of a near consensus splice site located within the coding region of a gene includes making all possible conservative mutations to consensus nucleotides within the site, so that the near consensus splice site is as far from consensus as possible without changing the amino acid sequence it encodes.

A "Factor VIII gene" as used herein means a gene (e.g., a cloned genomic gene or a cDNA) encoding a functional human Factor VIII protein from any species (e.g., human or mouse). A Factor VIII gene which is "full-length" comprises the complete coding sequence of the human Factor VIII gene found in nature, including the region encoding the β-domain. A Factor VIII gene which "encodes a β-domain deleted Factor VIII protein" or "a β-domain deleted Factor VIII gene" lacks all or a portion of the region of the full-length gene encoding the β-domain and, therefore, is transcribed and expressed as a "truncated" or "β-domain deleted" Factor VIII protein. A gene which "is expressed as a β-domain deleted Factor VIII protein" includes not only a gene which encodes a β-domain deleted Factor VIII protein, but also a novel Factor VIII gene provided by the present invention which comprises the coding region of a full-length Factor VIII gene, except that it additionally contains an intron spanning the portion of the gene encoding the β-domain. The term "spans" means that the intron overlaps, encompasses, or is encompassed by the portion of the gene encoding the β domain. The portion of the gene spanned by the intron is then spliced out of the gene during transcription, so that the resulting mRNA is expressed as a truncated or β-domain deleted Factor VIII protein.

A "truncated" or "β-domain deleted" Factor VIII protein includes any active Factor VIII protein (human or otherwise) which contains a deletion of all or a portion of the β-domain.

A "non-naturally occurring intron" means an intron (defined by a 5' splice donor site and a 3' splice acceptor site) which has been engineered into a gene, and which is not present in the natural DNA or pre-mRNA nucleotide sequences of the gene.

An "expression vector" means any DNA vector (e.g., a plasmid vector) containing the necessary genetic elements for expression of a novel gene of the present invention. These elements, including a suitable promoter and preferably also a suitable enhancer, are "operably linked" to the gene, meaning that they are located at a position within the vector which enables them to have a functional effect on transcription of the gene.

Identification of Consensus and Near Consensus Splice Sites

A consensus or near consensus splice site can be identified within a DNA, or its corresponding RNA transcript, by evaluating the nucleotide sequence of the DNA for the presence of a sequence which is identical or highly homologous to either a 3' consensus splice acceptor site or a 5' consensus splice donor site (FIG. 1). Such consensus and near consensus sites can be located within any portion of a given DNA (e.g., a gene), including the coding region of the DNA and any 3' and 5' untranslated regions.

To identify 3' consensus and near consensus splice acceptor sites, a DNA (or corresponding RNA) sequence is analyzed for the presence of one or more nucleotide sequences which includes an AG base pair, and which is either identical to or at least about 50% homologous, more preferably at least about 60–70% sequence homologous, to the sequence: (T/C)≧8 N(C/T)AGG. In a preferred embodiment, the nucleotide sequence is also followed upstream, typically by about 40 bases, by a nucleotide sequence which is identical to or highly homologous (e.g., at least about 50%–95% homologous) to a branch consensus sequence comprising the following bases: (C/T)N(C/T)T(A/G)A(C/T), wherein N is any nucleotide, and A is invariant (i.e., essential). By way of example, in studies described herein, consensus and near consensus 3' splice sites were selected for correction within a gene encoding Factor VIII using the following criteria: the consensus or near consensus site (a) contained an AG pair, and (b) contained no more than three mismatches to a 3' consensus site.

To identify 5' consensus and near consensus splice donor sites, a DNA (or corresponding RNA) sequence can be analyzed for the presence of one or more nucleotide sequences which contains a GT base pair, and which is either identical to or at least about 50% homologous, more preferably at least about 60–70% homologous, to the sequence: (A/C)AGGT(A/G)AGT. By way of example, in studies described herein, consensus and near consensus 5' splice sites were selected for correction within a gene encoding Factor VIII using the following criteria: the consensus or near consensus site (a) contained a GT pair, and (b) contained no more than four mismatches to a 5' consensus site, provided that if it contained four mismatches, they were located consecutively in a row.

Evaluation of DNA or RNA sequences for the presence of one or more consensus or near consensus splice sites can be performed in any suitable manner. For example, nucleotide sequences can be manually analyzed. Alternatively, a computer algorithm can be employed to search nucleotide sequences for specified base patterns (e.g., the MacVector™ program). The latter approach is preferred for large DNAs or RNAs, particularly because it allows for easy implementation of multiple search parameters.

Correction of Consensus and Near Consensus Splice Sites

In one embodiment of the invention, splice and branch sequences which are consensus, or near consensus, are corrected by substitution of one or more consensus nucleotides within the site. The consensus nucleotide within the site is preferably substituted with a non-consensus nucleotide. For example, if the nucleotide being substituted is a C (i.e., a pyrimidine) and the consensus sequence contains either C or T, then the nucleotide is preferably substituted by an A or G (i.e., a purine), thereby making the consensus or near consensus splice site "farther from consensus."

In a preferred embodiment of the invention, consensus and near consensus sites which are located within a coding region of a gene are corrected by conservative substitution of one or more nucleotides so that the correction does not affect the amino acid sequence coded for. Such conservative or "silent" mutation of codons to preserve coding sequences is well known in the art. Accordingly, the skilled artisan will be able to select appropriate base substitutions to retain the coding sequence of any codon which forms all or part of a consensus or near consensus splice site. For example, as shown in FIG. 2, if a 3' near consensus splice site contains a TCA codon encoding serine, and the A is a consensus nucleotide (e.g., part of the essential AG pair, then this nucleotide can be substituted with a C, G, or a T to correct the 3' near consensus splice site (e.g., making it no longer near consensus because it does not contain the essential AG pair required for a 3' near consensus splice site), without affecting the coding sequence of the codon.

Accordingly, in a preferred embodiment of the invention, correction of consensus or near consensus splice sites which are specifically located within the coding region of a gene is achieved by substitution of one or both bases of an essential AG or GT pair within the consensus or near consensus splice site, with a base which does not alter the coding sequence of the site. Correction of consensus or near consensus branch sequences is similarly achieved by substitution of the essential A within the consensus or near consensus branch site, with a base which does not alter the coding sequence of the site. By correcting any of these essential bases, the splice or branch site will no longer be consensus or near consensus.

In another preferred embodiment, correction of consensus or near consensus splice sites which are specifically located within the coding region of a gene is achieved by making all possible conservative mutations to consensus nucleotides within the site, so that the consensus or near consensus splice site is as far from consensus as possible but encodes the same amino acid sequence.

Other preferred corrections of the invention include corrections of 3' consensus and near consensus splice sites which are followed downstream (e.g., by approximately 50–350 nucleotides) by a consensus or near consensus 5' splice donor site. Other preferred corrections of the invention include corrections of 5' consensus and near consensus splice sites which are preceded upstream (e.g., by about 50–350 nucleotides) by a consensus or near consensus 3' splice acceptor site.

For consensus or near consensus splice sites which are located outside the coding region of a gene, for example, in a 3' or 5' untranslated region (UTR), alternative approaches to correction can also be employed. For instance, because preservation of the coding sequence is not a consideration, the near consensus splice site can be corrected not only by any base substitution, but also by addition or deletion of one or more bases within the consensus or near consensus splice site, making the site farther from consensus.

Techniques for making nucleotide base substitutions, additions and deletions as described above are well known in the art. For example, standard point mutation may be employed to substitute one or more bases within a near consensus splice site with a different (e.g., non-consensus) base. Alternatively, as described in detail in the examples below, entire genes or portions thereof can be reconstructed (e.g., resynthesized using PCR), to correct multiple consensus and near consensus splice sites within a particular region of a gene. This approach is particularly advantageous if a gene contains a high concentration of consensus and/or near consensus splice sites within a given region.

Figure 3:
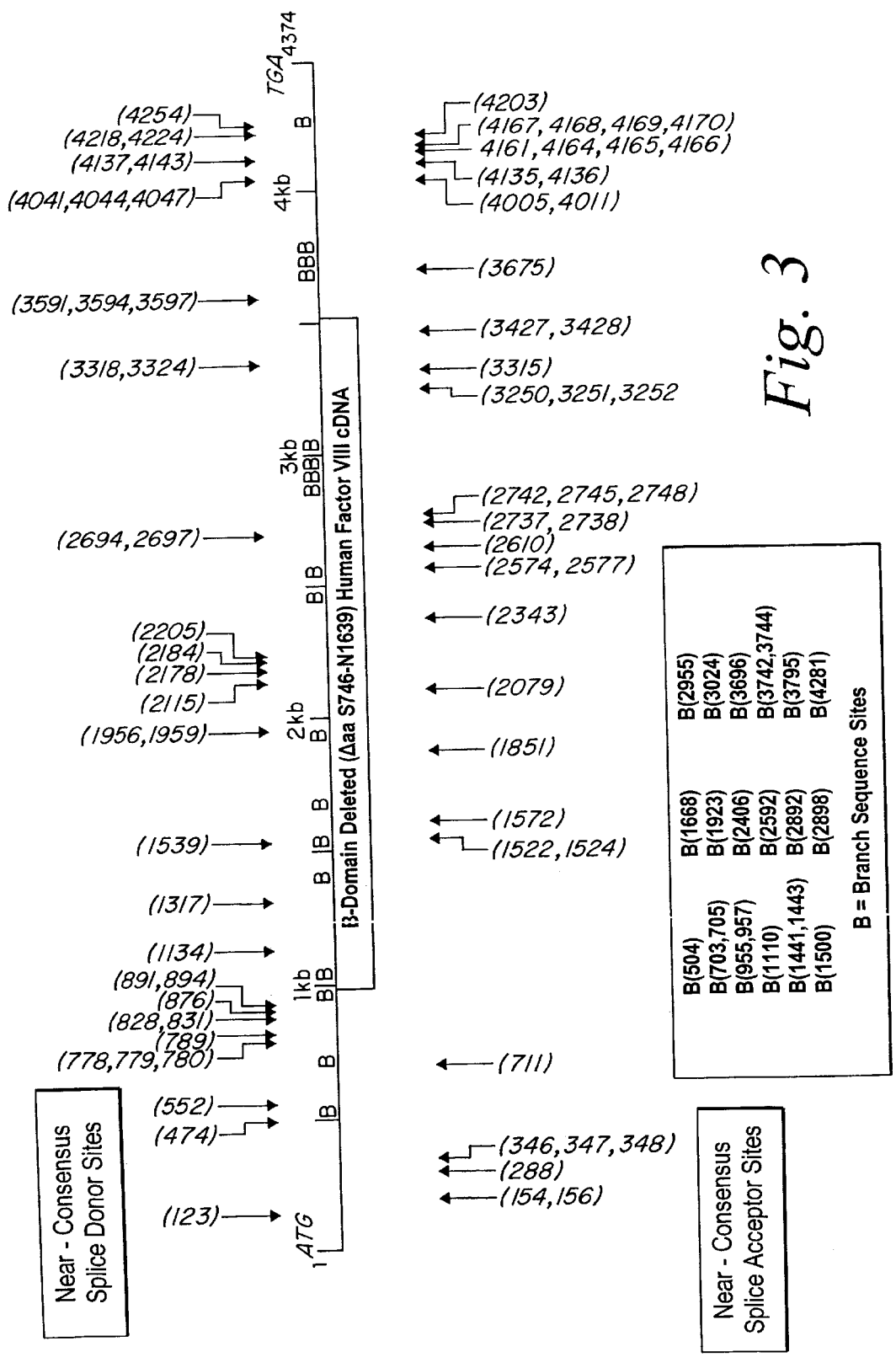
FIG. 3 is a map of the coding region of a β-domain deleted human Factor VIII cDNA, showing the positions of the 99 silent point mutations which were made within the coding region (contained in plasmid pDJC) to conservatively correct all near consensus splice sites. Numbering of nucleotides begins with the ATG start coding of the coding sequence. Arrows above the map show positions mutated within near consensus 5' splice donor sites. Arrows below the map show positions mutated within near consensus 3' splice acceptor sites. Each "B" shown on the map shows a position mutated within a consensus branch sequence.

In a specific embodiment, the invention features a novel Factor VIII gene containing one or more consensus or near consensus splice sites which have been corrected by substitution of one or more consensus nucleotides within the site. As part of the present invention, the coding region of a gene (cDNA) encoding human β-domain deleted Factor VIII protein (nucleotides 1006–5379 of SEQ ID NO:2) was evaluated as described herein and found to contain 23 near consensus 5' splice (donor) sequences, 22 near consensus 3' splice (acceptor) sequences, and 18 consensus branch sequences (shown in FIG. 3). A new coding sequence (SEQ ID NO:1) was then developed for this gene to correct all 3' and 5' near consensus splice sites by conservative mutation. In total, 99 point mutations were made to the coding region. The location of each of these point mutations is shown in FIG. 3. The specific base substitution made in each of these point mutations is shown in FIGS. 4(A–C).

Figure 6:
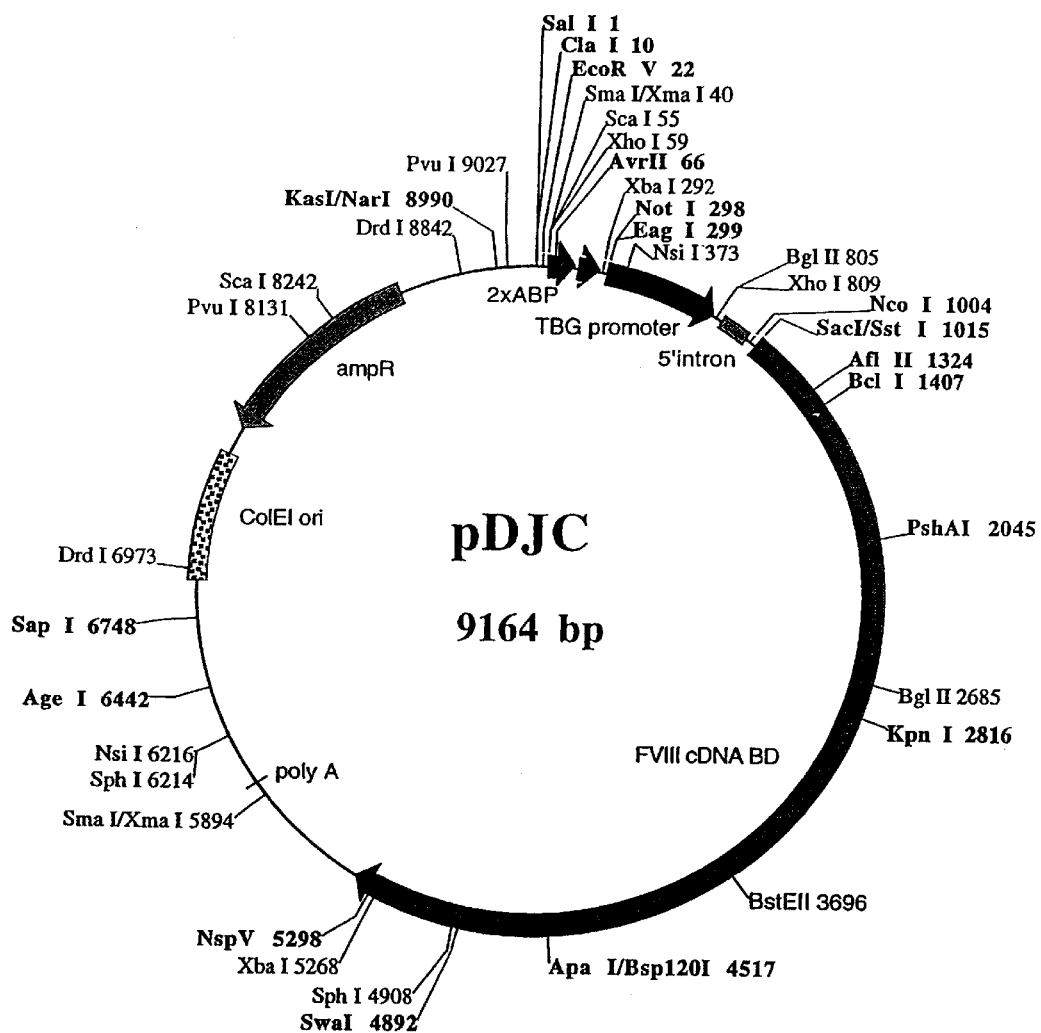
FIG. 6 shows a map of plasmid pDJC including restriction sites used for cloning, regulatory elements within the 5' untranslated region, and the corrected human β-domain deleted Factor VIII cDNA coding sequence.
Figure 7:
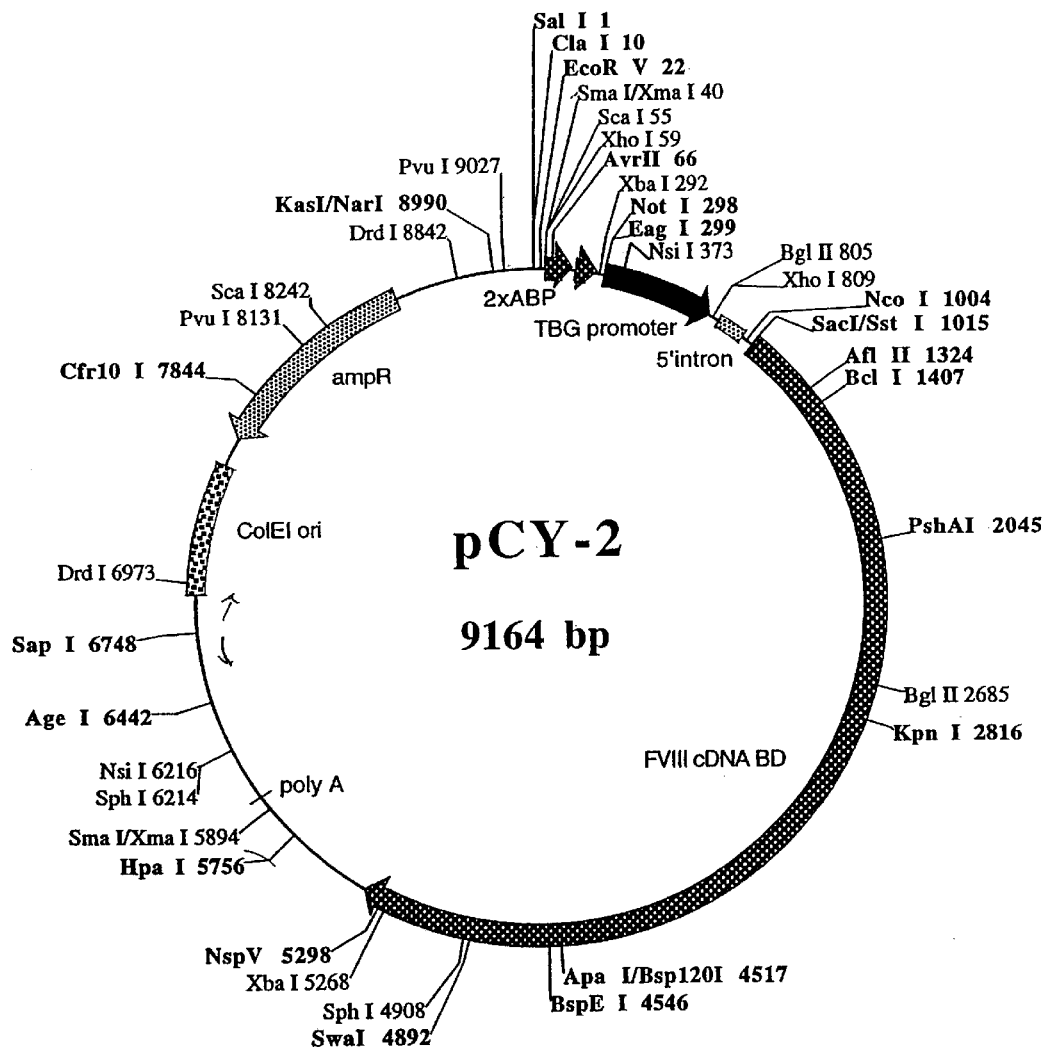
FIG. 7 shows a map of plasmid pCY-2 including restriction sites used for cloning, regulatory elements within the 5' untranslated region, and the uncorrected (i.e., naturally-occurring) human β-domain deleted Factor VIII cDNA coding sequence. pCY-2 and pDJC are identical except for their coding sequences.

A comparison of this new coding sequence (SEQ ID NO: 1) and the original uncorrected sequence (nucleotides 1006–5379 of SEQ ID NO:2), also showing the positions and specific substitutions made in each of the ninety-nine point mutations, is shown in FIGS. 5(A–O). A plasmid vector, referred to as pDJC, containing the new (i.e., corrected) Factor VIII gene coding sequence, including restriction sites used to synthesize the gene and regulatory elements used to express the gene, is shown in FIG. 6. A plasmid vector, referred to as pCY2, containing the original, uncorrected Factor VII gene, including restriction sites and regulatory elements used to express the gene, is shown in FIG. 7.

Figure 8:
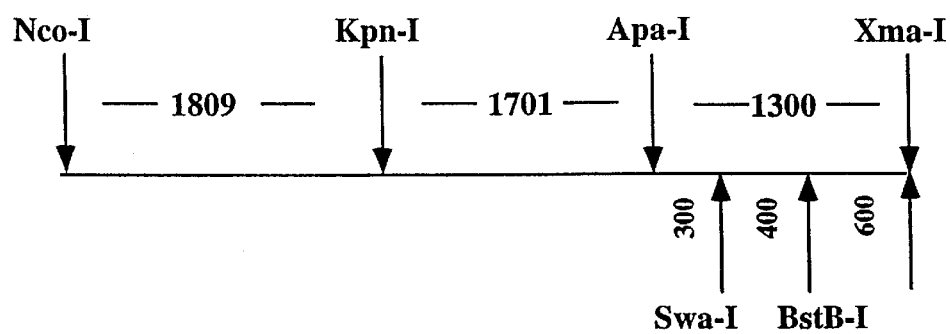
FIG. 8 is a map of the human β-domain deleted Factor VIII cDNA coding region showing the five sections of the cDNA (delineated by restriction sites) which can be synthesized (using overlapping 60-mer oligonucleotides) to contain corrected near consensus splice sites, and then and assembled together to produce a new, corrected coding region.

As described in further detail in the examples below, all 99 consensus base corrections within the coding region of pDJC can be made by synthesizing overlapping oligonucleotides (based on the sequence of pCY2 shown in SEQ ID NO:2) which contain the desired corrections. A schematic illustration of this process is shown in FIG. 8. In total, 185 overlapping 60-mer oligonucleotides can be synthesized, and assembled in five segments using the method of Stemmer et al. (1995) Gene 164: 49–53. Prior to assembly, each segment can be sequenced and tested in in vitro transfection assays (e.g., nuclear and cytoplasmic RNA analysis) in pCY2.

As an alternative to the "correct all" approach described above, selective correction of consensus and near consensus splice sites can also be employed. This involves selecting only (a) consensus sites, and near consensus splice sites which are close to consensus, and/or (b) consensus sites and near consensus sites which are located at positions which render these sites more likely to function as a splice donor or acceptor site. To select only nucleotide sequences which are complete consensus or which are close to consensus, evaluation of a given nucleotide sequence is limited to analyzing the nucleotide sequence for sequences which are identical to or are highly homologous (e.g., greater than 70–80% homologous) to a 3' or 5' consensus splice site. To select only nucleotide sequences which are located at positions which render these sites more likely to function as a splice donor or acceptor site, the location of each 3' consensus or near consensus splice site must be evaluated with respect to the position of any neighboring 5' consensus or near consensus splice sites. If a 3' consensus or near consensus splice site is located approximately 50–350 bases upstream from a 5' consensus or near consensus splice site, then these 3' and 5' splice sites are likely to function as a splice acceptor and donor sites. Therefore, these sites are preferably, and selectively, removed.

By way of example, particular consensus and/or near consensus 5' splice donor and 3' splice acceptor sites, as shown in FIG. 3, can be selected within the coding region of the cDNA encoding human β-domain deleted Factor VIII (nucleotides 1006–5379 of SEQ ID NO:2) for preferred correction, based on their relative locations (i.e., 3' splice acceptor site located approximately 50–350 bases upstream from 5' near consensus splice site). Such preferred selective corrections can include, for instance, the near consensus 3' splice acceptor site spanning nucleotide base 1851 of the coding region (see FIG. 3) and any of the near consensus 5' splice donor sites located within 50–350 bases downstream of this near consensus 3' splice acceptor site, such as those spanning positions 1956, 1959, 2115, 2178 and 2184.

Splice site correction as provided herein can be applied to any gene known in the art. For example, the complete nucleotide sequence of other (e.g., full-length and β-domain deleted) Factor VIII genes (both genomic clones and cDNAs) are described in U.S. Pat. No. 4,757,006, U.S. Pat. No. 5,618,789, U.S. Pat. No. 5,683,905, and U.S. Pat. No. 4,868,112, the disclosures of which are incorporated by reference herein. The nucleotide sequences of these genes can be analyzed for consensus and near consensus splice sites, and thereafter corrected, using the guidelines and procedures provided herein.

In addition, other genes, particularly large genes containing several introns and exons, are also suitable candidates for splice site correction. Such genes, include, for example, the gene encoding Factor IX, or the cystic fibrosis transmembrane regulator (CFTR) gene described in U.S. Pat. No. 5,240,846, or nucleic acids encoding CFTR monomers, as described in U.S. Pat. No. 5,639,661. The disclosures of both of these patents are accordingly incorporated by reference herein.

Addition of Introns

Figure 14:
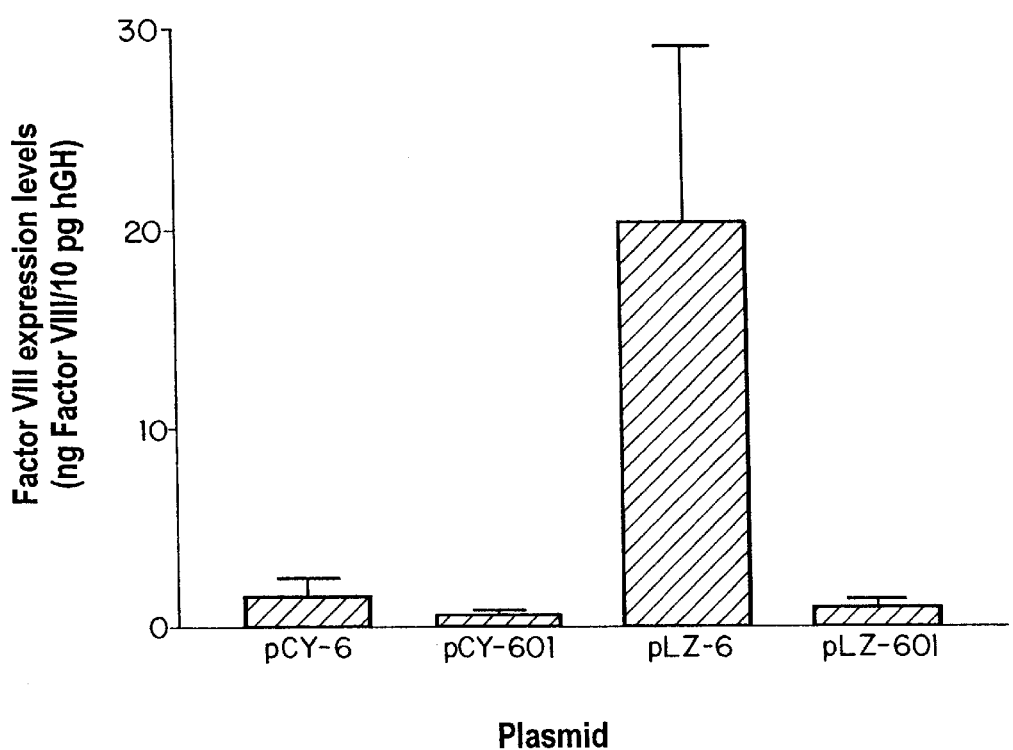
FIG. 14 is a graphic comparison of human Factor VIII expression for (a) pCY-6 (containing the coding region of the full-length human Factor VIII cDNA, as well as a 5' untranslated region derived from the second IVS of rabbit beta globin gene), (b) pCY-601 (containing the coding region of the full-length human Factor VIII cDNA, without the rabbit beta globin IVS), (c) pLZ-6 (containing the coding region of a full-length human Factor VIII cDNA with an intron spanning the β-domain, as well as the rabbit beta globin IVS), and (d) pLZ-601 (containing the coding region of a full-length human Factor VIII cDNA with an intron spanning the majority of the β-domain, without the rabbit beta globin IVS). Expression is given in nanograms. Transfection efficiencies were normalized to expression of human growth hormone (hGH). Each bar represents a summary of four separate transfection experiments.

In another embodiment, a novel gene of the invention includes one or more non-naturally occurring introns which have been added to the gene to increase expression of the gene, or to alter the splicing pattern of the gene. The present invention provides the first known instance of gene engineering which involved adding a non-naturally-occurring intron within the coding sequence of a gene, particularly without affecting the activity of the protein encoded by the gene. The benefit of intron addition in this context is at least two-fold. First, as shown in FIG. 14 in the context of the human Factor VIII gene, addition of one or more introns into a gene increases the expression of the gene compared to the same gene without the intron. Second, the intron, when placed within the coding sequence of the gene, can be used to beneficially alter the splicing pattern of the gene (e.g., so that a particular protein of interest is expressed), and/or to increase cytoplasmic accumulation of mRNA transcribed from the gene.

Novel genes of the present invention may also contain introns outside of the coding region of the gene. For example, introns may be added to the 3' or 5' non-coding regions of the gene (utranslated regions (UTRs)). In a preferred embodiment of the invention, an intron is added upstream of the gene in the 5' UTR, as shown in pDJC (FIG. 6) and pCY2 (FIG. 7). Such introns may include newly engineered introns or pre-existing introns. In a preferred embodiment of the invention, the intron is derived from the rabbit β-globin intron (IVS).

In a particular embodiment, the invention provides a novel human Factor VIII gene which includes within its coding region one or more introns. If the gene comprises the coding region of a full-length human Factor VIII gene, then at least one of these introns preferably spans (i.e., overlaps, encompasses or is encompassed by) the portion of the gene encoding the β-domain. This portion of the gene is then spliced out during transcription of the gene, so that the gene is expressed as a β-domain deleted protein (i.e., a Factor VIII protein lacking all or a portion of the β-domain).

A β-domain deleted human Factor VIII protein possesses known advantages over a full-length human Factor VIII protein (also known as human Factor VIII:C), including reduced immunogenicity (Toole et al. (1986) PNAS 83: 5939–5942). Moreover, it is well known that the β-domain is not needed for activity of the Factor VIII protein. Thus, a novel Factor VIII gene of the invention provides the dual benefit of (1) increased and (2) preferred protein expression.

Addition of one or more introns into a gene can be achieved by adding a 5' splice donor site and a 3' splice acceptor site (FIG. 1) into the nucleotide sequence of the gene at a desired location. If the intron is being added to remove a portion of the coding sequence from the gene, then a 5' splice donor site is placed at the 5' end of the portion being removed (i.e., defined by the intron) and a 3' splice acceptor site is placed at the 3' end of the portion to be removed. Preferably, the 5' splice donor and 3' splice acceptor sequences are consensus, including the branch sequence located upstream of the 3' splice site, so that they will be favored (and more likely bound) by cellular splicing machinery over any surrounding near consensus splice sites.

As shown in FIG. 1, splicing will occur 5' of the essential GT base pair within the 5' splice donor site, and 3' of the essential AG base pair within the 3' splice acceptor site. Thus, for introns added to coding sequences of genes, the intron is preferably designed to that, upon splicing, the coding sequence is unaffected. This can be done by designing and adding 5' splice donor and 3' splice acceptor sites which include only conservative (i.e., silent) changes to the nucleotide sequence of the gene, so that addition of these splice sites does not alter the coding sequence.

Figure 11:
FIG. 11 shows the nucleotide sequences of the exon/intron boundaries (SEQ ID NO:5) flanking the β-domain coding region in plasmid pLZ-6 (containing the full-length human Factor VIII cDNA). The 5' splice donor site was added so that splicing would occur 5' of the "g" shown at position 2290. The 3' splice acceptor site was added so that splicing would occur 3' of the "g" shown at position 5147. Following splicing of the intron created by these splice sites, amino acids Gln-744 and Asn-1639 of the full-length human Factor VIII protein are brought together, resulting in a deletion of amino acids 745 to 1638 (numbering is in reference to Ala-1 of the mature human Factor VIII protein following cleavage of the 19 amino acid signal peptide). Capital letters represent nucleotide bases which remain within exons of the mRNA. Small case letters represent nucleotide bases which are spliced out of the mRNA as part of the intron.

For example, as part of the present invention, an intron was engineered into the coding sequence of a full-length cDNA encoding human Factor VIII (1006–8061 of SEQ ID NO:4). The intron spanned the portion of the gene encoding the β-domain (nucleotides 2290–5147 of SEQ ID NO:4, encoding amino acid residues 745–1638). As described in the examples below, this intron was created by adding a 5' splice donor site (100% consensus) so that splicing would occur immediately 5' of the coding sequence of the β-domain. A 3' splice acceptor site was also added so that splicing would occur immediately 3' of the coding sequence of the β-domain. FIG. 11 shows the nucleotide sequences (SEQ ID NO:5) of the precise boundaries of the resulting intron that was added.

The nucleotide sequence for the 5' splice donor site of the added intron was derived from the pre-existing splice donor sequence found at the 5' end of IVS (Intron) 13 of genomic Factor VIII. This intron precedes exon 14, the exon which contains the sequence coding for the β-domain. The inserted sequence also contained the first nine bases of IVS 13 following the splice donor sequence.

The sequence for the 3' splice acceptor site was derived from the pre-existing splice acceptor sequence found at the 3' end of IVS 14 of genomic Factor VIII. This intron follows exon 14, the β-domain-containing exon. The inserted 3' splice acceptor site also contained 130 bases upstream of the splice acceptor in IVS 14. This upstream region contains at least two near-consensus branch sequences.

Thus, both the 3' and 5' engineered splice sites were designed to take advantage of pre-existing nucleotide sequences within the β-domain region of the human Factor VIII gene.

Figure 10:
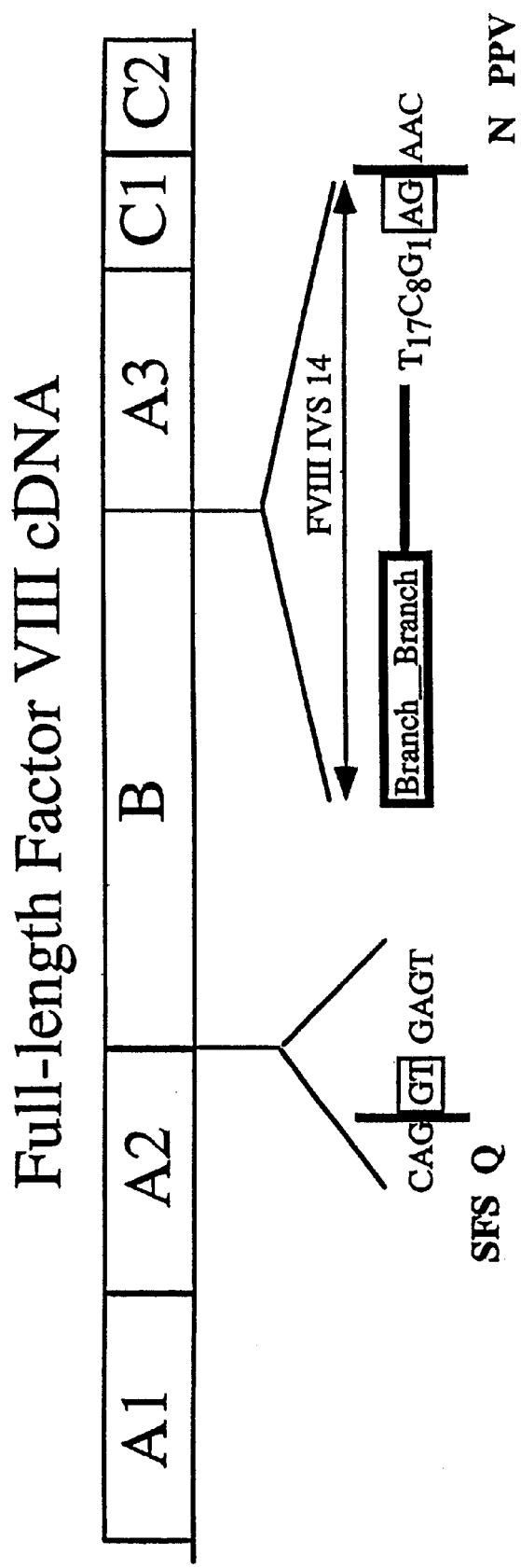
FIG. 10 is a map of the full-length human Factor VIII gene, showing the A1, A2, B, A3, C1 and C2 domains. Following expression of the gene, the β domain is naturally cleaved out of the protein. The map shows the 5' and 3' splice sites inserted within the B region of the gene (in plasmid pLZ-6) so that, during pre-mRNA processing of the gene, the majority of the B region will be spliced out. Segments A2 and A3 of the gene will then be juxtaposed, coding for amino acids SFSQNPPV at the juncture.
Figure 12:
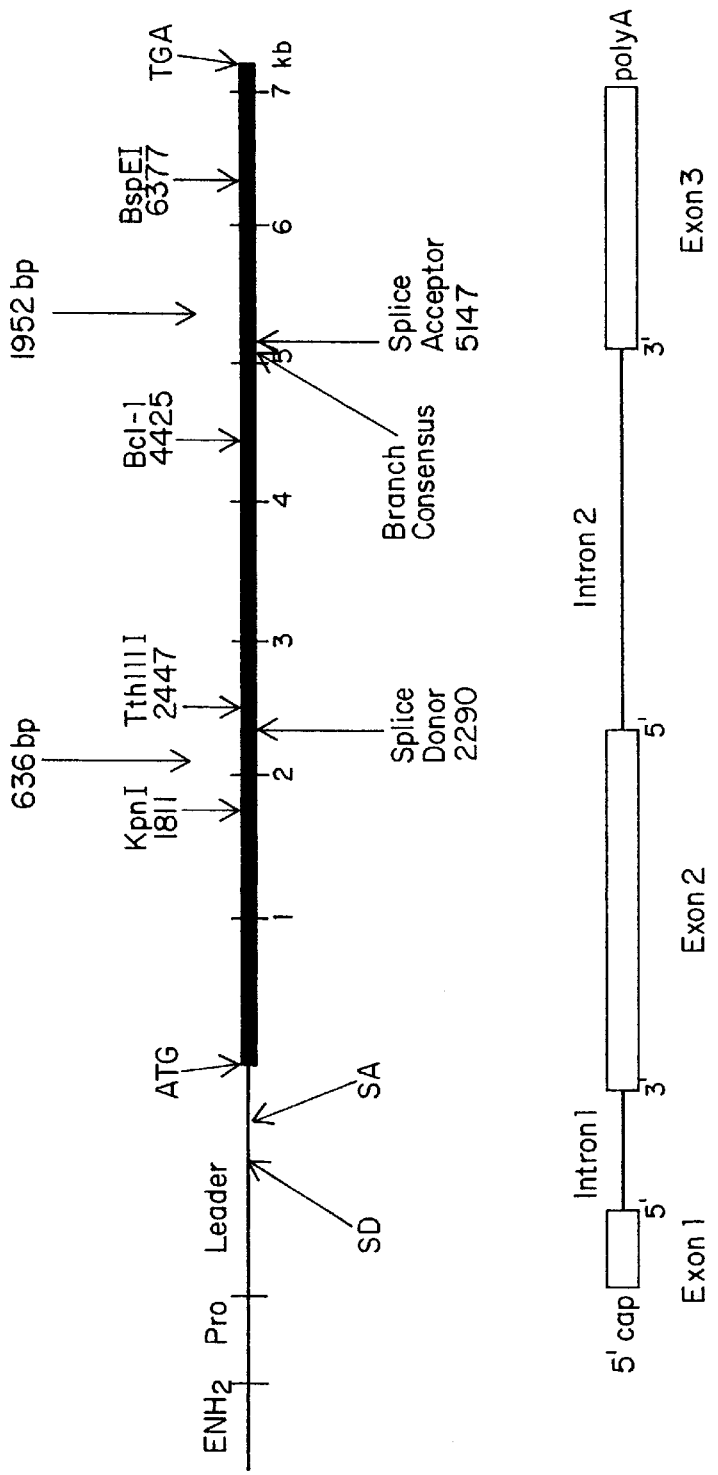
FIG. 12 is a map of the coding region of the full-length human Factor VII gene showing (a) ATG (start) and TGA (stop) codons, (b) restriction sites within the coding region, (c) 5' splice donor (SD) and 3' splice acceptor (SA) sites of a rabbit β-globin intron positioned upstream of the coding region within the 5' untranslated region, (d) 5' splice donor and 3' splice acceptor sites added within the coding region defining an internal intron spanning the β-domain.
Figure 13:
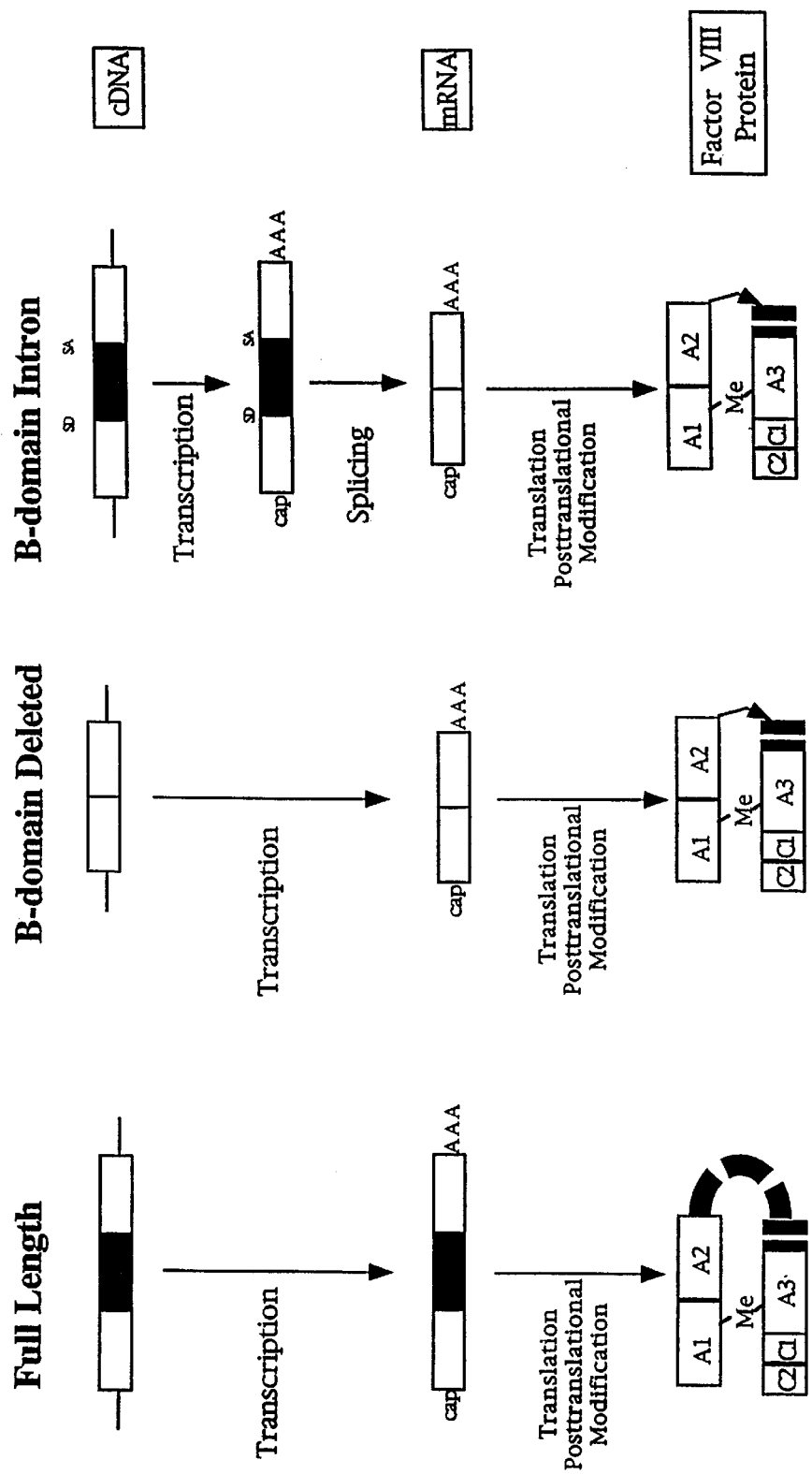
FIG. 13 is a schematic illustration comparing the process of transcription, expression and post-translational modification for human Factor VIII produced from (a) a full-length human Factor VIII gene, (b) a β-domain deleted human Factor VIII gene, and (c) a full-length human Factor VIII gene containing an intron spanning the β-domain coding region.

The 5' splice donor, 3' splice acceptor, and branch sequences of the added intron were further modified so that they were 100% consensus (i.e., congruent to their respective consensus splicing sequences). Modifications (e.g., base substitutions) were chosen so as to not alter the coding sequence of bases located upstream of the 5' splice site and downstream of the 3' splice site (i.e., flanking the boundaries of the intron). A map showing the various domains of the full-length Factor VIII gene, along with the 5' splice donor and 3' splice acceptor sites inserted into the gene, is shown in FIG. 10. The complete nucleotide sequences of the intron boundaries (i.e., 5' splice donor and 3' splice acceptor) are shown in FIG. 11 (SEQ ID NO:5). A map showing the location of the location of the 5' splice donor and 3' splice acceptor sites with respect to various restriction sites (used to clone in the sites) is shown in FIG. 12. As shown schematically in FIG. 13, the resulting novel Factor VIII gene, in contrast to a full-length Factor VIII gene or a gene encoding β-domain deleted Factor VIII, is transcribed as a pre-mRNA which contains the region encoding the β-domain, but is then spliced to remove the majority of this region, so that the resulting mRNA is expressed as a β-domain deleted protein. A complete expression plasmid (pLZ-6) containing the coding sequence of this novel Factor VIII gene, as well as an engineered 5' untranslated region containing regulatory elements designed to provide high, liver-specific expression, comprises the nucleotide sequence shown in SEQ ID NO:3. Bases 1006–8237 of pLZ-6 (SEQ ID NO:3) correspond to the coding region of the novel Factor VIII gene.

Accordingly, in a preferred embodiment, the invention provides a novel Factor VIII gene comprising a non-naturally occurring intron spanning all or a portion of the β-domain region of the gene. In one embodiment, the gene comprises the coding region of the nucleotide sequence shown in SEQ ID NO:3. The gene may also contain further modifications, such as additional introns, or one or more corrected consensus or near consensus splice sites as described herein. In particular, the gene may further comprise one or more introns upstream of the coding sequence of the gene, within the 5' UTR. As shown in FIGS. 6 and 7, a preferred intron for insertion within this region is the rabbit β-globin intron (IVS). In addition, consensus and near consensus splice site corrections can be made to the gene, such as those shown in FIGS. 3 and 4(A–C).

Optimization of 5' and 3' Untranalated Regions for High Tissue-Specific Gene Expression Novel DNAs of the invention are preferably in a form suitable for transcription and/or expression by a cell. Generally, the DNA is contained in an appropriate vector (e.g., an expression vector), such as a plasmid, and is operably linked to appropriate genetic regulatory elements which are functional in the cell. Such regulatory sequences include, for example, enhancer and promoter sequences which drive transcription of the gene. The gene may also include appropriate signal and polyadenylation sequences which provide for trafficking of the encoded protein to intracellular destinations or export of the mRNA. The signal sequence may be a natural sequence of the protein or an exogenous sequence.

Suitable DNA vectors are known in the art and include, for example, DNA plasmids and transposable genetic elements containing the aforementioned genetic regulatory and processing sequences. Particular expression vectors which can be used in the invention include, but are not limited to, pUC vectors (e.g., pUC19) (University of California, San Francisco) pBR322, and pcDNAI (InVitrogen, Inc.). An expression plasmid, pMT2LA8, encoding a β-domain deleted Factor VIII protein is described, for example, by Pitman et al. (1993) *Blood* 81(11):2925–2935). Entire coding sequences for these plasmid vectors are also provided herein (SEQ ID NOS: 4 and 2, respectively).

Suitable regulatory sequences required for gene transcription, translation, processing and secretion are art-recognized, and are selected to direct expression of the desired protein in an appropriate cell. Accordingly, the term "regulatory sequence", as used herein, includes any genetic element present 5' (upstream) or 3' (downstream) of the translated region of a gene and which control or affect expression of the gene, such as enhancer and promoter sequences (e.g., viral promoters, such as SV40 and CMV promoters). Such regulatory sequences are discussed, for example, in Goeddel, *Gene expression Technology: Methods in Enzyamology*, page 185, Academic Press, San Diego, Calif. (1990), and can be selected by those of ordinary skill in the art for use in the present invention.

In a preferred embodiment of the invention, the 5' and/or 3' untranslated regions (UTRs) of a gene construct (e.g., a novel DNA of the invention) are optimized to provide high, tissue-specific expression. Such optimization can include, for example, selection of optimal tissue-specific promoters and enhancers, multerimization of genetic elements, insertion of one or more introns within or outside of the coding sequence, correction of near-consensus 5' splice donor and 3' splice acceptor sites within or outside of the coding sequence, optimization of transcription initiation and termination sites, insertion of RNA export elements, and addition of polyadenylation trimer cassettes to insulate transription. In preferred embodiments of the invention, a combination of the aforementioned elements and sequence modifications are selected and engineered into the gene construct to provide optimized expression.

For many applications of human gene therapy, it is desirable to express proteins in the liver, which has the highest rate of protein synthesis per gram of tissue. For example, effective gene therapy for human Factor VIII requires sufficient levels and duration of protein expression in hepatocytes where Factor VIII is naturally produced, and/or in endothelial cells (ECs) where von Willebrand factor is produced, a protein which stabilizes the secretion of Factor VIII. Thus, in one embodiment, the invention provides a gene construct (e.g., expression vector) optimized to produce high levels and duration of liver-specific protein expression. In a particular embodiment, the invention provides a human Factor VIII gene construct, optimized to produce high levels and duration of liver-specific or endothelium-specific protein expression. This is achieved, for example, by selecting optimal liver-specific and endothelium-specific promoters and enhancers, and by combining these tissue-specific elements with other genetic elements and modifications to increase gene transcription.

Accordingly, for high levels and duration of gene expression in the liver, suitable promoters include, for example, promoters known to contain liver-specific elements. In one embodiment, the invention employs the thyroid binding globulin (TBG) promoter described by Hayashi et al. (1993) *Molec. Endocrinol.* 7:1049–1060. As shown in FIG. 21, the TBG promoter contains hepatic nuclear factor (HNF) enhancer elements and provides the additional advantage of having a precisely mapped transcriptional start site. This allows insertion of a leader sequence, preferably optimized as described herein, between the promoter and the transcriptional start site. FIG. 21 also shows the complete nucleotide sequence of the TBG promoter (SEQ ID NO:10).

For high levels and duration of gene expression in endothelium, suitable endothelium-specific promoters include, for example, the human endothelin-1 (ET-1) gene promoter described by Lee et al. (1990) *J. Biol. Chem.* 265(18), the fms-like tyrosine kinase promoter (Flt-1) described by Morishita et al. (1995) *J. Biol. Chem.* 270(46), the Tie-2 promoter described by Korhonen et al. (1995) *Blood* 86(5):1828–1835, and the nitric oxide synthase promoter described by Zhang et al. (1995) *J. Biol. Chem.* 270(25)) (see FIG. 24).

Figure 20:
FIG. 20 shows the nucleotide sequence of the human alpha-1 microglobulin/bikunin (ABP) enhancer. Clustered liver-specific elements are underlined and labeled HNF-1, HNF-3 and HNF-4.

Promoters selected for use in the invention are preferably paired with a suitable ubiquitous or tissue-specific enhancer designed to augment transcription levels. For example, in one embodiment, a liver-specific promoter, such as the TBG promoter, is used in conjunction with a liver-specific enhancer. In a preferred embodiment, the invention employs one or more copies of the liver-specific alpha-1 microglobulin/bikunin (ABP) enhancer described by Rouet et al. (1992) *J. Biol. Chem.* 267:20765–20773, in combination with the TBG promoter. As shown in FIG. 20, the ABP enhancer contains a cluster of HNF enhancer elements common to many liver-specific genes within a short nucleotide sequence, making it suitable to multerimize. When multerimized, the ABP enhancer generally exhibits increased activity and functions in either orientation within a gene construct.

Thus, in one embodiment, the invention provides an expression vector or DNA construct comprising one or more copies of a liver-specific or endothelium-specific promoter and a liver-specific or endothelium-specific enhancer, the promoter and enhancer being derived from different genes, such as thyroid binding globulin gene and the alpha-1 microglobulin/bikunin gene.

Alternatively, strong ubiquitous (i.e., non-tissue specific) enhancers can be used in conjunction with tissue-specific promoters, such as the TBG promoter or the ET-1 promoter, to achieve high levels and duration of tissue-specific expression. Such ubiquitous enhancers include, for example, the human c-fos (SRE) gene enhancer described by Treisman et al. (1986) *Cell* 46 which, when used in combination with liver-specific promoters (e.g., TBG) or endothelium-specific promoters (e.g., ET-1), provide high levels of tissue-specific expression, as demonstrated in studies described herein.

Figure 15:
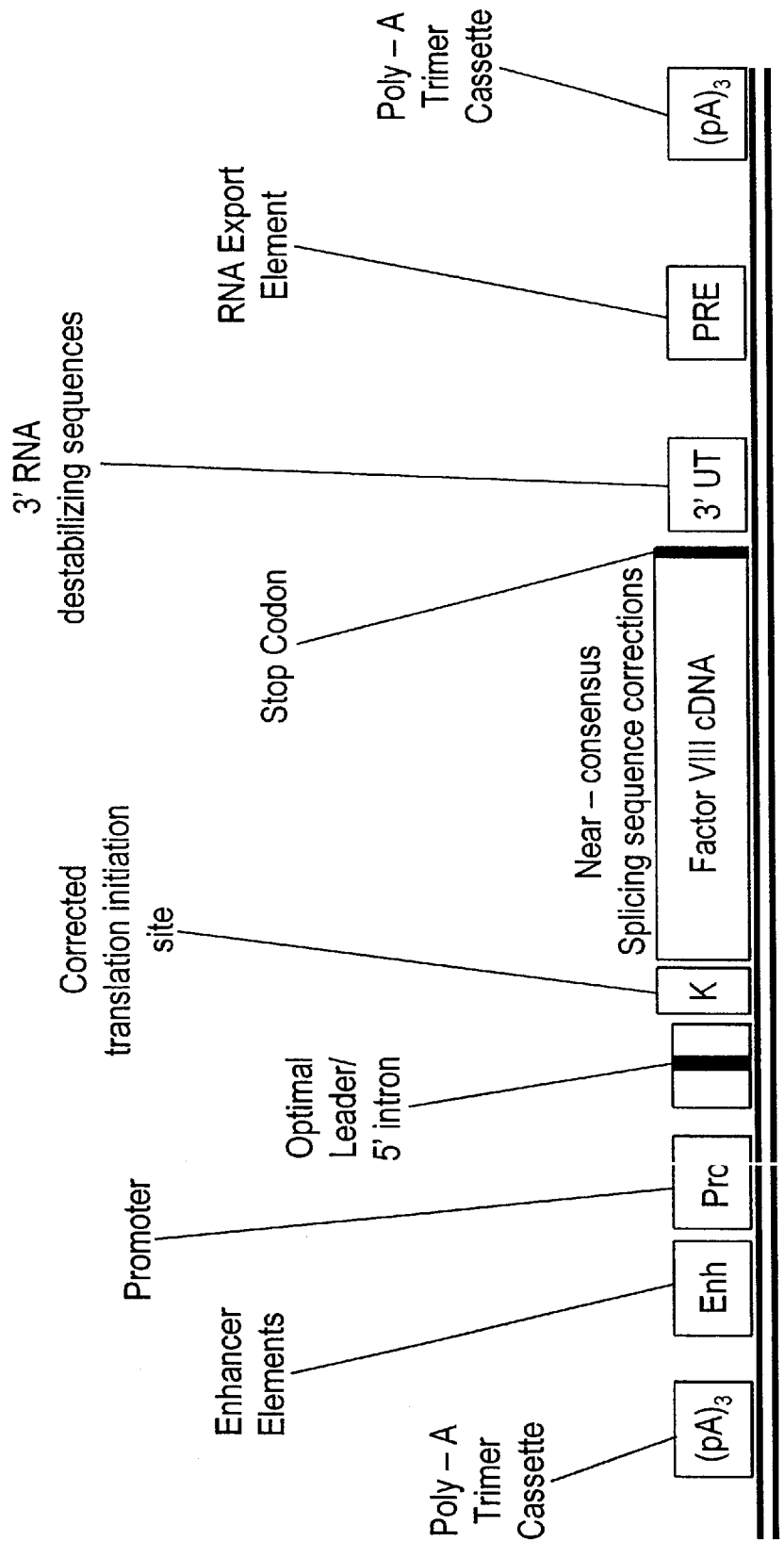
FIG. 15 shows areas within the human Factor VIII transcription unit for sequence optimization.

Accordingly, in a particular embodiment, the invention provides a gene construct which is optimized for specific expression in liver cells by inserting within its 5' untranslated region one or more copies of the ABP enhancer (preferably two copies) coupled upstream with the TBG promoter, as shown in FIG. 15. Specific gene constructs, such as pCY2 and pDJC, containing these elements inserted upstream of the coding region for human Factor VIII (β-domain deleted and full-length with intron spanning the β-domain), are shown in FIGS. 6 and 7, respectively. In another particular embodiment, the gene construct is optimized for specific expression in endothelial cells by inserting within its 5' region one or more copies of the c-fos SRE enhancer, or an endothelial-specific enhancer (e.g., the human tissue factor (hTF/m) enhancer described by Parry et al. (1995) *Arterioscler. Thromb. Vasc. Biol.* 15:612–621) coupled upstream with the ET-1 promoter.

In addition to selecting optimal promoters and enhancers, optimization of a gene construct can include the use of other genetic elements within the transcriptional unit of the gene to increase and/or prolong expression. In one embodiment, one or more introns (e.g., non-naturally occurring introns) are inserted into the 5' or 3' untranslated region (UTR) of the gene. Introns from a broad variety of known genes (e.g., mammalian genes) can be used for this purpose. In one embodiment, the invention employs the first intron (IVS) from the rabbit β-globin gene comprising the nucleotide sequence shown in FIG. 23 (SEQ ID NO:6).

Figure 16:
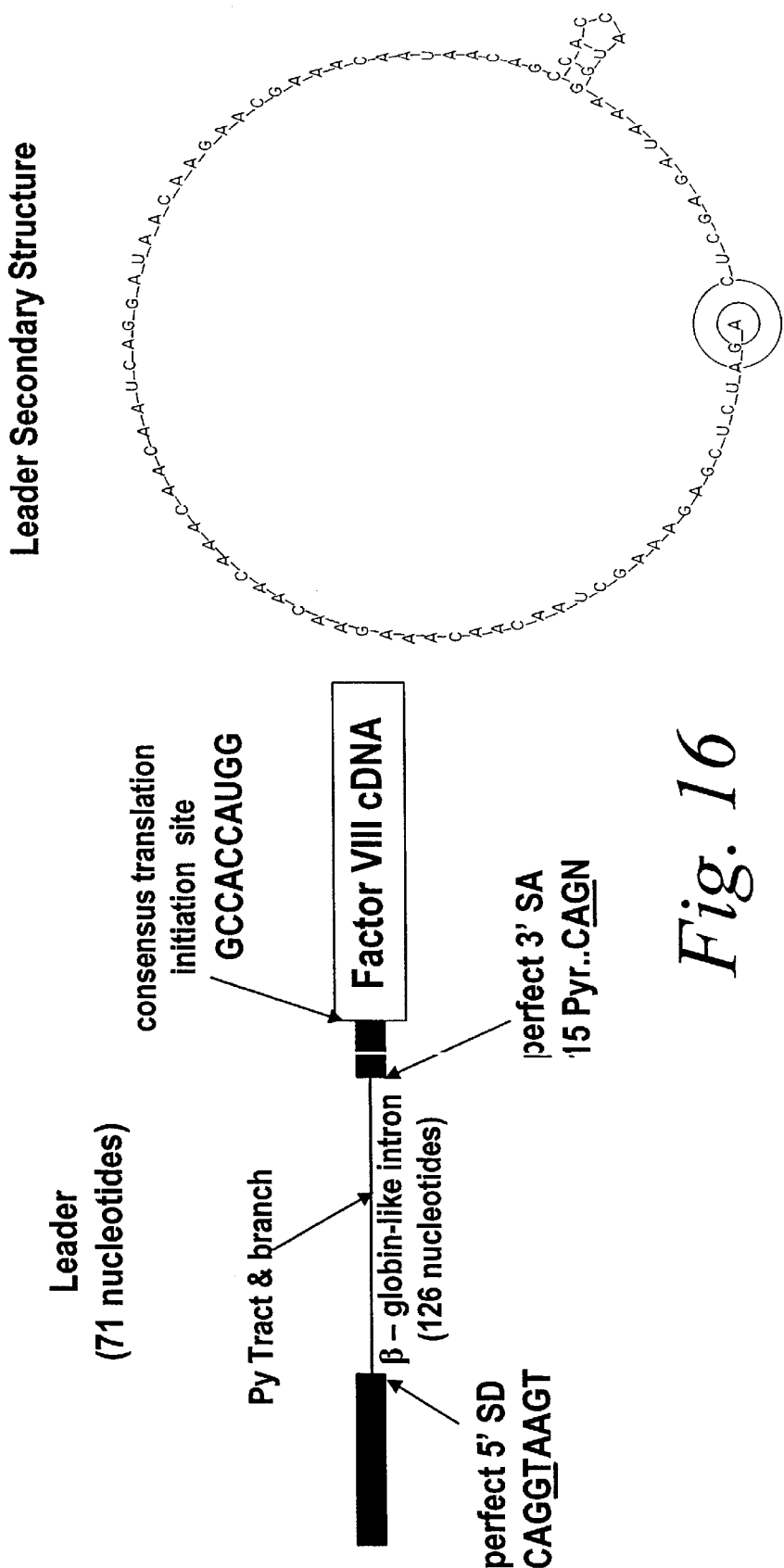
FIG. 16 shows the optimized intron-split leader sequence within vectors pCY-2, pCY-6, PLZ-6 and pCY2-SRE5, as well as the secondary structure of the leader sequence (SEQ ID NO:11) predicted by the computer program RNAdraw™.

In cases where the intron does not contain consensus 5' splice donor and 3' splice acceptor sites, or a consensus branch and pyrimidine track sequence, the intron is preferably optimized (modified) to render these sites completely consensus. This can be achieved, for example, by substituting one or more nucleotides within the 5' or 3' splice site, as previously described herein to render the site consensus. For example, when using the rabbit β-globin intron, the nucleotide sequence can be modified as shown in FIG. 16 to render the 5' splice donor and 3' splice acceptor sites, and the pyrimidine track, entirely consensus. This can facilitate efficient transcription and export of the gene message out of the cell nucleus, thereby increasing expression. Exemplary nucleotide substitutions within the rabbit β-globin IVS which can be made to achieve this result are shown in FIG. 23 which shows a comparison of the sequence for the unmodified (wild-type) rabbit β-globin intron (SEQ ID NO:6) and the same sequence modified to render the 5' splice donor and 3' splice acceptor sites, and the pyrimidine track, entirely consensus (SEQ ID NO:7).

Figure 22:
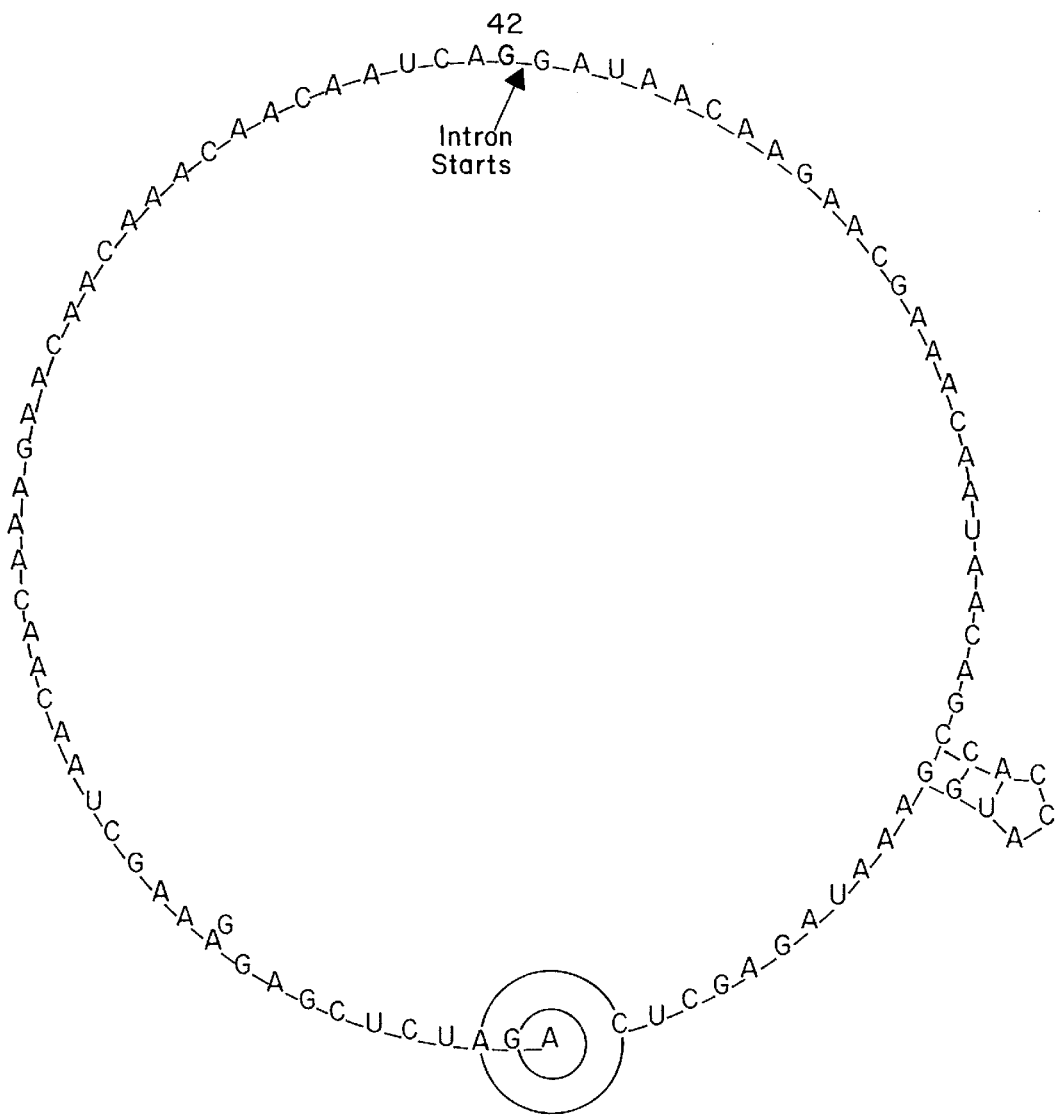
FIG. 22 shows the nucleotide sequence and secondary structure of an optimized leader sequence.

When engineering one or more introns into the 5' UTR of a gene construct, the intron can be inserted into the leader sequence of the gene, as shown in FIGS. 15, 16 and 22. Accordingly, the intron can be inserted within the leader sequence, downstream from the promoter and enhancer elements. This can be done in conjunction with one or more additional modifications to the leader sequence, all of which serve to increase transcription, stability and export of mRNAs. Such additional modifications include, for example, optimizing the translation initiation site (Kozak et al. (1986) Cell 44:283) and/or the secondary structure of the leader sequence (Kozak et al. (1994) Molec. Biol. 235:95).

Accordingly, in a preferred embodiment, the invention provides a gene construct which contains within its transcriptional unit, one or a combination of the foregoing genetic elements and sequence modifications designed to provide high levels and duration of gene expression, optionally in a tissue-specific manner. In a particular embodiment, the construct contains a gene encoding human Factor VIII (e.g., β-domain deleted or full-length), having a 5' untranslated region which is optimized to provide significant levels and duration of liver-specific or endothelium-specific expression.

Particularly preferred gene constructs of the invention include, for example, those comprising the nucleotide sequences shown in SEQ ID NO:2 and SEQ ID NO:4, referred to herein respectively as pCY-2 and pLZ-6. These constructs contain the coding sequences for human β-domain deleted Factor VIII (pCY-2) and full-length human Factor VIII (containing an intron spanning the β-domain) (pLZ-6) downstream from an optimized 5' UTR designed to provide high levels and duration of human Factor VIII expression in liver cells. Other preferred gene constructs comprise the identical 5' UTR of pCY-2 and pLZ-6, in conjunction with coding sequences for other proteins desired to be expressed in the liver (e.g., other blood coagulation factors, such as human Factor IX).

As shown in FIGS. 7, 15 and 16, plasmids pCY-2 and pLZ-6 contain 5' UTRs comprising a novel combination of regulatory elements and sequence modifications shown herein to provide high levels and duration of human Factor VIII expression, both in vitro and in vivo, in liver cells. Specifically, each construct comprises within its 5' UTR sequentially from 5' to 3' (a) two copies of the ABP enhancer (SEQ ID NO:9), (b) one copy of the TBG promoter (SEQ ID NO:10), and (c) an optimized 71 nucleotide leader sequence (SEQ ID NO: 11) split by intron 1 of the rabbit β-globin gene. The intron is optimized to contain consensus splice acceptor, donor and pyrimidine track sites.

The leader sequence within the 5' UTR of pCY-2 and pLZ-6 also contains an optimized translation initiation site (SEQ ID NO: 8). Specifically, the human Factor VIII gene contains a cytosine at the +4 position, following the AUG start codon. This base was changed to a guanine, resulting in an amino acid change within the signal sequence of the protein from a glutamine to a glutamic acid. The leader sequence was further designed to have no RNA secondary structure, as predetermined by an RNA-folding algorithm (FIG. 16) (Kozak et al. (1994) J. Mol. Biol. 235:95).

In addition to optimization of the 5' UTR of a gene construct, the 3' UTR can also be engineered to include one or more genetic elements or sequence modifications which increase and/or prolong expression of the gene. For example, the 3' UTR can be modified to provide optimal RNA processing, export and mRNA stability. In one embodiment of the invention, this is done by increasing translational termination efficiency. In mammalian RNA's, translational termination is generally optimal if the base following the stop codon is a purine (McCaughan et al. (1995) PNAS 92:5431). In the case of the human Factor VIII gene, the UGA stop codon is followed by a guanine and is thus already optimal. However, in other gene constructs of the invention which do not naturally contain an optimized translational termination sequence, the termination sequence can be optimized using, for example, site directed mutagenesis, to substitute the base following the stop codon for a purine.

In particular gene constructs of the invention which contain the human Factor VIII gene, the 3' UTR can further be modified to remove one or more of the three pentamer sequences AUUUA present in the 3' UTR of the gene. This can increase the stability of the message. Alternatively, the 3' UTR of the human Factor VIII gene, or any gene having a short-lived messenger RNA, can be switched with the 3' UTR of a gene associated with a message having a longer lifespan.

Additional modifications for optimizing gene constructs of the invention include insertion of one or more poly A trimer cassettes for optimal polyadenylation and 3' end formation. These can be inserted within the 5' UTR or the 3' UTR of the gene. In a preferred embodiment, the gene construct is flanked on either side by a poly A trimer cassette, as shown in FIG. 15. These cassettes can inhibit transcription originating outside of the desired promoter in the transcriptional unit, ensuring that transcription of the gene occurs only in the tissue where the promoter is active (Maxwell et al. (1989) Biotechniques 1989 3:276). Additionally, because the poly A trimer cassette functions in both orientations, i.e., on each DNA strand, it can be utilized at the 3' end of the gene for transcriptional termination and polyadenylation, as well as to inhibit bottom strand transcription and production of antisense RNA.

Figure 17:
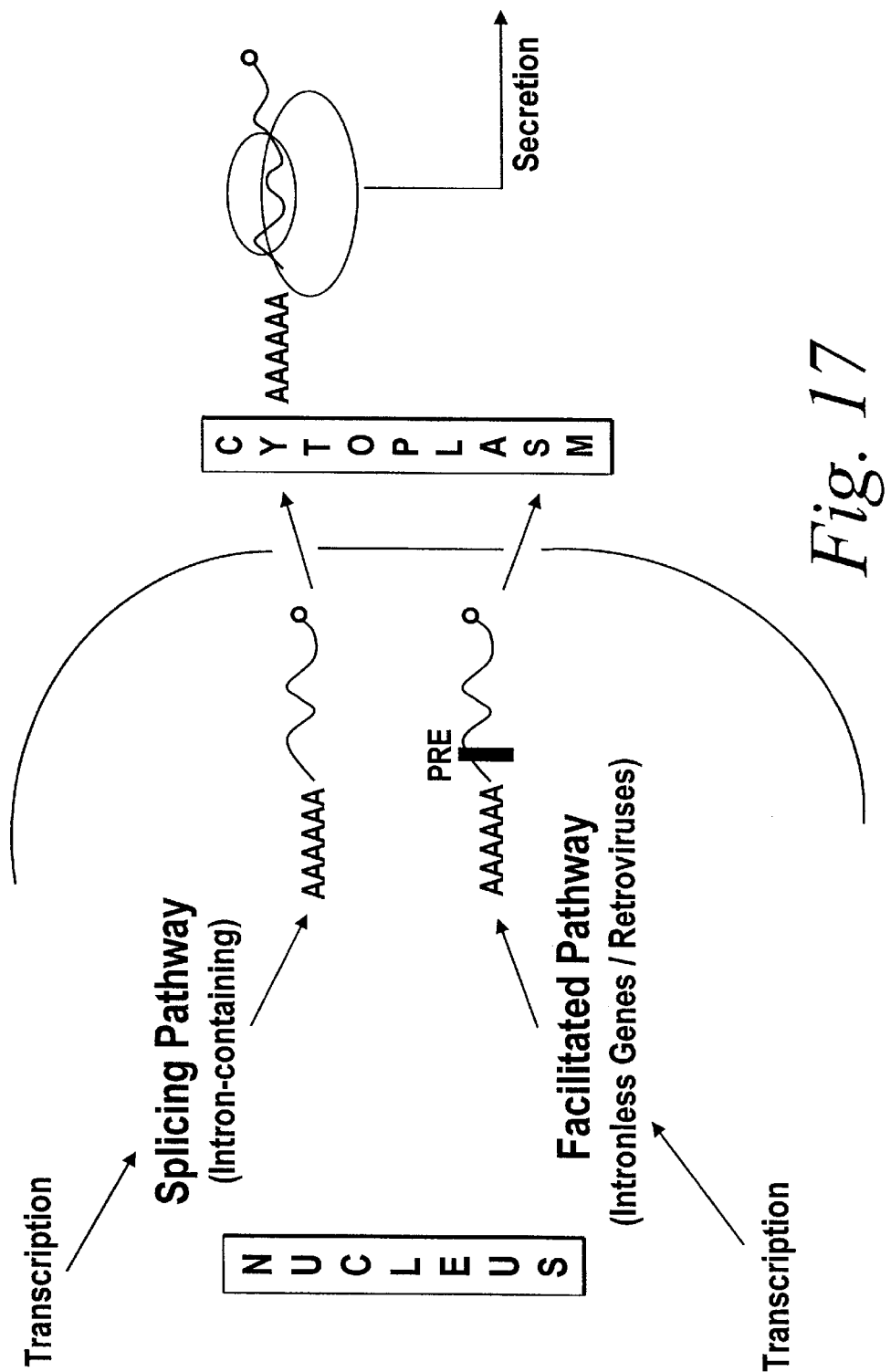
FIG. 17 is a schematic illustration showing two different RNA export pathways. The majority of mRNA's in higher eukaryotes contain intronic sequences which are removed within the nucleus (splicing pathway), follwed by export of the mRNA into the cytoplasm. Mammalian intronless genes, hepadnaviruses (e.g., HBV), and many retroviruses access a nonsplicing pathway which is facilitated by cellular RNA export proteins (facilitated pathway).

In further embodiments of the invention, gene optimization includes the addition of viral elements for accessing non-splicing RNA export pathways. The majority of mRNAs in higher eukaryotes contain intronic sequences which are removed within the nucleus, followed by export of the mRNA into the cytoplasm. This is referred to as the splicing pathway. However, as shown in FIG. 17, mammalian intronless genes, hepadnaviruses (e.g., HBV), and many retroviruses access a nonsplicing pathway which is facilitated by cellular RNA export proteins and/or specific sequences within. This is referred to as the facilitated pathway.

Figure 18:
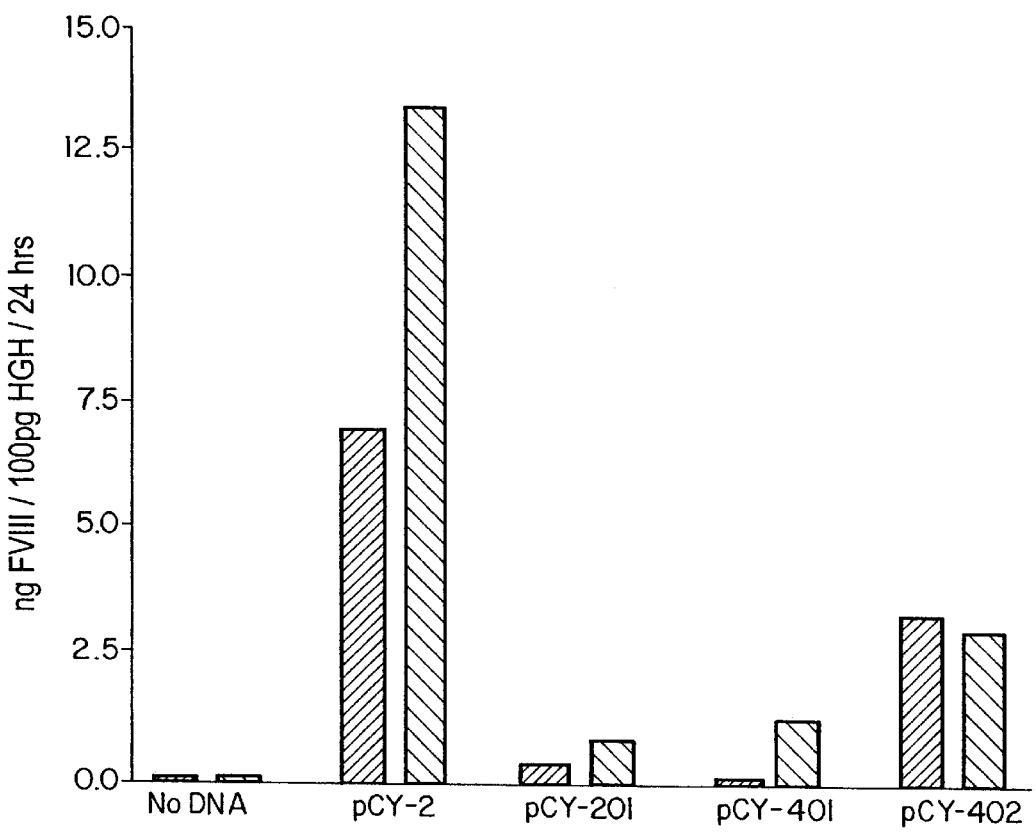
FIG. 18 is a graph showing the effect of a 5' intron and 3' post-transcriptional regulatory element (PRE) on human Factor VIII expression levels in HuH-7 cells. Plasmid pCY-2 contains a 5' intron but no PRE. Plasmid pCY-201 is identical to pCY-2, except that it lacks the 5' intron. Plasmid pCY-401 and pCY-402 are identical to pCY-201, except that they contain one and two copies of the PRE, respectively. The levels of secreted active Factor VIII was measured from supernatants collected 48 hours (first bar of each group) or 72 hours (second bar of each group) after transfection by Coatest VIII: c/4 kit from Kabi Inc. The transfection efficiency of each plasmid was normalized by analysis of human growth hormone secreted levels.

In a particular embodiment, the gene construct is modified to include one or more copies of the post-transcriptional regulatory element (PRE) from hepatitis B virus. This 587 base pair element and its function to facilitate export of mRNAs from the nucleus, is described in U.S. Pat. No. 5,744,326. Generally, the PRE element is placed within the 3' UTR of the gene, and can be inserted as two or more copies to further increase expression, as shown in FIG. 18 (plasmid pCY-401 verses plasmid pCY-402).

Gene constructs (e.g., expression vectors) of the invention can still further include sequence elements which impart both an autonomous replication activity (i.e., so that when the cell replicates, the plasmid replicates as well) and nuclear retention as an episome. Generally, these sequence elements are included outside of the transcriptional unit of the gene construct. Suitable sequences include those functional in mammalian cells, such as the oriP sequence and EBNA-1 gene from the Epstein-Barr virus (Yates et al. (1985) Nature 313:812). Other suitable sequences include the E. coli origen of replication, as shown in FIGS. 6 and 7.

Gene constructs of the invention, such as pDJC, pCY-2, pCY-6, pLZ-6 and pCY2-SE5, have been described above, but are not intended to be limiting. Other novel constructs can be made in accordance with the guidelines provided herein, and are intended to be included within the scope of the present invention.

Increased Cytoplasmic RNA Accumulation and Expression

Novel DNAs (e.g., genes) of the present invention are modified to increase expression, for example, by facilitate cytoplasmic accumulation of mRNA transcribed from the DNA and by optimizing the 5' and 3' untranslated regions of the DNA. Accordingly, cytoplasmic mRNA accumulation and/or expression of the DNA is increased relative to the same DNA in unmodified form.

To evaluate (e.g., quantify) levels of nuclear or cytoplasmic mRNA accumulation obtained following transcription of novel DNAs and vectors of the invention, a variety of art recognized techniques can be employed, such as those described in Sambrook et al. "Molecular Cloning," 2d ed., and in the examples below. Such techniques include, for instance, Northern blot analysis, using total nuclear or cytoplasmic RNA. This assay can, optionally, be normalized using mRNA transcribed from a control gene, such as a gene encoding glyceraldehyde phosphate dehydrogenase (GAPDH). Levels of nuclear and cytoplasmic RNA accumulation can then be compared for novel DNAs of the invention to determine whether an increase has occurred following correction of one or more consensus or near consensus splice sites, and/or by addition of one or more non-naturally occurring introns into the DNA.

Novel DNAs of the invention can also be assayed for altered splicing patterns using similar techniques. For example, as described in the examples below, to determine whether a non-naturally occurring intron has been successfully incorporated into a DNA so that it is correctly spliced during mRNA processing, cytoplasmic mRNA can be assayed by Northern blot analysis, reverse transcriptase PCR (RT-PCR), or RNase protection assays. Such assays are used to determine the size of the mRNA produced from the novel DNA containing the non-naturally occurring intron. The size of the mRNA can then be compared to the size of the DNA with and without the intron to determine whether splicing has been achieved, and whether the splicing pattern corresponds to that expected based on the size of the added intron.

Alternatively, protein expressed from cytoplasmic RNA can be assayed by SDS-PAGE analysis and sequenced to confirm that correct splicing has been achieved.

To measure expression levels, novel DNAs of the invention can also be tested in a variety of art-recognized expression assays. Suitable expression assays, as illustrated in the examples provided below, include quantitative ELISA (Zatloukal et al. (1994) PNAS 91: 5148–5152), radioimmunoassay (RIA), and enzyme activity assays. When expression of Factor VIII protein is being measured, in particular, Factor VIII activity assays such as the KabiCoATest, (Kabi Inc., Sweden) can be employed to quantify expression.

Gene Delivery to Cells

Following insertion into an appropriate vector, novel DNAs of the invention can be delivered to cells either in vitro or in vivo. For example, the DNA can be transfected into cells in vitro using standard transfection techniques, such as calcium phosphate precipitation (O'Mahoney et al. (1994) DNA & Cell Biol. 13(12): 1227–1232). Alternatively, the gene can be delivered to cells in vivo by, for example, intravenous or intramuscular injection.

In one embodiment of the invention, the gene is targeted for delivery to a specific cell by linking the plasmid to a carrier molecule containing a ligand which binds to a component on the surface of a cell, thereby forming a polynucleotide-carrier complex. The carrier can further comprise a nucleic acid binding agent which noncovalently mediates linkage of the DNA to the ligand of the carrier molecule.

The carrier molecule of the polynucleotide-carrier complex performs at least two functions: (1) it binds the polynucleotide (e.g., the plasmid) in a manner which is sufficiently stable (either in vivo, ex vivo, or in vitro) to prevent significant uncoupling of the polynucleotide extracellularly prior to internalization by a target cell, and (2) it binds to a component on the surface of a target cell so that the polynucleotide-carrier complex is internalized by the cell. Generally, the carrier is made up of a cell-specific ligand and a cationic moiety which, for example are conjugated. The cell-specific ligand binds to a cell surface component, such as a protein, polypeptide, carbohydrate, lipid or combination thereof. It typically binds to a cell surface receptor. The cationic moiety binds, e.g., electrostatically, to the polynucleotide.

The ligand of the carrier molecule can be any natural or synthetic ligand which binds a cell surface receptor. The ligand can be a protein, polypeptide, glycoprotein, glycopeptide, glycolipid or synthetic carbohydrate which has functional groups that are exposed sufficiently to be recognized by the cell surface component. It can also be a component of a biological organism such as a virus, cells (e.g., mammalian, bacterial, protozoan).

Alternatively, the ligand can comprise an antibody, antibody fragment (e.g., an F(ab')$_2$ fragment) or analogues thereof (e.g., single chain antibodies) which binds the cell surface component (see e.g., Chen et al. (1994) FEBS Letters 338:167–169, Ferkol et al. (1993) J. Clin. Invest. 92:2394–2400, and Rojanasakul et al. (1994) Pharmaceutical Res. 11(12):1731–1736). Such antibodies can be produced by standard procedures.

Ligands useful in forming the carrier will vary according to the particular cell to be targeted. For targeting hepatocytes, proteins, polypeptides and synthetic compounds containing galactose-terminal carbohydrates, such as carbohydrate trees obtained from natural glycoproteins or chemically synthesized, can be used. For example, natural glycoproteins that either contain terminal galactose residues or can be enzymatically treated to expose terminal galactose residues (e.g., by chemical or enzymatic desialylation) can be used. In one embodiment, the ligand is an asialoglycoprotein, such as asialoorosomucoid, asialofetuin or desialylated vesicular stomatitis virus. In another embodiment, the ligand is a tri- or tetra-antennary carbohydrate moiety.

Alternatively, suitable ligands for targeting hepatocytes can be prepared by chemically coupling galactose-terminal carbohydrates (e.g., galactose, mannose, lactose, arabinogalactan etc.) to nongalactose-bearing proteins or polypeptides (e.g., polycations) by, for example, reductive lactosamination. Methods of forming a broad variety of other synthetic glycoproteins having exposed terminal galactose residues, all of which can be used to target hepatocytes, are described, for example, by Chen et al. (1994) *Human Gene Therapy* 5:429–435 and Ferkol et al. (1993) *FASEB* 7: 1081–1091 (galactosylation of polycationic histones and albumins using EDC); Perales et al. (1994) *PNAS* 91:4086–4090 and Midoux et al. (1993) *Nucleic Acids Research* 21(4):871–878 (lactosylation and galactosylation of polylysine using α-D-galactopyranosyl phenylisothiocyanate and 4-isothiocyanatophenyl β-D-lactoside); Martinez-Fong (1994) *Hepatology* 20(6):1602–1608 (lactosylation of polylysine using sodium cyanoborohydride and preparation of asialofetuin-polylysine conjugates using SPDP); and Plank et al. (1992) *Bioconjugate Chem.* 3:533–539 (reductive coupling of four terminal galactose residues to a synthetic carrier peptide, followed by linking the carrier to polylysine using SPDP).

For targeting the polynucleotide-carrier complex to other cell surface receptors, the carrier component of the complex can comprise other types of ligands. For example, mannose can be used to target macrophages (lymphoma) and Kupffer cells, mannose 6-phosphate glycoproteins can be used to target fibroblasts (fibro- sarcoma), intrinsic factor-vitamin B12 and bile acids (See Kramer et al. (1992) *J. Biol. Chem.* 267:18598–18604) can be used to target enterocytes, insulin can be used to target fat cells and muscle cells (see e.g., Rosenkranz et al. (1992) *Experimental Cell Research* 199:323–329 and Huckett et al. (1990) *Chemical Pharmacology* 40(2):253–263), transferrin can be used to target smooth muscle cells (see e.g., Wagner et al. (1990) *PNAS* 87:3410–3414 and U.S. Pat. No. 5, 354,844 (Beug et al.)), Apolipoprotein E can be used to target nerve cells, and pulmonary surfactants, such as Protein A, can be used to target epithelial cells (see e.g., Ross et al. (1995) *Human Gene Therapy* 6:31–40).

The cationic moiety of the carrier molecule can be any positively charged species capable of electrostatically binding to negatively charged polynucleotides. Preferred cationic moieties for use in the carrier are polycations, such as polylysine (e.g., poly-L-lysine), polyarginine, polyomithine, spermine, basic proteins such as histones (Chen et al., supra.), avidin, protamines (see e.g., Wagner et al., supra.), modified albumin (i.e., N-acylurea albumin) (see e.g., Huckett et al., supra.) and polyamidoamine cascade polymers (see e.g., Haensler et al. (1993) *Bioconjugate Chem.* 4: 372–379). A preferred polycation is polylysine (e.g., ranging from 3,800 to 60,000 daltons). Other preferred cationic moieties for use in the carrier are cationic liposomes.

In one embodiment, the carrier comprises polylysine having a molecular weight of about 17,000 daltons (purchased as the hydrogen bromide salt having a MW of a 26,000 daltons), corresponding to a chain length of approximately 100–120 lysine residues. In another embodiment, the carrier comprises a polycation having a molecular weight of about 2,600 daltons (purchased as the hydrogen bromide salt having a MW of a 4,000 daltons), corresponding to a chain length of approximately 15–10 lysine residues.

The carrier can be formed by linking a cationic moiety and a cell-specific ligand using standard cross-linking reagents which are well known in the art. The linkage is typically covalent. A preferred linkage is a peptide bond. This can be formed with a water soluble carbodiimide, such as 1-ethyl-3-(3-dimethylaminopropyl)carbodiimide hydrochloride (EDC), as described by McKee et al (1994) *Bioconjugate Chem.* 5: 306–311 or Jung, G. et al. (1981) *Biochem. Biophys. Res. Commun.* 101: 599–606 or Grabarek et al. (1990) *Anal. Biochem.* 185:131. Alternative linkages are disulfide bonds which can be formed using cross-linking reagents, such as N-Succinimidyl 3-(2-pyridyldithio) propionate (SPDP), N-hydroxysuccinimidyl ester of chlorambucil, N-Succinimidyl-(4-Iodoacetyl) aminobenzoate) (SIAB), Sulfo-SIAB, and Sulfo-succinimidyl-4-maleimidophenyl-butyrate (Sulfo-SMPB). Strong noncovalent linkages, such as avidin-biotin interactions, can also be used to link cationic moieties to a variety of cell binding agents to form suitable carrier molecules.

The linkage reaction can be optimized for the particular cationic moiety and cell binding agent used to form the carrier. The optimal ratio (w:w) of cationic moiety to cell binding agent can be determined empirically. This ratio will vary with the size of the cationic moiety (e.g., polycation) being used in the carrier, and with the size of the polynucleotide to be complexed. However, this ratio generally ranges from about 0.2–5.0 (cationic moiety: ligand). Uncoupled components and aggregates can be separated from the carrier by molecular sieve or ion exchange chromatography (e.g., Aquapore™ cation exchange, Rainin).

In one embodiment of the invention, a carrier made up of a conjugate of asialoorosomucoid and polylysine is formed with the cross linking agent 1-(3-dimethylaminopropyl)-3-ethyl carbodiimide. After dialysis, the conjugate can be separated from unconjugated components by preparative acid-urea polyacrylamide gel electrophoresis (pH 4–5).

Following formation of the carrier molecule, the polynucleotide (e.g., plasmid) is linked to the carrier so that (a) the polynucleotide is sufficiently stable (either in vivo, ex vivo, or in vitro) to prevent significant uncoupling of the polynucleotide extracellularly prior to internalization by the target cell, (b) the polynucleotide is released in functional form under appropriate conditions within the cell, (c) the polynucleotide is not damaged and (d) the carrier retains its capacity to bind to cells. Generally, the linkage between the carrier and the polynucleotide is noncovalent. Appropriate noncovalent bonds include, for example, electrostatic bonds, hydrogen bonds, hydrophobic bonds, anti-polynucleotide antibody binding, linkages mediated by intercalating agents, and streptavidin or avidin binding to polynucleotide-containing biotinylated nucleotides. However, the carrier can also be directly (e.g., covalently) linked to the polynucleotide using, for example, chemical cross-linking agents (e.g., as described in WO-A-91/04753 (Cetus Corp.), entitled "Conjugates of Antisense Oligonucleotides and Therapeutic Uses Thereof").

As described in Example 4, polynucleotide-carrier complexes can be formed by combining a solution containing carrier molecules with a solution containing a polynucleotide to be complexed, preferably so that the resulting composition is isotonic (see Example 4).

Administration

Novel DNAs of the invention can be administered to cells either in vitro or in vivo for transcription and/or expression therein.

For in vitro delivery, cultured cells can be incubated with the DNA in an appropriate medium under suitable transfection conditions, as is well known in the art.

For in vivo delivery (e.g., in methods of gene therapy) DNAs of the invention (preferably contained within a suitable expression vector) can be administered to a subject in a pharmaceutically acceptable carrier. The term "pharmaceutically acceptable carrier", as used herein, is intended to include any physiologically acceptable vehicle for stabilizing DNAs of the present invention for administration in vivo, including, for example, saline and aqueous buffer solutions, solvents, dispersion media, antibacterial and antifungal agents, isotonic and absorption delaying agents, and the like. The use of such media and agents for pharmaceutically active substances is well known in the art. Except insofar as any conventional media is incompatible with the polynucleotide-carrier complexes of the present invention, use thereof in a therapeutic composition is contemplated.

Accordingly, novel DNAs of the invention can be combined with pharmaceutically acceptable carriers to form a pharmaceutical composition. In all cases, the pharmaceutical composition must be sterile and must be fluid to the extent that easy syringability exists. It must be stable under the conditions of manufacture and storage and must be preserved against the contaminating action or microorganisms such as bacteria and fungi. Protection of the polynucleotide-carrier complexes from degradative enzymes (e.g., nucleases) can be achieved by including in the composition a protective coating or nuclease inhibitor. Prevention of the action of microorganisms can be achieved by various anti-bacterial and anti-fungal agents, for example, parabens, chlorobutanol, phenol, ascorbic acid, thimerosal, and the like.

Novel DNAs of the invention may be administered in vivo by any suitable route of administration. The appropriate dosage may vary according to the selected route of administration. The DNAs are preferably injected intravenously in solution containing a pharmaceutically acceptable carrier, as defined herein. Sterile injectable solutions can be prepared by incorporating the DNA in the required amount in an appropriate buffer with one or a combination of ingredients enumerated above or below, followed by filtered sterilization. Other suitable routes of administration include intravascular, subcutaneous (including slow-release implants), topical and oral.

Appropriate dosages may be determined empirically, as is routinely practiced in the art. For example, mice can be administered dosages of up to 1.0 mg of DNA per 20 g of mouse, or about 1.0 mL of DNA in solution per 1.4 mL of mouse blood.

Administration of a novel DNA, or protein expressed therefrom, to a subject can be in any pharmacological form including a therapeutically active amount of DNA or protein, in combination with another therapeutic molecule. Administration of a therapeutically active amount of a pharmaceutical composition of the present invention is defined as an amount effective, at dosages and for periods of time necessary to achieve the desired result (e.g., an improvement in clinical symptoms). A therapeutically active amount of DNA or protein may vary according to factors such as the disease state, age, sex, and weight of the individual. Dosage regimens may be adjusted to provide the optimum therapeutic response. For example, several divided doses may be administered daily or the dose may be proportionally reduced as indicated by the exigencies of the therapeutic situation.

USES

Novel DNAs of the present invention can be used to efficiently express a desired protein within a cell. Accordingly, such DNAs can be used in any context in which gene transcription and/or expression is desired.

In one embodiment, the DNA is used in a method of gene therapy to treat a clinical disorder. In another embodiment, the DNA is used in antisense therapy to produce sufficient levels of nuclear and/or cytoplasmic mRNA to inhibit expression of a gene. In another embodiment, the DNA is used to study RNA processing and/or gene regulation in vitro or in vivo. In another embodiment, the DNA is used to produce therapeutic or diagnostic proteins which can then be administered to patients as exogenous proteins.

Methods for increasing levels of cytoplasmic RNA accumulation and gene expression provided by the present invention can also be used for any and all of the foregoing purposes.

In a preferred embodiment, the invention provides a method if increasing expression of a gene encoding human Factor VIII. Accordingly, the invention also provides an improved method of human Factor VIII gene therapy involving administering to a patient afflicted with a disease characterized by a deficiency in Factor VIII a novel Factor VIII gene in an amount sufficient to treat the disease.

In addition, the present invention provides a novel method for altering the transcription pattern of a DNA. By correcting one or more consensus or near consensus splice sites within the DNA, or by adding one or more introns to the DNA, the natural splicing pattern of the DNA will be modified and, at the same time, expression may be increased. Accordingly, methods of the invention can be used to tailor the transcription of a DNA so that a greater amount of a particular desired RNA species is transcribed and ultimately expressed, relative to other RNA species transcribed from the DNA (i.e., alternatively spliced RNAs).

Methods of the invention can also be used to modify the coding sequence of a given DNA, so that the structure of the protein expressed from the DNA is altered in a beneficial manner. For example, introns can be added to the DNA so that portions of the gene will be removed during transcription and, thus, not be expressed. Preferred gene portions for removal in this manner include those encoding, e.g., antigenic regions of a protein and/or regions not required for activity. Alternatively or additionally, consensus or near consensus splice sites can be corrected within the DNA so that previously recognizable (i.e., operable) introns and exons are no longer recognized by a cells splicing machinery. This alters the coding sequence of the mRNA ultimately transcribed from the DNA, and can also facilitate its export from the nucleus to the cytoplasm where it can be expressed.

This invention is illustrated further by the following examples which should not be construed as further limiting the subject invention. The contents of all references and published patent applications cited throughout this application are hereby incorporated by reference.

EXAMPLES

Example 1

Construction of a Human Factor VIII Gene Containing an Intron Spanning the β-Domain A full-length human Factor VIII cDNA containing an intron spanning the section of the cDNA encoding amino acids 745–1638 (FIG. 11) was constructed as described below. Amino acid numbering was designated starting with Met-i of the mature human Factor VIII protein and, thus, does not include the 19 amino acid signal peptide of the protein. The β-domain region of a human Factor VIII protein is made up of 983 amino acids (Vehar et al. (1984) *Nature*

312: 337–342). Thus, the region of the cDNA spliced out during pre-mRNA processing corresponds to about 89% of the β-domain.

To select suitable sites for inserting the 5' splice donor (SD) and 3' splice acceptor (SA) sites, the sequence of the full-length Factor VIII cDNA expression plasmid pCY-6 (SEQ ID NO:4) was scanned for convenient restriction enzyme sites. Restriction sites were selected according to the following criteria: (a) they flanked and were in close proximity to the sites into which the splicing signals were to be introduced, so that any PCR fragment generated to fill in the region between these sites would have as little chance as possible for undesired point mutations introduced by the process of PCR; (b) they would cut the expression plasmid in as few places as possible, preferably only at the site flanking the region of splice site introduction.

The restriction sites chosen according to these criteria for cloning in the splice donor site were: Kpn I (base 2816 of the coding sequence of pCY-6, or base 3822 of the complete nucleotide sequence of pCY-6 provided in SEQ ID NO:4, since the first 1005 bases of this plasmid are non-coding bases), and Tth 1111 (base 3449 of the coding sequence of pCY-6, or base 4455 of the complete nucleotide sequence of pCY-6 shown in SEQ ID NO:4). The restriction sites chosen according to these criteria for cloning in the splice acceptor site were: Bcl I (bases 1407 and 5424 of the coding sequence of pCY-6, or bases 2413 and 6430 of the complete nucleotide sequence of pCY-6 shown in SEQ ID NO:4) and BspE 1 (base 7228 of the coding sequence of pCY-6, or base 8234 of the complete nucleotide sequence of pCY-6 shown in SEQ ID NO:4).

Generation of Splice Donor Site

A fragment containing the region of Factor VIII cDNA from the Kpn I site to the Tth 111 I site, with the above described splice donor sequence inserted at the appropriate spot, was then generated in the following manner:

A. PCR primers were designed, such that the top strand upstream primer (Fragment A top) would prime at the Kpn I site of full-length Factor VIII cDNA (FIG. 12), and the bottom strand downstream primer (Fragment A bottom) would prime at the site of insertion for the 5' splice donor. The bottom strand primer also contained the insertion sequence. These primers were used in a PCR reaction with pCIS-F8 (full-length Factor VIII cDNA expression plasmid) as template to yield "Fragment A," which contains the sequence spanning the region of Factor VIII cDNA from Kpn I to the splice donor insertion site, located at the 3' end of the fragment.

B. In similar fashion, "Fragment B" was generated using primer "Fragment B top," which contains the insertion sequence, and would prime at the insertion site of full-length Factor VIII cDNA, and primer "Fragment B bottom," which would prime at the Tth 111 I site of full-length Factor VIII cDNA. "Fragment B" contains the sequence spanning the region of Factor VIII cDNA from the splice donor insertion site to rTth111 I. The 5' splice donor insertion sequence was located at the 5' end of the fragment.

C. Fragments A and B were run on a horizontal agarose gel, excised, and extracted, in order to purify them away from unincorporated nucleotides and primers.

D. These fragments were then combined in a PCR reaction using as primers "Fragment A top" and "Fragment B bottom." The regions at the 3' end of Fragment A and the 5' end of Fragment B overlapped because they were identical, and the final product of this reaction was a PCR fragment spanning the Factor VIII cDNA from Kpn I to Tth111 I, and containing the engineered splice donor at the insertion site, i.e., near the beginning of the coding region of the β-domain of Factor VIII. This fragment was designated "Fragment AB."

E. Fragment AB (an overlap PCR product) was cloned into the EcoR V site of pBluescript II SK(+) to yield clone pBS-SD (FIG. 9), and the sequence of the insertion was then confirmed.

Generation of Splice Acceptor Site

A fragment containing the region of Factor VIII cDNA from the second Bcl I site to the BspE I site, with the above described splice acceptor sequence inserted at the appropriate spot, was generated in the following manner:

A. PCR primers were designed, such that the top strand upstream primer (Primer A) would prime at the second Bcl I site, and the bottom strand downstream primer (Primer B2) would prime at the insertion site for the 3' splice acceptor. The bottom strand primer also contained the restriction sites Mun I and BspE I. These primers were used in a PCR reaction with pCIS-F8 as template to yield "Fragment I," which contains the sequence spanning the region of Factor VIII cDNA from the Bcl I site to the insertion site, with the Mun I and BspE I sites located at the 3' end of the fragment.

B. In a similar fashion, "Fragment III" was generated using "Primer G3" which contains the restriction site BstE II, the splice acceptor recognition sequence (polypyrimidine tract followed by "CAG"), and primes at the insertion site for the splice acceptor; and "Primer H," which would prime the bottom strand at the BspE I site, so that the resulting fragment would contain the restriction site BstE II, the splice acceptor recognition site and sequence spanning the region of Factor VIII cDNA from the insertion site to BspE I.

C. "Fragment II," which contained the branch signals and IVS 14 sequence, was generated by designing four oligos (C2, D, E, and F3), two top and two bottom, which, when combined, would overlap each other by 21 to 22 bases, and when filled in and amplified under PCR conditions, would generate a fragment containing a Mun I site, 130 bases of the aforementioned IVS 14 sequence (including the 2 branch sequences at the 5' end of the 130 bases), and the cloning sites BstE II and BspE I. In addition, two small primers (CX and FX2) were designed that would prime at the very ends of the expected fragment, in order to increase amplification of full-length PCR product. All oligonucleotide primers were combined in a single PCR reaction, and the desired fragment was generated.

D. All three fragments were cloned into the EcoR V site of pBluescript II SK(+), and their sequences were then confirmed.

Figure 9:
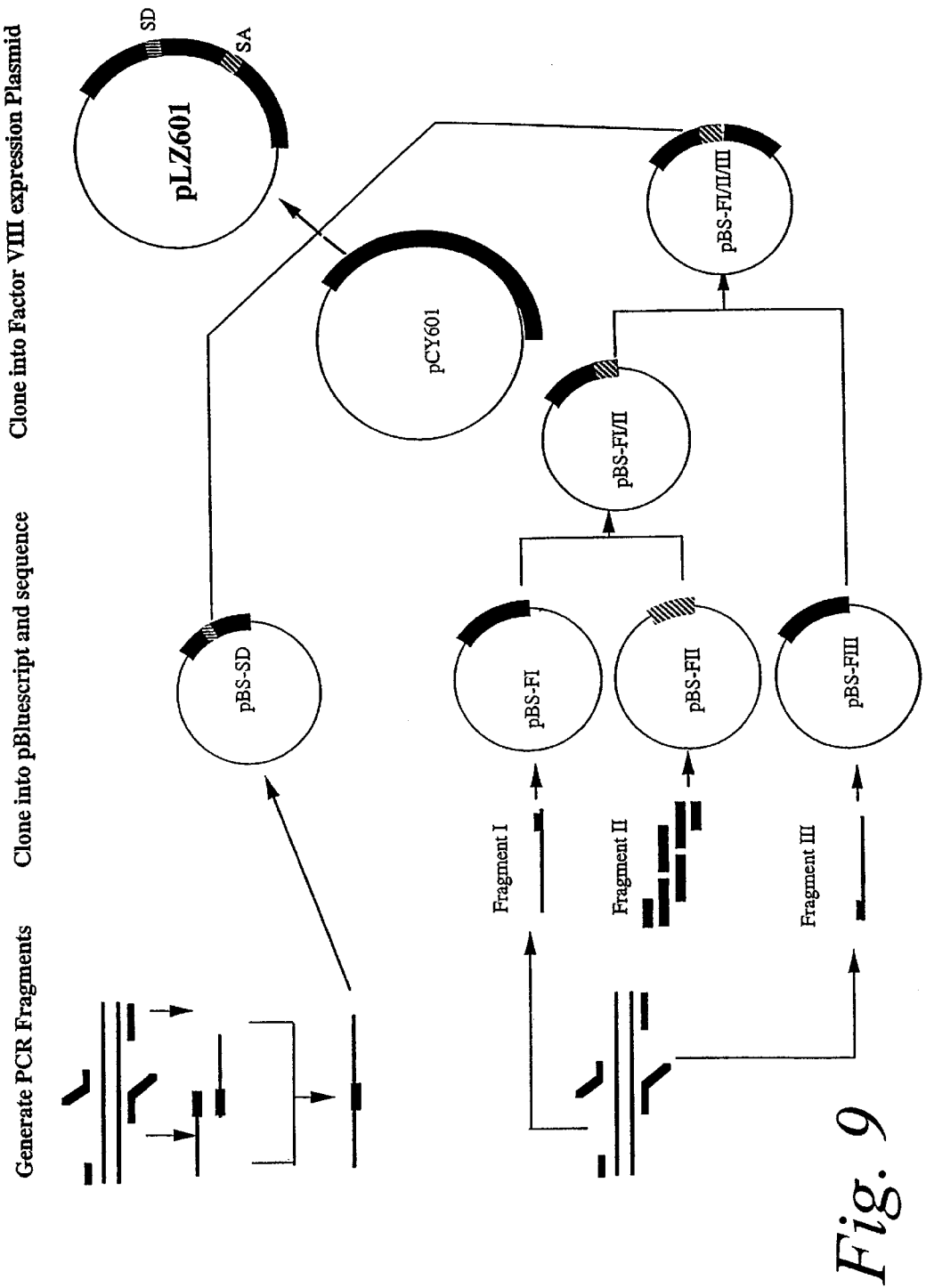
FIG. 9 is a schematic illustration of the cloning procedure used to insert an engineered intron into the coding region of the human Factor VIII cDNA, spanning a majority of the region of the cDNA encoding the β-domain. PCR fragments were generated containing nucleotide sequences necessary to create consensus 5' splice donor and 3' splice acceptor sites when cloned into selected positions flanking the β-domain coding sequence. The fragments were then cloned into plasmid pBluescript and sequenced. Once sequences had been confirmed, the fragments creating the 5' splice donor (SD) site were cloned into plasmid pCY-601 and pCY-6 (containing the full-length human Factor VIII cDNA coding region) immediatedly upstream of the β-domain coding sequence, and fragments creating the 30 3' splice acceptor (SA) site were cloned into pCY-601 and pCY-6 immediately downstream of the β-domain coding sequence. The resulting plasmids are referred to as pLZ-601 and pLZ-6, respectively.

E. Fragment II was isolated out of pBluescript as a Mun I to BspE I fragment, and cloned into the pBluescript-Fragment I clone at the corresponding sites, to yield clone pBS-FI/FII (FIG. 9), Fragment III was isolated out of pBluescript as a BstE II to BspE I fragment, and cloned into the corresponding sites of pBS-FI/FII to yield pBS-FI/FII/FIII (FIG. 9). This final bluescript clone contained the region spanning Factor VIII cDNA from the second Bcl I site to the BspE I site, and contained the IVS 14 and splice acceptor sequence inserted at the appropriate sites. The pBS-FI/FII/FIII clone was then sequenced. Cloning Splice Donor and Acceptor Sites into a Factor VIII cDNA Vector (pCY-6) Fragment AB and Fragment I/II/III were isolated out of pBluescript and cloned into pCY-6 in the following manner:

A. Fragment I/II/III was isolated from pBS-FI/FII/FIII as a Bcl I to BspE I fragment.

B. pCY-601 was digested to completion with BspE I, linearizing the plasmid. This linear DNA was partially digested with Bcl I for 5 minutes, and then immediately run on a gel. The band corresponding to a fragment which had been cut only at the BspE I and the second Bcl I site was isolated and extracted from the agarose gel. This isolated fragment was ligated to Fragment I/II/III and yielded pCY-601/FI/FII/FIII (FIG. 9).

C. Fragment AB was isolated from pBS-SD as a Kpn I to Tth111 I fragment, and cloned into the corresponding sites of pCY-601/FI/FII/FIII to yield pLZ-601.

D. Plasmids pCY-6 and pLZ-601 were digested sequentially with enzymes Nco I and Sal I. The small fragment of the pCY-6 digest and the large fragment of the pLZ-601 digest were isolated and ligated together to yield plasmid pLZ-6, a second β-domain intron Factor VIII expression plasmid.

pCY-6 and pCY-601 are expression plasmids for full-length Factor VIII cDNA. The difference between the two is that the former contains an intron in the 5' untranslated region of the Factor VIII transcript, derived from the second IVS of rabbit beta globin gene. The latter lacks this engineered IVS. In vitro experiments have shown that pCY-601 yields undetectable levels of Factor VIII, while pCY-6 yields low but detectable Factor VIII levels.

Expression Assays

To test expression of the various Factor VIII cDNA plasmids including those created as described above, plasmids were transfected at a concentration of 2.0–2.5 βg/ml into HuH-7 human carcinoma cells using the calcium phosphate precipitation method described by O'Mahoney et al. (1994) *DNA & Cell Biol.* 13(12): 1227–1232. Expression levels were measured using the KabiCoATest (Kabi Inc., Sweden). This is both a quantitative and a qualitative assay for measuring Factor VIII expression, because it measures enzymatic activity of Factor VIII.

Reverse Transcriptase-PCR Analysis of Cells Transfected With Factor VIII Expression Plasmids To confirm that the engineered intron spanning the β-domain of the Factor VIII cDNA in plasmid pLZ-6 resulted in proper splicing of the β-domain coding region, reverse transcriptase (RT)-PCR analysis was performed as follows:

HUH7 cells in T-75 flasks were transfected via $CaPO_4$ precipitation with 36 βg of each of the following DNA plasmids:

pCY-2 β-domain deleted human Factor VIII cDNA
pCY-6 Full-length human Factor VIII cDNA
pLZ-6 Full length human Factor VIII cDNA with engineered β-domain intron
75 ng of pCMVhGH was co-transfected as a transfection control. Untransfected cells were grown alongside as a negative control.

Total RNA was isolated from cells 24 hours post-transfection using Gibco BRL Trizol reagent, according to the standard protocol included in product insert.

RT-PCR Experiments were performed as follows: RT-PCR was performed on all RNA preps to characterize RNA. "Minus RT" PCR was performed on all RNA preps as a negative control (without RT, only DNA is amplified). PCR was performed on plasmids used in transfection assays to compare with RT-PCRs of the RNA preps. All RT-PCR was performed with Access RT-PCR system (Promega, Cat. #A1250). In each 50 βl reaction, 1.0 βg total RNA was used as template. Primer pairs were designed according to Factor VIII sequences as follows: the 5' primer anneals to the top strand of Factor VIII, about 250 base pairs upstream of the β-domain junction; while the 3' primer anneals to the bottom strand of Factor VIII, about 250 base pairs downstream of the β-domain junction.

The nucleotide sequences of the primers used to characterize (i.e., confirm) the β-domain intron splicing were as follows:

5' primer TS 2921–2940: $^{5'}$TGG TCT ATG AAG ACA CAC TC$^{3'}$
(20 mer)

3' primer BS 6261–6280:
$^{5'}$TGA GCC CTG TTT CTT AGA AC$^{3'}$
(20 mer)

RT-PCR files were set up according to manufacturer's recommendation:
48° C., 45 minutes;×1 cycle
94° C., 2 minutes;×1 cycle
94° C., 30 sec;×40 cycles
60° C., 1 min;×40 cycles
68° C., 2 min;×40 cycles
68° C., 7 min;×1 cycle
4° C., soak overnight The data obtained from the RT-PCR assays demonstrated that engineered β-domain intron was spliced as predicted. The RT-PCR product (~500 bp) generated from pLZ-6 (containing the β-domain intron) was similar to that obtained from pCY-2 (containing β-domain deleted Factor VIII cDNA). The RT-PCR product observed for pCY-6 (containing the full length Factor VIII cDNA) yielded a much larger band (~3.3 kb).

In the control groups, it was confirmed that DNA from the Huh-7 cells transfected with various Factor VIII constructs were consistent with regular PCR results of the corresponding plasmids. Background bands from untransfected Huh-7 cells were presumably contributed by cross-over during sample handling. This can be further investigated by using polyA+RNA as template, as well as by setting up RT-PCR with different primer sets.

Example 2

Correction of Consensus and near Consensus Splice Sites Within a Human Factor VIII Gene Plasmid pCY-2, containing the coding region of the β-domain deleted human Factor VIII cDNA (nucleotides 1006–5379 of SEQ ID NO:2), was analyzed using the MacVector™ program for consensus and near consensus (a) splice donor sites, (b) splice acceptor sites and (c) branch sequences. Near consensus 5' splice donor sites were selected using the following criteria: sites were required to contain at least 5 out of the 9 splice donor consensus bases (i.e., (C/A)AG<u>GT</u>(A/G)AGT), including the invariant <u>GT</u>, provided that if only 5 out of 9 bases were present, these 5 bases were located consecutively in a row. Near consensus 3' splice acceptor sites were selected using the following criteria: sites were required to contain at least 3 out of the following 14 splice acceptor consensus bases (Y=10)CA<u>GG</u>

(wherein Y is a pyrimidine within the pyrimidine track), including the invariant AG. Only branch sequences which were 100% consensus were searched for.

Using these criteria, 23 near consensus 5' splice donor sequences, 22 near consensus 3' splice acceptor sequences, and 18 consensus branch sequences were identified. No consensus 5' splice donor or 3' splice acceptor sequences were identified. To correct these near consensus splice donor and acceptor sequences, and consensus branch sequences, it was first determined whether the invariant GT, AG, or A bases within the site could be substituted without changing the coding sequence of the site. If they could be, then these conservative (silent) substitutions were made, thereby rendering the site non-consensus (since the invariant bases are required for recognition as a splice site).

If the invariant bases within selected consensus and near consensus sites could not be substituted without changing the coding sequence of the site (i.e., if no degeneracy existed for the amino acid sequence coded for), then the maximum number of silent point mutations were made to render the site as far from consensus as possible. All bases which contributed to homology of the consensus or near consensus site with the corresponding consensus sequence, and which were able to be conservatively substituted (with non-consensus bases), were mutated.

Using these guidelines, 99 silent point mutations were selected, as shown in FIGS. 4A–4C. The positions of each of these silent point mutations is shown in FIG. 3.

To prepare a new pCY-2 human β-domain deleted Factor VIII cDNA coding sequence which contains the above-described corrections, the following procedure can be used:

Overlapping 60-mer oligonucleotides can be synthesized based on the coding sequence of pCY2. Each of the 185 oligonucleotide contains the desired corrections. These oligonucleotides are then assembled in five segments (shown in FIG. 9) using the method of Stemmer et al. (1995) *Gene* 164: 49–53. Prior to assembly, each segment can be sequenced and tested in in vitro transfection assays (nuclear and cytoplasmic RNA analysis) in pCY2. A schematic illustration of this process is shown in FIG. 8. The plasmid containing the new corrected coding sequence is desginated "pDJC."

To test expression levels of pDJC, the plasmid can be transfected at a concentration of 2.0–2.5 βg/ml into HuH-7 human carcinoma cells using any suitable transfection technique, such as the calcium phosphate precipitation method described by O'Mahoney et al. (1994) *DNA & Cell Biol.* 13(12): 1227–1232. Factor VIII expression can then be measured using the KabiCoATest (Kabi Inc., Sweden). This is both a quantitative and a qualitative assay for measuring Factor VIII expression, because it measures enzymatic activity of Factor VIII. Alternatively, plasmids such as pDJC can be tested for in vivo expression using the procedure described below in Example 4.

Example 3

Optimized Expression Vectors

Optimized expression vectors for liver-specific and endothelium-specific human Factor VIII expression were prepared and tested as follows:

The β-domain deleted human Factor VIII cDNA was obtained through Bayer Corporation in plasmid p25D, having a coding sequence corresponding to nucleotides 1006–5379 of SEQ ID NO:2. The human thyroid binding globulin promoter (TBG) (bases –382 to +3) was obtained by PCR from human liver genomic DNA (Hayashi et al. (1993) *Mol. Endo.* 7:1049). The human endothelin-1 (ET-1) gene promoter (Lee et al. (1990) *J. Biol. Chem.* 265(18) was synthesized by amplification of overlapping oligos in a PCR reaction.

After sequence confirmation, the TBG and ET-1 promoters were cloned into two separate vectors upstream of an optimized leader sequence (SEQ ID NO: 11), using standard cloning techniques. The leader sequence was designed in a similar manner to that reported by Kozak et al. (1994) *J. Mol. Biol.* 235:95) and synthesized (Retrogen Inc., San Diego, Calif.) as 71 base pair top and bottom strand oligos, annealed and cloned upstream of the Factor VIII ATG. The 126 base pair intron-1 of the rabbit β-globin gene, containing the nucleotide sequence modifications shown in FIG. 23 (SEQ ID NO:7), was also synthesized and inserted into the leader sequence following base 42 of the 71 nucleotide sequence.

In the construct containing the TBG promoter, top and bottom strands of the human alpha-1 microglobulin/bikunin enhancer (ABP), sequences –2804 through –2704 (Rouet et al. (1992) *J. Biol. Chem.* 267:20765), were synthesized, annealed and cloned upstream of the promoter. Cloning sites flanking the enhancer were designed to facilitate easy multimerization. In the construct containing the ES-1 promoter, top and bottom strands of the human c-fos SRE enhancer (Treisman et al. (1986) *Cell* 46) were synthesized, annealed and cloned upstream of the promoter.

The post-transcriptional regulatory element (PRE) from hepatitis B virus, was isolated from plasmid Adw-HTD as a 587 base-pair Stu I-Stu I fragment. It was cloned into the 3' UTR of the Factor VIII construct (at the Hpa I site) containing the TBG promoter and ABP enhancers, upstream of the polyadenylation sequence. A two copy PRE element was isolated as a Spe I-Spe I fragment from an early vector where two copies had ligated together. This fragment was converted to a blunt end fragment by the Klenow fragment of E-coli DNA polymerase I and also cloned into the Factor VIII construct at the same Hpa I site.

Thus, the following constructs were produced using the foregoing materials and methods:

Plasmid pCY-2 having a 5' untranslated region containing the TBG promoter, two copies of the ABP enhancer; and the modified rabbit β-globin IVS, all upstream of the human β-domain deleted Factor VIII gene.

Plasmid pCY2-SE5 which was identical to pCY-2, except that the TBG promoter was replaced by the ET-1 gene promoter, and the ABP enhancers (both copies) were replaced by one copy of the SRE enhancer.

Plasmid pCY-201 which was identical to pCY-2, except that it lacked the 5' intron.

Plasmid pCY-401 and pCY-402 which were identical to pCY-201, except that they contained one and two copies of the HBV PRE, respectively.

Expression levels for each of the foregoing gene constructs was compared in human hepatoma cells (HUH-7) maintained in DMEM (Dulbecco's modified Eagle medium (GIBCO BRL), supplemented with 10% heat inactivated fetal calf serum (10% FCS), penicillin (50 IU/ml), and streptomycin (50 βg/ml) in a humidified atmosphere of 5% $CO_2$ at 37° C. For experiments involving quantitation of human factor VIII protein, media was supplemented with an additional 10% FCS. DNA transfection was performed by a calcium phosphate coprecipitation method.

Other human Factor VIII gene constructs (shown below in Table I) tested for expression, prepared as described above, included constructs which were identical to pCY-2, except that they contained (a) the TBG promoter with no enhancer or 5' intron, (b) the TBG promoter with a 5' modified rabbit β-globin intron (present within the leader sequence), but no enhancer, (c) the TBG promoter with one copy of the ABP enhancer and a 5' modified rabbit β-globin intron (present within the leader sequence), and (d) the TBG promoter with two copies of the ABP enhancer and a 5' modified rabbit β-globin intron (present within the leader sequence).

Active Factor VIII protein was measured from tissue culture supernatants by COAtest VIII:c/4 kit assay specific for active Factor VIII protein. Transfection efficiencies were normalized to expression of cotransfected human growth hormone (hGH).

As shown below in Table I, liver-specific human Factor VIII expression is significantly increased by the combined use of the TBG promoter and a 5' intron within the 5' UTR of the gene construct. Expression is further increased (over 30 fold) by adding a copy of the ABP enhancer in the same construct. Expression is still further increased (over 60 fold) by using two copies of the ABP enhancer in the same construct. In addition, as shown in FIG. 18, expression is also significantly increased by adding one or more PRE sequences into the 3' UTR of the gene construct, although, in this experiment, not as much as by adding a 5' intron within the 5' UTR.

TABLE I

| 5' Region Tested | Fold Increase in Factor VIII Expression in Vitro |
| --- | --- |
| TBG Promoter | 1 |
| TBG Promoter, 5' Intron | 3.5 |
| ABP Enhancer (1 copy), TBG Promoter, 5' Intron | 30.1 |
| ABP Enhancer (2 copies), TBG Promoter, 5' Intron (pCY-2) | 63.2 |

Expression of pCY2-SE5 was also tested and compared with pCY-2 in (a) bovine aortic endothelial cells and (b) HUH-7 cells. Transfections and Assays were performed as described above. Significantly more biologically active human Factor VIII was secreted from cells transfected with pCY2-SE5 than with pCY-2 (625 pg/ml vs. 280 pg/ml). While liver-specific pCY-2 expressed more than 10 ng/ml of human Factor VII from HUH-7 cells, no human Factor VIII could be detected from pCY2-SE5 transfected HUH-7 cells.

Constructs were also tested in vivo. Specifically, pCY-2 and pCY2-SE5 were tested in mouse models by injecting mice (tail vein) with 10 βg of DNA in one 1.0 ml of solution (0.3 M NaCl, pH 9). Plasmids pCY-6, pLZ-6 and pLZ-6A (described in Example I) were tested in the same experiment. Levels of human Factor VIII were measured in mouse serum.

Figure 19:
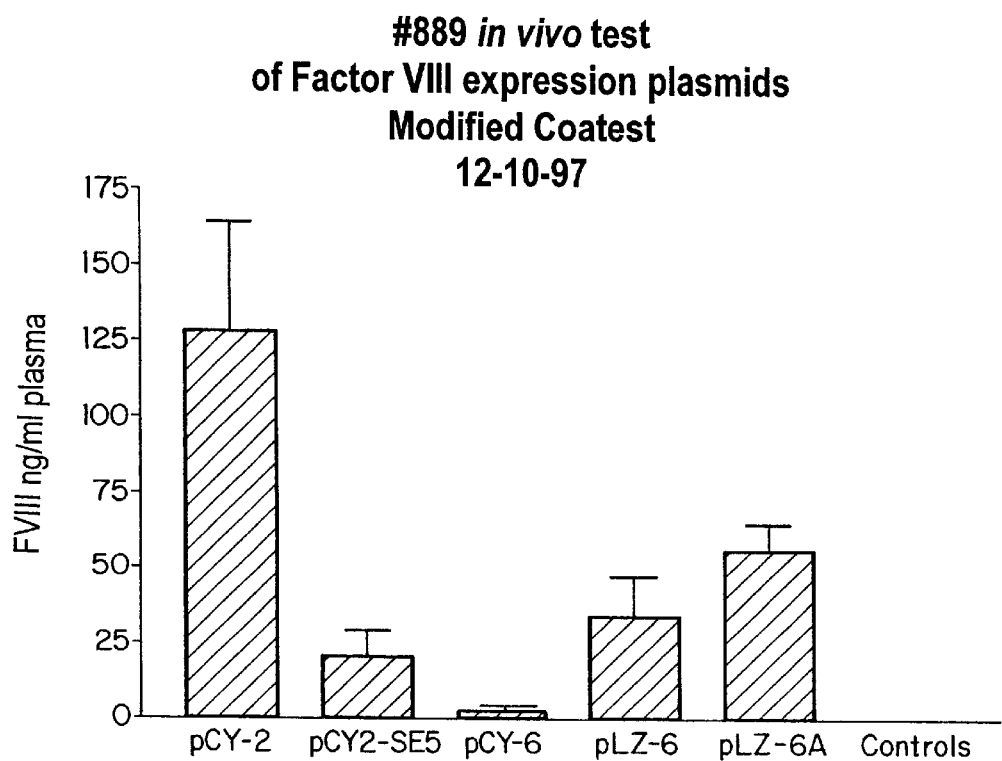
FIG. 19 is a graph comparing human Factor VIII expression in vivo in mice for plasmids containing various regulatory elements upstream of either the β-domain deleted or full-length human Factor VIII gene. Plasmid pCY-2 has a 5' untranslated region containing the liver-specific thyroxin binding globulin (TBG) promoter, two copies of the liver-specific alpha-1 microglobulin/bikunin (ABP) enhancer; and a modified rabbit β-globin IVS, all upstream of the human β-domain deleted Factor VIII gene. Plasmid pCY2-SE5 is identical to pCY-2 except that the TBG promoter was replaced by the endothelium-specific human endothelin-1 (ET-1) gene promoter, and the ABP enhancers (both copies) were replaced by one copy of the human c-fos gene (SRE) enhancer. Plasmid pCY-6 is identical to pCY-2, except that the human β-domain deleted Factor VIII gene was replaced by the full-length human Factor VIII gene. Plasmid pLZ-6 is identical to pCY-6, except that the full-length human Factor VIII gene contained an intron spanning the β-domain. Plasmid pLZ-6A is identical to pLZ-6, except that it contains one corrected near consensus 3' splice acceptor site (A to C at base 3084 of pCY-6 (SEQ ID NO:3). Each bar represents an average of five mice.

The results are shown in FIG. 19. Plasmid pCY-2, containing the TBG promoter, 2 copies of the ABP enhancer, and an optimized 5' intron, had the highest expression, followed by pLZ-6A, pLZ-6, pCY2-SE5 and pCY-6.

Plasmid pCY-2 was also tested in vivo in mice, along with plasmid p25D which contained the same coding sequence (for human β-domain deleted Factor VIII) without an optimized 5' UTR. Specifically, instead of 2 copies of the ABP enhancer, one copy of the TBG promoter and a leader sequence containing an optimized (i.e., modified to contain consensus splice donor and acceptor sites and a consensus branch and pyrimidine track sequence) 5' rabbit β-globin intron (as contained in the 5' UTR of pCY-2), p25D contained within its 5' UTR one copy of the CMV enhancer, one copy of the CMV promoter, and a leader sequence containing an unmodified short (130 bp) chimeric human IgE intron (containing uncorrected near consensus splice donor and acceptor sites). Plasmids were injected into mice (tail vein) in the form of asialoorosomucoid/polylysine/DNA complexes formed as described below in Example 4. Mice were injected with 10 βg of DNA (complexed) in 1.0 of solution (0.3 M NaCl, pH 9).

Figure 25:
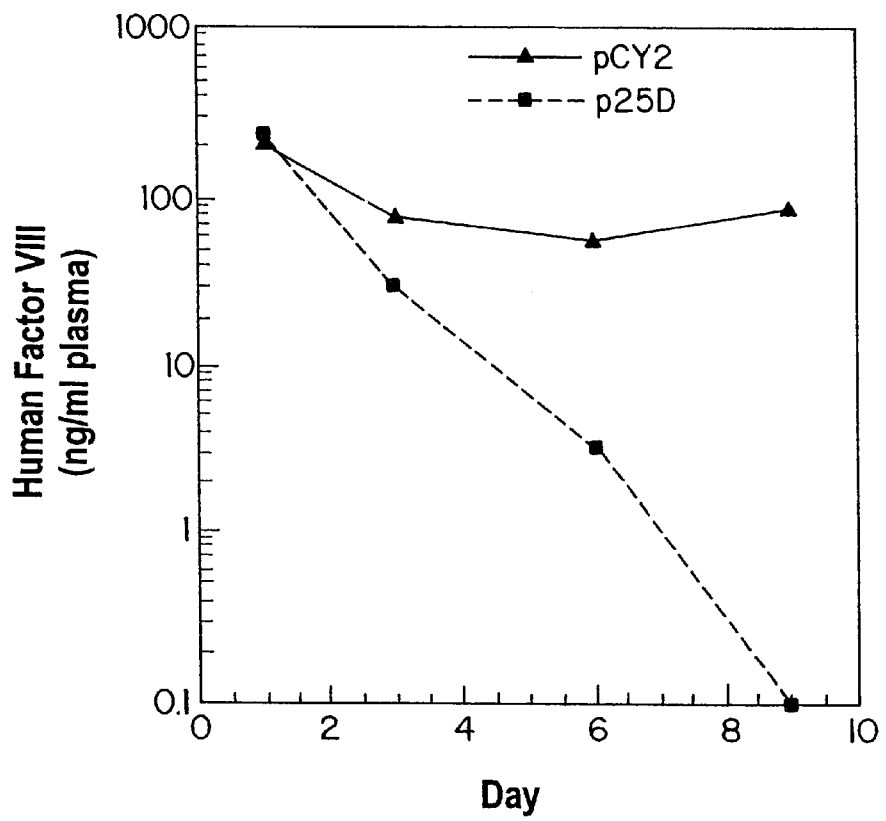
FIG. 25 is a graph comparing expression of plasmid pCY-2 and p25D in vivo in mice. Both plasmids contain the same coding sequence (for human β-domain deleted Factor VIII). Plasmid pCY-2 has an optimized 5' UTR containing two copies of the ABP enhancer, one copy of the TBG promoter and a leader sequence split by an optimized 5' rabbit β-globin intron. Plasmid p25D has a 5' UTR containing one copy of the CMV enhancer, one copy of the CMV promoter, and a leader sequence containing a short (130 bp) chimeric human IgE intron. Each bar represents an average of 5 mice.

The results are shown in FIG. 25 and demonstrate that optimization of gene constructs by modification of 5' UTRs to contain novel combinations of strong tissue-specific promoters and enhancers, and optimized introns (e.g. modified to contain consensus splice donor and acceptor sites and a consensus branch and pyrimidine track sequence) significantly increases both levels and duration of gene expression. Notably, expression of p25D shut off after only 8 days, whereas expression of pCY-2 was maintained at nearly 100% of initial levels (well in the human therapeutic range of 10 ng/ml or more) for over 10 days. In the same experiment, expression was maintained well in the therapeutic range for greater than 30 days.

Overall, the results of the foregoing examples demonstrate that gene expression can be significantly increased and prolonged in vivo by optimizing untranslated regulatory regions and/or coding sequences in accordance with the teachings of the present invention.

Example 4

Targeted Delivery of Novel Genes to Cells

Novel genes of the invention, such as novel Factor VIII genes contained in appropriate expression vectors, can be selectively delivered to target cells either in vitro or in vivo as follows:

Formation of Targeted Molecular Complexes

I. Reagents

Protamine, poly-L-lysine (4 kD, 10 kD, 26 kD; mean MW) and ethidium bromide can be purchased from Sigma Chemical Co., St. Louis, Mo. 1-[3-(dimethylamino)-propyl]-3-ethylcarbodiimide (EDC) can be purchased from Aldrich Chemical Co, Milwaukee, Wis. Synthetic polylysines can be purchased from Research Genetics (Huntsville, Ala.) or Dr. Schwabe (Protein Chemistry Facility at the Medical University of South Carolina). Orosomucoid (OR) can be purchased from Alpha Therapeutics, Los Angeles, Calif. Asialoorosomucoid (AsOR) can be prepared from orosomucoid (15 mg/ml) by hydrolysis with 0.1 N sulfuric acid at 76° C. for one hour. AsOR can then be purified from the reaction mixture by neutralization with 1.0 N NaOH to pH 5.5 and exhaustive dialysis against water at room temperature. AsOR concentration can be determined using an extinction coefficient of 0.92 ml mg$^{-1}$, cm$^{-1}$ at 280 nm. The thiobarbituric acid assay of Warren (1959) *J. Biol. Chem.* 234:1971–1975 or of Uchida (1977) *J. Biochem.* 82:1425–1433 can be used to verify desialylation of the OR. AsOR prepared by the above method is typically 98% desialyated.

II. Formation of Carrier Molecules

Carrier molecules capable of electrostatically binding to DNA can be prepared as follows: AsOR-poly-L-lysine conjugate (AP26K) can be formed by carbodiimide coupling similar to that reported by McKee (1994) *Bioconj. Chem.* 5:306–311. AsOR, 26kD poly-L-lysine and EDC in a 1:1:0.5 mass ratio can be reacted as follows. EDC (dry) is added directly to a stirring aqueous AsOR solution. Polylysine (26 kD) is then added, the reaction mixture adjusted to pH 5.5–6.0, and stirred for two hours at ambient temperature. The reaction can be quenched by addition of $Na_3PO_4$ (200 mM, pH 11) to a final concentration of 10 mM. The AP26K conjugate can be first purified on a Fast Flow Q Sepharose anion exchange chromatography column (Pharmacia) eluted with 50 mM Tris, pH 7.5; and then dialyzed against water.

III. Calculation of Charge Ratios (+/−)

Charge ratios of purified carrier molecules can be determined as follows: Protein-polylysine conjugates (e.g., AsOR-PL or OR-PL) are exhaustively dialyzed against ultra-pure water. An aliquot of the dialyzed conjugate solution is lyophilized, weighed and dissolved in ultra-pure water at a specific concentration (w/v). Since polylysine has minimal absorbance at 280 nm, the AsOR component of AsOR-polylysine (w/v) is calculated using the extinction coefficient at 280 nm. The composition of the conjugate is estimated by comparison of the concentration of the conjugate (w/v) with the concentration of AsOR (w/v) as determined by UV absorbance. The difference between the two determinations can be attributed to the polylysine component of the conjugate. The composition of OR-polylysine can be calculated in the same manner. The ratio of conjugate to DNA (w/w) necessary for specific charge ratios then can be calculated using the determined conjugate composition. Charge ratios for molecular complexes made with, e.g., polylysine or protamine, can be calculated from the amino acid composition.

IV. Complexation With DNA

To form targeted DNA complexes, DNA (e.g., plasmid DNA) is preferably prepared in glycine (e.g., 0.44 M, pH 7), and is then rapidly added to an equal volume of carrier molecule, also in glycine (e.g., 0.44 M, pH 7), so that the final solution is isotonic.

V. Fluorescence Quenching Assay

Binding efficiencies of DNA to various polycationic carrier molecules can be examined using an ethidium bromide-based quenching assay. Solutions can be prepared containing 2.5 βg/ml EtBr and 10 βg/ml DNA (1:5 EtBr:DNA phosphates molar ratio) in a total volume of 1.0 ml. The polycation is added incrementally with fluorescence readings taken at each point using a fluorometer (e.g., a Sequoia-Turner 450), with excitation and emission wavelengths at 540 nm and 585 nm, respectively. Fluorescence readings are preferably adjusted to compensate for the change in volume due to the addition of polycation, if the polycation did not exceed 3% of the original volume. Results can be reported as the percentage of fluorescence relative to that of uncomplexed plasmid DNA (no polycation).

Cell Delivery In Vivo or In Vitro

DNA complexes prepared as described above can be administered in solution to subjects via injection. By way of example, a 0.1–1.0 ml dose of complex in solution can be injected intravenously via the tail vein into adult (e.g., 18–20 gm) BALB/C mice, at a dose ranging from <1.0–10.0 µg of DNA complex per mouse.

Alternatively, DNA complexes can be incubated with cells (e.g., HuH cells) in culture using any suitable transfection protocol known in the art for targeted uptake. Target cells for transfection must contain on their surface a component capable of binding to the cell-binding component of the DNA complex.

Equivalents

Although the invention has been described with reference to its preferred embodiments, other embodiments can achieve the same results. Those skilled in the art will recognize or be able to ascertain using no more than routine experimentation, numerous equivalents to the specific embodiments described herein. Such equivalents are considered to be within the scope of this invention and are encompassed by the following claims.

Incorporation by Refreence

The contents of all references and patents cited herein are hereby incorporated by reference in their entirety.

What is claimed is:

1. An isolated DNA encoding a Factor VIII protein, wherein the DNA comprises one or more consensus or near consensus splice sites which have been corrected relative to the consensus or near consensus splice sites occurring in the factor VIII sequence of SEQ ID NO: 2 or 4, wherein the correction results in increased expression of the DNA.

2. The isolated DNA of claim 1 comprising a cDNA clone.

3. The isolated DNA of claim 1 wherein the one or more consensus or near consensus splice sites comprises a 5' splice donor site which is corrected by mutating one or both of the nucleotides within the essential GT pair.

4. The isolated DNA of claim 1 wherein the one or more consensus or near consensus splice sites comprises a 3' splice acceptor site which is corrected by mutating one or both of the nucleotides within the essential AG pair.

5. The isolated DNA of claim 1 comprising a cDNA which is expressed as a β-domain deleted Factor VIII protein.

6. An expression vector comprising the isolated DNA of claim 1 operably linked to a promoter sequence.

7. The isolated DNA of claim 1, wherein the one or more consensus or near consensus splice sites contain either:
  (A) at least five out of nine bases of a consensus 5' splice donor site, (C/A)AGGT(A/G)AGT, including the invariant GT, provided that if only five out of nine bases are present, the five bases are located consecutively in a row; or
  (B) at least three out of fourteen bases of a consensus 3' splice acceptor site, (Y=10)CAGG (wherein Y is a pyrimidine within the pyrimidine track), including the invariant AG.

8. An isolated DNA comprising the coding region of a full-length Factor VIII gene, wherein the coding region contains an intron spanning the portion of the gene encoding the β-domain.

9. An expression vector comprising the isolated DNA of claim 8 perably linked to a promoter sequence.

10. A method of producing Factor VIII comprising introducing the expression vector of claim 9 into a host cell capable of expressing the vector, and allowing for expression of the vector.

11. A method of increasing expression of a gene encoding a Factor VIII protein comprising correcting one or more consensus or near consensus splice sites within the nucleotide sequence of the gene and expressing the gene in a cell.

12. The method of claim 11 comprising mutating one or both of the nucleotides within the essential GT pair, if the consensus or near consensus splice site is a 5' splice site, or mutating one or both of the nucleotides within the essential AG pair, if the consensus or near consensus splice site is a 3' splice site.

13. The method of claim 11 wherein the gene is expressed as a β-domain deleted Factor VIII protein.

14. The method of claim 11, further comprising identifying the one or more consensus or near consensus splice sites using the following algorithm:
  (A) the site contains at least five out of nine bases of a consensus 5' splice donor site, (C/A)AGGT(A/G)AGT, including the invariant GT, provided that if only five out of nine bases are present, the five bases are located consecutively in a row; or
  (B) the site contains at least three out of fourteen bases of a consensus 3' splice acceptor site, (Y=10)CAGG (wherein Y is a pyrimidine within the pyrimidine track), including the invariant AG.

15. A method of increasing expression of a gene comprising identifying one or more consensus or near consensus splice sites within the gene using the following algorithm:
  (A) the site contains at least five out of nine bases of a consensus 5' splice donor site, (C/A)AGGT(A/G)AGT, including the invariant GT, provided that if only five out of nine bases are present, the five bases are located consecutively in a row; or
  (B) the site contains at least three out of fourteen bases of a consensus 3' splice acceptor site, (Y=10)CAGG (wherein Y is a pyrimidine within the pyrimidine track), including the invariant AG,
  and correcting multiple consensus or near consensus splice sites within the gene which meet the requirements of the algorithm, wherein the algorithm further requires that the consensus or near consensus splice site include a consensus branch sequence, (C/T)N(C/T)T(A/G)A(C/T), wherein N is any nucleotide, located upstream from a consensus or near consensus 3' splice acceptor site.

16. A method of increasing expression of a gene encoding a Factor VIII protein comprising identifying one or more consensus or near consensus splice sites within the gene using the following algorithm:
  (A) the site contains at least five out of nine bases of a consensus 5' splice donor site, (C/A)AGGT(A/G)AGT, including the invariant GT, provided that if only five out of nine bases are present, the five bases are located consecutively in a row; or
  (B) the site contains at least three out of fourteen bases of a consensus 3' splice acceptor site, (Y=10)CAGG (wherein Y is a pyrimidine within the pyrimidine track), including the invariant AG,
  and correcting multiple consensus or near consensus splice sites within the gene which meet the requirements of the algorithm.

17. The method of claim 16 wherein the gene is expressed as a β-domain deleted Factor VIII protein.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 4374 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..4374

(xi) SEQUENCE DESCRIPTION: SEQ ID NO:1:

```
ATG GAA ATA GAG CTC TCC ACC TGC TTC TTT CTG TGC CTT TTG CGA TTC      48
Met Glu Ile Glu Leu Ser Thr Cys Phe Phe Leu Cys Leu Leu Arg Phe
 1               5                  10                  15
```

```
TGC TTT AGT GCC ACC AGA AGA TAC TAC CTG GGT GCA GTG GAA CTG TCA      96
Cys Phe Ser Ala Thr Arg Arg Tyr Tyr Leu Gly Ala Val Glu Leu Ser
             20                  25                  30

TGG GAC TAT ATG CAA AGT GAT CTC GGA GAG CTG CCT GTG GAC GCA AGA     144
Trp Asp Tyr Met Gln Ser Asp Leu Gly Glu Leu Pro Val Asp Ala Arg
         35                  40                  45

TTT CCT CCT CGC GTG CCA AAA TCT TTT CCA TTC AAC ACC TCA GTC GTG     192
Phe Pro Pro Arg Val Pro Lys Ser Phe Pro Phe Asn Thr Ser Val Val
     50                  55                  60

TAC AAA AAG ACT CTG TTT GTA GAA TTC ACG GTT CAC CTT TTC AAC ATC     240
Tyr Lys Lys Thr Leu Phe Val Glu Phe Thr Val His Leu Phe Asn Ile
 65                  70                  75                  80

GCT AAG CCA AGG CCA CCC TGG ATG GGT CTG CTA GGT CCT ACC ATC CAA     288
Ala Lys Pro Arg Pro Pro Trp Met Gly Leu Leu Gly Pro Thr Ile Gln
                 85                  90                  95

GCT GAG GTT TAT GAT ACA GTG GTC ATT ACA CTT AAG AAC ATG GCT TCC     336
Ala Glu Val Tyr Asp Thr Val Val Ile Thr Leu Lys Asn Met Ala Ser
             100                 105                 110

CAT CCT GTC TCC CTT CAT GCT GTT GGT GTA TCC TAC TGG AAA GCT TCT     384
His Pro Val Ser Leu His Ala Val Gly Val Ser Tyr Trp Lys Ala Ser
         115                 120                 125

GAG GGA GCT GAA TAT GAT GAT CAG ACC AGT CAA AGG GAG AAA GAA GAT     432
Glu Gly Ala Glu Tyr Asp Asp Gln Thr Ser Gln Arg Glu Lys Glu Asp
     130                 135                 140

GAT AAA GTC TTC CCT GGT GGA AGC CAT ACA TAT GTC TGG CAA GTC CTG     480
Asp Lys Val Phe Pro Gly Gly Ser His Thr Tyr Val Trp Gln Val Leu
145                 150                 155                 160

AAA GAG AAT GGT CCA ATG GCC TCC GAC CCA CTG TGC CTT ACC TAC TCA     528
Lys Glu Asn Gly Pro Met Ala Ser Asp Pro Leu Cys Leu Thr Tyr Ser
                 165                 170                 175

TAT CTT TCT CAT GTG GAC CTG GTT AAA GAC TTG AAT TCA GGC CTC ATT     576
Tyr Leu Ser His Val Asp Leu Val Lys Asp Leu Asn Ser Gly Leu Ile
             180                 185                 190

GGA GCC CTA CTA GTA TGT AGA GAA GGG AGT CTG GCC AAG GAA AAG ACA     624
Gly Ala Leu Leu Val Cys Arg Glu Gly Ser Leu Ala Lys Glu Lys Thr
         195                 200                 205

CAG ACC TTG CAC AAA TTT ATA CTA CTT TTT GCT GTA TTT GAT GAA GGG     672
Gln Thr Leu His Lys Phe Ile Leu Leu Phe Ala Val Phe Asp Glu Gly
     210                 215                 220

AAA AGT TGG CAC TCA GAA ACA AAG AAC TCC CTC ATG CAA GAT AGG GAT     720
Lys Ser Trp His Ser Glu Thr Lys Asn Ser Leu Met Gln Asp Arg Asp
225                 230                 235                 240

GCT GCA TCT GCT CGG GCC TGG CCT AAA ATG CAC ACA GTC AAT GGT TAT     768
Ala Ala Ser Ala Arg Ala Trp Pro Lys Met His Thr Val Asn Gly Tyr
                 245                 250                 255

GTA AAC AGG AGC CTG CCA GGA CTG ATT GGA TGC CAC AGG AAA TCA GTC     816
Val Asn Arg Ser Leu Pro Gly Leu Ile Gly Cys His Arg Lys Ser Val
             260                 265                 270

TAT TGG CAT GTT ATA GGA ATG GGC ACC ACT CCT GAA GTG CAC TCA ATA     864
Tyr Trp His Val Ile Gly Met Gly Thr Thr Pro Glu Val His Ser Ile
         275                 280                 285

TTC CTC GAA GGA CAC ACA TTT CTT GTT AGA AAC CAT CGC CAG GCG TCC     912
Phe Leu Glu Gly His Thr Phe Leu Val Arg Asn His Arg Gln Ala Ser
     290                 295                 300

TTG GAA ATC TCG CCA ATA ACT TTC CTT ACT GCT CAA ACA CTC CTC ATG     960
Leu Glu Ile Ser Pro Ile Thr Phe Leu Thr Ala Gln Thr Leu Leu Met
305                 310                 315                 320

GAC CTT GGA CAG TTT CTA CTG TTT TGT CAT ATC TCT TCC CAC CAA CAT    1008
Asp Leu Gly Gln Phe Leu Leu Phe Cys His Ile Ser Ser His Gln His
                 325                 330                 335
```

```
GAT GGC ATG GAA GCT TAT GTC AAA GTA GAC AGC TGT CCA GAG GAA CCC      1056
Asp Gly Met Glu Ala Tyr Val Lys Val Asp Ser Cys Pro Glu Glu Pro
            340                 345                 350

CAA CTA CGA ATG AAA AAT AAT GAA GAA GCG GAA GAC TAT GAT GAT GAT      1104
Gln Leu Arg Met Lys Asn Asn Glu Glu Ala Glu Asp Tyr Asp Asp Asp
            355                 360                 365

CTT ACC GAT TCT GAA ATG GAT GTG GTC AGA TTT GAT GAT GAC AAC TCT      1152
Leu Thr Asp Ser Glu Met Asp Val Val Arg Phe Asp Asp Asp Asn Ser
        370                 375                 380

CCT TCC TTT ATC CAA ATT CGC TCA GTT GCC AAG AAG CAT CCT AAA ACT      1200
Pro Ser Phe Ile Gln Ile Arg Ser Val Ala Lys Lys His Pro Lys Thr
385                 390                 395                 400

TGG GTA CAT TAC ATT GCT GCT GAA GAG GAG GAC TGG GAC TAT GCT CCC      1248
Trp Val His Tyr Ile Ala Ala Glu Glu Glu Asp Trp Asp Tyr Ala Pro
                405                 410                 415

TTA GTC CTC GCC CCC GAT GAC AGA AGT TAT AAA AGT CAA TAT TTG AAC      1296
Leu Val Leu Ala Pro Asp Asp Arg Ser Tyr Lys Ser Gln Tyr Leu Asn
            420                 425                 430

AAT GGC CCT CAG CGG ATT GGA AGG AAG TAC AAA AAA GTC CGA TTT ATG      1344
Asn Gly Pro Gln Arg Ile Gly Arg Lys Tyr Lys Lys Val Arg Phe Met
            435                 440                 445

GCA TAC ACA GAT GAA ACC TTT AAG ACT CGT GAA GCT ATT CAG CAT GAA      1392
Ala Tyr Thr Asp Glu Thr Phe Lys Thr Arg Glu Ala Ile Gln His Glu
        450                 455                 460

TCA GGA ATC TTG GGA CCT TTA CTT TAT GGG GAA GTT GGA GAC ACA CTG      1440
Ser Gly Ile Leu Gly Pro Leu Leu Tyr Gly Glu Val Gly Asp Thr Leu
465                 470                 475                 480

CTC ATT ATA TTT AAG AAT CAA GCA AGC AGA CCA TAT AAC ATC TAC CCT      1488
Leu Ile Ile Phe Lys Asn Gln Ala Ser Arg Pro Tyr Asn Ile Tyr Pro
                485                 490                 495

CAC GGA ATC ACC GAT GTC CGT CCT TTG TAT TCA CGC AGA TTA CCA AAA      1536
His Gly Ile Thr Asp Val Arg Pro Leu Tyr Ser Arg Arg Leu Pro Lys
            500                 505                 510

GGA GTA AAA CAT TTG AAG GAT TTT CCA ATT CTG CCC GGA GAA ATA TTC      1584
Gly Val Lys His Leu Lys Asp Phe Pro Ile Leu Pro Gly Glu Ile Phe
            515                 520                 525

AAA TAT AAA TGG ACA GTG ACT GTA GAA GAT GGG CCA ACT AAA TCA GAT      1632
Lys Tyr Lys Trp Thr Val Thr Val Glu Asp Gly Pro Thr Lys Ser Asp
530                 535                 540

CCT CGG TGC CTG ACC CGC TAT TAC TCT AGT TTC GTC AAT ATG GAG AGA      1680
Pro Arg Cys Leu Thr Arg Tyr Tyr Ser Ser Phe Val Asn Met Glu Arg
545                 550                 555                 560

GAT CTA GCT TCA GGA CTC ATT GGC CCT CTC CTC ATC TGC TAC AAA GAA      1728
Asp Leu Ala Ser Gly Leu Ile Gly Pro Leu Leu Ile Cys Tyr Lys Glu
                565                 570                 575

TCT GTA GAT CAA AGA GGA AAC CAG ATA ATG TCA GAC AAG AGG AAT GTC      1776
Ser Val Asp Gln Arg Gly Asn Gln Ile Met Ser Asp Lys Arg Asn Val
            580                 585                 590

ATC CTG TTT TCT GTA TTT GAT GAG AAC CGA AGC TGG TAC CTC ACA GAG      1824
Ile Leu Phe Ser Val Phe Asp Glu Asn Arg Ser Trp Tyr Leu Thr Glu
            595                 600                 605

AAT ATA CAA CGC TTT CTC CCC AAT CCC GCT GGA GTG CAG CTT GAG GAT      1872
Asn Ile Gln Arg Phe Leu Pro Asn Pro Ala Gly Val Gln Leu Glu Asp
610                 615                 620

CCA GAG TTC CAA GCC TCC AAC ATC ATG CAC AGC ATC AAT GGC TAT GTT      1920
Pro Glu Phe Gln Ala Ser Asn Ile Met His Ser Ile Asn Gly Tyr Val
625                 630                 635                 640

TTC GAT AGT TTG CAG TTG TCA GTT TGT TTG CAT GAA GTA GCA TAC TGG      1968
Phe Asp Ser Leu Gln Leu Ser Val Cys Leu His Glu Val Ala Tyr Trp
```

-continued

```
              645                 650                 655
TAC ATT CTA AGC ATT GGA GCA CAG ACT GAC TTC CTT TCT GTC TTC TTC    2016
Tyr Ile Leu Ser Ile Gly Ala Gln Thr Asp Phe Leu Ser Val Phe Phe
            660                 665                 670

TCT GGA TAT ACC TTC AAA CAC AAA ATG GTC TAT GAA GAC ACA CTC ACC    2064
Ser Gly Tyr Thr Phe Lys His Lys Met Val Tyr Glu Asp Thr Leu Thr
            675                 680                 685

CTA TTC CCA TTC TCC GGA GAA ACT GTC TTC ATG TCG ATG GAA AAC CCA    2112
Leu Phe Pro Phe Ser Gly Glu Thr Val Phe Met Ser Met Glu Asn Pro
            690                 695                 700

GGA CTA TGG ATT CTG GGG TGC CAC AAC TCA GAC TTT CGG AAC AGA GGC    2160
Gly Leu Trp Ile Leu Gly Cys His Asn Ser Asp Phe Arg Asn Arg Gly
705                 710                 715                 720

ATG ACC GCC TTA CTG AAA GTT TCC AGT TGT GAC AAG AAC ACT GGA GAT    2208
Met Thr Ala Leu Leu Lys Val Ser Ser Cys Asp Lys Asn Thr Gly Asp
            725                 730                 735

TAT TAC GAG GAC AGT TAT GAA GAT ATT TCA GCA TAC TTG CTG AGT AAA    2256
Tyr Tyr Glu Asp Ser Tyr Glu Asp Ile Ser Ala Tyr Leu Leu Ser Lys
            740                 745                 750

AAC AAT GCC ATT GAA CCA AGA AGC TTC TCC CAG AAC CCA CCA GTC TTG    2304
Asn Asn Ala Ile Glu Pro Arg Ser Phe Ser Gln Asn Pro Pro Val Leu
            755                 760                 765

AAA CGC CAT CAA CGG GAA ATA ACT CGT ACT ACT CTT CAA TCA GAT CAA    2352
Lys Arg His Gln Arg Glu Ile Thr Arg Thr Thr Leu Gln Ser Asp Gln
770                 775                 780

GAG GAA ATT GAC TAT GAT GAT ACC ATA TCA GTT GAA ATG AAG AAG GAA    2400
Glu Glu Ile Asp Tyr Asp Asp Thr Ile Ser Val Glu Met Lys Lys Glu
785                 790                 795                 800

GAT TTC GAC ATT TAT GAT GAG GAT GAA AAT CAG AGC CCC CGC AGC TTT    2448
Asp Phe Asp Ile Tyr Asp Glu Asp Glu Asn Gln Ser Pro Arg Ser Phe
            805                 810                 815

CAA AAG AAA ACA CGA CAC TAT TTT ATT GCT GCA GTG GAG AGG CTC TGG    2496
Gln Lys Lys Thr Arg His Tyr Phe Ile Ala Ala Val Glu Arg Leu Trp
            820                 825                 830

GAT TAT GGG ATG AGT AGC TCC CCA CAT GTT CTA AGA AAC AGG GCT CAG    2544
Asp Tyr Gly Met Ser Ser Ser Pro His Val Leu Arg Asn Arg Ala Gln
            835                 840                 845

AGT GGC AGT GTC CCT CAG TTC AAG AAA GTA GTA TTC CAG GAA TTT ACC    2592
Ser Gly Ser Val Pro Gln Phe Lys Lys Val Val Phe Gln Glu Phe Thr
            850                 855                 860

GAT GGC TCC TTT ACT CAA CCC TTA TAC CGT GGA GAA CTA AAT GAA CAT    2640
Asp Gly Ser Phe Thr Gln Pro Leu Tyr Arg Gly Glu Leu Asn Glu His
865                 870                 875                 880

TTG GGA CTC CTG GGG CCA TAT ATA AGA GCA GAA GTT GAA GAT AAT ATC    2688
Leu Gly Leu Leu Gly Pro Tyr Ile Arg Ala Glu Val Glu Asp Asn Ile
            885                 890                 895

ATG GTT ACC TTC AGA AAT CAG GCC TCT CGT CCC TAT TCC TTC TAT TCT    2736
Met Val Thr Phe Arg Asn Gln Ala Ser Arg Pro Tyr Ser Phe Tyr Ser
            900                 905                 910

TCC CTC ATA TCA TAT GAG GAA GAT CAG AGG CAA GGA GCA GAA CCT AGA    2784
Ser Leu Ile Ser Tyr Glu Glu Asp Gln Arg Gln Gly Ala Glu Pro Arg
            915                 920                 925

AAA AAC TTT GTC AAG CCT AAT GAA ACC AAA ACT TAC TTT TGG AAA GTG    2832
Lys Asn Phe Val Lys Pro Asn Glu Thr Lys Thr Tyr Phe Trp Lys Val
            930                 935                 940

CAA CAT CAT ATG GCA CCC ACT AAA GAT GAG TTT GAC TGC AAA GCC TGG    2880
Gln His His Met Ala Pro Thr Lys Asp Glu Phe Asp Cys Lys Ala Trp
945                 950                 955                 960

GCT TAT TTC TCC GAT GTC GAC CTG GAA AAA GAT GTG CAC TCA GGC CTG    2928
```

```
                            -continued

Ala Tyr Phe Ser Asp Val Asp Leu Glu Lys Asp Val His Ser Gly Leu
            965                 970                 975

ATT GGA CCC CTT CTG GTC TGC CAC ACC AAC ACA CTG AAC CCT GCT CAT    2976
Ile Gly Pro Leu Leu Val Cys His Thr Asn Thr Leu Asn Pro Ala His
        980                 985                 990

GGG AGA CAA GTG ACA GTA CAG GAA TTT GCT CTG TTT TTC ACC ATC TTC    3024
Gly Arg Gln Val Thr Val Gln Glu Phe Ala Leu Phe Phe Thr Ile Phe
            995                 1000                1005

GAT GAG ACC AAA AGC TGG TAC TTC ACT GAA AAT ATG GAA AGA AAC TGC    3072
Asp Glu Thr Lys Ser Trp Tyr Phe Thr Glu Asn Met Glu Arg Asn Cys
        1010                1015                1020

AGG GCT CCC TGC AAT ATC CAG ATG GAA GAT CCC ACT TTT AAA GAG AAT    3120
Arg Ala Pro Cys Asn Ile Gln Met Glu Asp Pro Thr Phe Lys Glu Asn
1025                1030                1035                1040

TAT CGC TTC CAT GCA ATC AAT GGC TAC ATA ATG GAT ACA CTA CCT GGC    3168
Tyr Arg Phe His Ala Ile Asn Gly Tyr Ile Met Asp Thr Leu Pro Gly
                1045                1050                1055

TTA GTA ATG GCT CAG GAT CAA AGG ATT CGA TGG TAT CTG CTC AGC ATG    3216
Leu Val Met Ala Gln Asp Gln Arg Ile Arg Trp Tyr Leu Leu Ser Met
            1060                1065                1070

GGC AGC AAT GAA AAC ATC CAT TCT ATT CAT TTC TCC GGA CAT GTG TTC    3264
Gly Ser Asn Glu Asn Ile His Ser Ile His Phe Ser Gly His Val Phe
        1075                1080                1085

ACT GTA CGA AAA AAA GAG GAG TAT AAA ATG GCA CTG TAC AAT CTC TAT    3312
Thr Val Arg Lys Lys Glu Glu Tyr Lys Met Ala Leu Tyr Asn Leu Tyr
    1090                1095                1100

CCC GGA GTT TTC GAG ACA GTG GAA ATG TTA CCA TCC AAA GCT GGA ATT    3360
Pro Gly Val Phe Glu Thr Val Glu Met Leu Pro Ser Lys Ala Gly Ile
1105                1110                1115                1120

TGG CGG GTG GAA TGC CTT ATT GGC GAG CAT CTA CAT GCT GGG ATG AGC    3408
Trp Arg Val Glu Cys Leu Ile Gly Glu His Leu His Ala Gly Met Ser
                1125                1130                1135

ACA CTT TTT CTG GTG TAC TCC AAT AAG TGT CAG ACT CCC CTG GGA ATG    3456
Thr Leu Phe Leu Val Tyr Ser Asn Lys Cys Gln Thr Pro Leu Gly Met
            1140                1145                1150

GCT TCT GGA CAC ATT AGA GAT TTT CAG ATT ACA GCT TCA GGA CAA TAT    3504
Ala Ser Gly His Ile Arg Asp Phe Gln Ile Thr Ala Ser Gly Gln Tyr
        1155                1160                1165

GGA CAG TGG GCC CCA AAG CTG GCC AGA CTT CAT TAT TCC GGA TCA ATC    3552
Gly Gln Trp Ala Pro Lys Leu Ala Arg Leu His Tyr Ser Gly Ser Ile
    1170                1175                1180

AAT GCC TGG AGC ACC AAG GAG CCC TTT TCT TGG ATC AAA GTT GAC CTG    3600
Asn Ala Trp Ser Thr Lys Glu Pro Phe Ser Trp Ile Lys Val Asp Leu
1185                1190                1195                1200

TTG GCA CCA ATG ATT ATT CAC GGC ATC AAG ACC CAG GGT GCC CGT CAG    3648
Leu Ala Pro Met Ile Ile His Gly Ile Lys Thr Gln Gly Ala Arg Gln
                1205                1210                1215

AAG TTC TCC AGC CTC TAC ATC TCT CAA TTT ATC ATC ATG TAT AGT CTC    3696
Lys Phe Ser Ser Leu Tyr Ile Ser Gln Phe Ile Ile Met Tyr Ser Leu
            1220                1225                1230

GAT GGG AAG AAG TGG CAG ACT TAT CGA GGA AAT TCC ACT GGA ACC CTC    3744
Asp Gly Lys Lys Trp Gln Thr Tyr Arg Gly Asn Ser Thr Gly Thr Leu
        1235                1240                1245

ATG GTC TTC TTT GGC AAT GTG GAT TCA TCT GGG ATA AAA CAC AAT ATT    3792
Met Val Phe Phe Gly Asn Val Asp Ser Ser Gly Ile Lys His Asn Ile
    1250                1255                1260

TTC AAC CCT CCA ATT ATT GCT CGA TAC ATC CGT TTG CAC CCA ACT CAT    3840
Phe Asn Pro Pro Ile Ile Ala Arg Tyr Ile Arg Leu His Pro Thr His
1265                1270                1275                1280
```

-continued

| | |
|---|---|
| TAT AGC ATT CGC AGC ACT CTT CGC ATG GAG TTG ATG GGC TGT GAT TTA<br>Tyr Ser Ile Arg Ser Thr Leu Arg Met Glu Leu Met Gly Cys Asp Leu<br>                1285                          1290                      1295 | 3888 |
| AAT AGT TGC AGC ATG CCA TTG GGA ATG GAG AGT AAA GCA ATA TCA GAT<br>Asn Ser Cys Ser Met Pro Leu Gly Met Glu Ser Lys Ala Ile Ser Asp<br>                1300                          1305                      1310 | 3936 |
| GCA CAG ATT ACT GCT TCA TCC TAC TTT ACC AAT ATG TTT GCC ACC TGG<br>Ala Gln Ile Thr Ala Ser Ser Tyr Phe Thr Asn Met Phe Ala Thr Trp<br>                1315                          1320                      1325 | 3984 |
| TCT CCT TCA AAA GCT CGA CTA CAC CTA CAA GGG AGG AGT AAT GCC TGG<br>Ser Pro Ser Lys Ala Arg Leu His Leu Gln Gly Arg Ser Asn Ala Trp<br>            1330                          1335                      1340 | 4032 |
| AGA CCT CAA GTT AAC AAT CCA AAA GAG TGG CTG CAA GTG GAC TTC CAG<br>Arg Pro Gln Val Asn Asn Pro Lys Glu Trp Leu Gln Val Asp Phe Gln<br>1345                      1350                        1355                      1360 | 4080 |
| AAG ACA ATG AAA GTC ACA GGA GTA ACT ACT CAG GGA GTA AAA TCT CTG<br>Lys Thr Met Lys Val Thr Gly Val Thr Thr Gln Gly Val Lys Ser Leu<br>                1365                          1370                      1375 | 4128 |
| CTT ACC TCT ATG TAC GTG AAG GAG TTC CTC ATA TCG TCG TCG CAA GAT<br>Leu Thr Ser Met Tyr Val Lys Glu Phe Leu Ile Ser Ser Ser Gln Asp<br>            1380                          1385                      1390 | 4176 |
| GGC CAT CAG TGG ACT CTC TTT TTT CAA AAT GGC AAA GTA AAA GTT TTC<br>Gly His Gln Trp Thr Leu Phe Phe Gln Asn Gly Lys Val Lys Val Phe<br>                1395                          1400                      1405 | 4224 |
| CAG GGA AAT CAA GAC TCC TTC ACA CCT GTC GTG AAC TCT CTA GAC CCA<br>Gln Gly Asn Gln Asp Ser Phe Thr Pro Val Val Asn Ser Leu Asp Pro<br>            1410                          1415                      1420 | 4272 |
| CCG TTA CTC ACT CGC TAC CTT CGA ATT CAC CCC CAG AGT TGG GTG CAC<br>Pro Leu Leu Thr Arg Tyr Leu Arg Ile His Pro Gln Ser Trp Val His<br>1425                      1430                        1435                      1440 | 4320 |
| CAG ATT GCC CTG AGG ATG GAG GTT CTG GGC TGC GAG GCA CAG GAC CTC<br>Gln Ile Ala Leu Arg Met Glu Val Leu Gly Cys Glu Ala Gln Asp Leu<br>                1445                          1450                      1455 | 4368 |
| TAC TGA<br>Tyr | 4374 |

(2) INFORMATION FOR SEQ ID NO:2:

(i) SEQUENCE CHARACTERISTICS:
        (A) LENGTH: 9164 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1006..5376

(xi) SEQUENCE DESCRIPTION: SEQ ID NO:2:

| | |
|---|---|
| GTCGACGGTA TCGATAAGCT TGATATCGAA TTCCTGCAGC CCGGGGGATC CACTAGTACT | 60 |
| CGAGACCTAG GAGTTAATTT TTAAAAAGCA GTCAAAAGTC CAAGTGGCCC TTGCGAGCAT | 120 |
| TTACTCTCTC TGTTTGCTCT GGTTAATAAT CTCAGGAGCA CAAACATTCC TTACTAGTCC | 180 |
| TAGAAGTTAA TTTTTAAAAA GCAGTCAAAA GTCCAAGTGG CCCTTGCGAG CATTTACTCT | 240 |
| CTCTGTTTGC TCTGGTTAAT AATCTCAGGA GCACAAACAT TCCTTACTAG TTCTAGAGCG | 300 |
| GCCGCCAGTG TGCTGGAATT CGGCTTTTTT AGGGCTGGAA GCTACCTTTG ACATCATTTC | 360 |
| CTCTGCGAAT GCATGTATAA TTTCTACAGA ACCTATTAGA AAGGATCACC CAGCCTCTGC | 420 |
| TTTTGTACAA CTTTCCCTTA AAAAACTGCC AATTCCACTG CTGTTTGGCC AATAGTGAG | 480 |

```
AACTTTTTCC TGCTGCCTCT TGGTGCTTTT GCCTATGGCC CCTATTCTGC CTGCTGAAGA    540

CACTCTTGCC AGCATGGACT TAAACCCCTC CAGCTCTGAC AATCCTCTTT CTCTTTTGTT    600

TTACATGAAG GGTCTGGCAG CCAAAGCAAT CACTCAAAGT TCAAACCTTA TCATTTTTTG    660

CTTTGTTCCT CTTGGCCTTG GTTTTGTACA TCAGCTTTGA AAATACCATC CCAGGGTTAA    720

TGCTGGGGTT AATTTATAAC TAAGAGTGCT CTAGTTTTGC AATACAGGAC ATGCTATAAA    780

AATGGAAAGA TGTTGCTTTC TGAGAGATCT CGAGGAAGCT AACAACAAAG AACAACAAAC    840

AACAATCAGG TAAGTATCCT TTTTACAGCA CAACTTAATG AGACAGATAG AAACTGGTCT    900

TGTAGAAACA GAGTAGTCGC CTGCTTTTCT GCCAGGTGCT GACTTCTCTC CCCTTCTCTT    960

TTTTCCTTTT CTCAGGATAA CAAGAACGAA ACAATAACAG CCACC ATG GAA ATA       1014
                                                  Met Glu Ile
                                                    1
```

```
GAG CTC TCC ACC TGC TTC TTT CTG TGC CTT TTG CGA TTC TGC TTT AGT     1062
Glu Leu Ser Thr Cys Phe Phe Leu Cys Leu Leu Arg Phe Cys Phe Ser
    5                  10                  15

GCC ACC AGA AGA TAC TAC CTG GGT GCA GTG GAA CTG TCA TGG GAC TAT     1110
Ala Thr Arg Arg Tyr Tyr Leu Gly Ala Val Glu Leu Ser Trp Asp Tyr
 20                  25                  30                  35

ATG CAA AGT GAT CTC GGT GAG CTG CCT GTG GAC GCA AGA TTT CCT CCT     1158
Met Gln Ser Asp Leu Gly Glu Leu Pro Val Asp Ala Arg Phe Pro Pro
             40                  45                  50

AGA GTG CCA AAA TCT TTT CCA TTC AAC ACC TCA GTC GTG TAC AAA AAG     1206
Arg Val Pro Lys Ser Phe Pro Phe Asn Thr Ser Val Val Tyr Lys Lys
         55                  60                  65

ACT CTG TTT GTA GAA TTC ACG GTT CAC CTT TTC AAC ATC GCT AAG CCA     1254
Thr Leu Phe Val Glu Phe Thr Val His Leu Phe Asn Ile Ala Lys Pro
     70                  75                  80

AGG CCA CCC TGG ATG GGT CTG CTA GGT CCT ACC ATC CAG GCT GAG GTT     1302
Arg Pro Pro Trp Met Gly Leu Leu Gly Pro Thr Ile Gln Ala Glu Val
 85                  90                  95

TAT GAT ACA GTG GTC ATT ACA CTT AAG AAC ATG GCT TCC CAT CCT GTC     1350
Tyr Asp Thr Val Val Ile Thr Leu Lys Asn Met Ala Ser His Pro Val
100                 105                 110                 115

AGT CTT CAT GCT GTT GGT GTA TCC TAC TGG AAA GCT TCT GAG GGA GCT     1398
Ser Leu His Ala Val Gly Val Ser Tyr Trp Lys Ala Ser Glu Gly Ala
             120                 125                 130

GAA TAT GAT GAT CAG ACC AGT CAA AGG GAG AAA GAA GAT GAT AAA GTC     1446
Glu Tyr Asp Asp Gln Thr Ser Gln Arg Glu Lys Glu Asp Asp Lys Val
         135                 140                 145

TTC CCT GGT GGA AGC CAT ACA TAT GTC TGG CAG GTC CTG AAA GAG AAT     1494
Phe Pro Gly Gly Ser His Thr Tyr Val Trp Gln Val Leu Lys Glu Asn
     150                 155                 160

GGT CCA ATG GCC TCT GAC CCA CTG TGC CTT ACC TAC TCA TAT CTT TCT     1542
Gly Pro Met Ala Ser Asp Pro Leu Cys Leu Thr Tyr Ser Tyr Leu Ser
165                 170                 175

CAT GTG GAC CTG GTA AAA GAC TTG AAT TCA GGC CTC ATT GGA GCC CTA     1590
His Val Asp Leu Val Lys Asp Leu Asn Ser Gly Leu Ile Gly Ala Leu
180                 185                 190                 195

CTA GTA TGT AGA GAA GGG AGT CTG GCC AAG GAA AAG ACA CAG ACC TTG     1638
Leu Val Cys Arg Glu Gly Ser Leu Ala Lys Glu Lys Thr Gln Thr Leu
             200                 205                 210

CAC AAA TTT ATA CTA CTT TTT GCT GTA TTT GAT GAA GGG AAA AGT TGG     1686
His Lys Phe Ile Leu Leu Phe Ala Val Phe Asp Glu Gly Lys Ser Trp
         215                 220                 225

CAC TCA GAA ACA AAG AAC TCC TTG ATG CAG GAT AGG GAT GCT GCA TCT     1734
His Ser Glu Thr Lys Asn Ser Leu Met Gln Asp Arg Asp Ala Ala Ser
```

-continued

```
               230                 235                 240
GCT CGG GCC TGG CCT AAA ATG CAC ACA GTC AAT GGT TAT GTA AAC AGG    1782
Ala Arg Ala Trp Pro Lys Met His Thr Val Asn Gly Tyr Val Asn Arg
    245                 250                 255

TCT CTG CCA GGT CTG ATT GGA TGC CAC AGG AAA TCA GTC TAT TGG CAT    1830
Ser Leu Pro Gly Leu Ile Gly Cys His Arg Lys Ser Val Tyr Trp His
260                 265                 270                 275

GTG ATT GGA ATG GGC ACC ACT CCT GAA GTG CAC TCA ATA TTC CTC GAA    1878
Val Ile Gly Met Gly Thr Thr Pro Glu Val His Ser Ile Phe Leu Glu
                280                 285                 290

GGT CAC ACA TTT CTT GTG AGG AAC CAT CGC CAG GCG TCC TTG GAA ATC    1926
Gly His Thr Phe Leu Val Arg Asn His Arg Gln Ala Ser Leu Glu Ile
            295                 300                 305

TCG CCA ATA ACT TTC CTT ACT GCT CAA ACA CTC TTG ATG GAC CTT GGA    1974
Ser Pro Ile Thr Phe Leu Thr Ala Gln Thr Leu Leu Met Asp Leu Gly
        310                 315                 320

CAG TTT CTA CTG TTT TGT CAT ATC TCT TCC CAC CAA CAT GAT GGC ATG    2022
Gln Phe Leu Leu Phe Cys His Ile Ser Ser His Gln His Asp Gly Met
    325                 330                 335

GAA GCT TAT GTC AAA GTA GAC AGC TGT CCA GAG GAA CCC CAA CTA CGA    2070
Glu Ala Tyr Val Lys Val Asp Ser Cys Pro Glu Glu Pro Gln Leu Arg
340                 345                 350                 355

ATG AAA AAT AAT GAA GAA GCG GAA GAC TAT GAT GAT GAT CTT ACT GAT    2118
Met Lys Asn Asn Glu Glu Ala Glu Asp Tyr Asp Asp Asp Leu Thr Asp
                360                 365                 370

TCT GAA ATG GAT GTG GTC AGG TTT GAT GAT GAC AAC TCT CCT TCC TTT    2166
Ser Glu Met Asp Val Val Arg Phe Asp Asp Asp Asn Ser Pro Ser Phe
            375                 380                 385

ATC CAA ATT CGC TCA GTT GCC AAG AAG CAT CCT AAA ACT TGG GTA CAT    2214
Ile Gln Ile Arg Ser Val Ala Lys Lys His Pro Lys Thr Trp Val His
        390                 395                 400

TAC ATT GCT GCT GAA GAG GAG GAC TGG GAC TAT GCT CCC TTA GTC CTC    2262
Tyr Ile Ala Ala Glu Glu Glu Asp Trp Asp Tyr Ala Pro Leu Val Leu
    405                 410                 415

GCC CCC GAT GAC AGA AGT TAT AAA AGT CAA TAT TTG AAC AAT GGC CCT    2310
Ala Pro Asp Asp Arg Ser Tyr Lys Ser Gln Tyr Leu Asn Asn Gly Pro
420                 425                 430                 435

CAG CGG ATT GGT AGG AAG TAC AAA AAA GTC CGA TTT ATG GCA TAC ACA    2358
Gln Arg Ile Gly Arg Lys Tyr Lys Lys Val Arg Phe Met Ala Tyr Thr
                440                 445                 450

GAT GAA ACC TTT AAG ACT CGT GAA GCT ATT CAG CAT GAA TCA GGA ATC    2406
Asp Glu Thr Phe Lys Thr Arg Glu Ala Ile Gln His Glu Ser Gly Ile
            455                 460                 465

TTG GGA CCT TTA CTT TAT GGG GAA GTT GGA GAC ACA CTG TTG ATT ATA    2454
Leu Gly Pro Leu Leu Tyr Gly Glu Val Gly Asp Thr Leu Leu Ile Ile
        470                 475                 480

TTT AAG AAT CAA GCA AGC AGA CCA TAT AAC ATC TAC CCT CAC GGA ATC    2502
Phe Lys Asn Gln Ala Ser Arg Pro Tyr Asn Ile Tyr Pro His Gly Ile
    485                 490                 495

ACT GAT GTC CGT CCT TTG TAT TCA AGG AGA TTA CCA AAA GGT GTA AAA    2550
Thr Asp Val Arg Pro Leu Tyr Ser Arg Arg Leu Pro Lys Gly Val Lys
500                 505                 510                 515

CAT TTG AAG GAT TTT CCA ATT CTG CCA GGA GAA ATA TTC AAA TAT AAA    2598
His Leu Lys Asp Phe Pro Ile Leu Pro Gly Glu Ile Phe Lys Tyr Lys
                520                 525                 530

TGG ACA GTG ACT GTA GAA GAT GGG CCA ACT AAA TCA GAT CCT CGG TGC    2646
Trp Thr Val Thr Val Glu Asp Gly Pro Thr Lys Ser Asp Pro Arg Cys
            535                 540                 545

CTG ACC CGC TAT TAC TCT AGT TTC GTT AAT ATG GAG AGA GAT CTA GCT    2694
```

```
                Leu Thr Arg Tyr Tyr Ser Ser Phe Val Asn Met Glu Arg Asp Leu Ala
                            550                 555                 560

TCA GGA CTC ATT GGC CCT CTC CTC ATC TGC TAC AAA GAA TCT GTA GAT                2742
Ser Gly Leu Ile Gly Pro Leu Leu Ile Cys Tyr Lys Glu Ser Val Asp
565                 570                 575

CAA AGA GGA AAC CAG ATA ATG TCA GAC AAG AGG AAT GTC ATC CTG TTT                2790
Gln Arg Gly Asn Gln Ile Met Ser Asp Lys Arg Asn Val Ile Leu Phe
580                 585                 590                 595

TCT GTA TTT GAT GAG AAC CGA AGC TGG TAC CTC ACA GAG AAT ATA CAA                2838
Ser Val Phe Asp Glu Asn Arg Ser Trp Tyr Leu Thr Glu Asn Ile Gln
                600                 605                 610

CGC TTT CTC CCC AAT CCA GCT GGA GTG CAG CTT GAG GAT CCA GAG TTC                2886
Arg Phe Leu Pro Asn Pro Ala Gly Val Gln Leu Glu Asp Pro Glu Phe
            615                 620                 625

CAA GCC TCC AAC ATC ATG CAC AGC ATC AAT GGC TAT GTT TTT GAT AGT                2934
Gln Ala Ser Asn Ile Met His Ser Ile Asn Gly Tyr Val Phe Asp Ser
        630                 635                 640

TTG CAG TTG TCA GTT TGT TTG CAT GAG GTG GCA TAC TGG TAC ATT CTA                2982
Leu Gln Leu Ser Val Cys Leu His Glu Val Ala Tyr Trp Tyr Ile Leu
    645                 650                 655

AGC ATT GGA GCA CAG ACT GAC TTC CTT TCT GTC TTC TTC TCT GGA TAT                3030
Ser Ile Gly Ala Gln Thr Asp Phe Leu Ser Val Phe Phe Ser Gly Tyr
660                 665                 670                 675

ACC TTC AAA CAC AAA ATG GTC TAT GAA GAC ACA CTC ACC CTA TTC CCA                3078
Thr Phe Lys His Lys Met Val Tyr Glu Asp Thr Leu Thr Leu Phe Pro
                680                 685                 690

TTC TCA GGA GAA ACT GTC TTC ATG TCG ATG GAA AAC CCA GGT CTA TGG                3126
Phe Ser Gly Glu Thr Val Phe Met Ser Met Glu Asn Pro Gly Leu Trp
            695                 700                 705

ATT CTG GGG TGC CAC AAC TCA GAC TTT CGG AAC AGA GGC ATG ACC GCC                3174
Ile Leu Gly Cys His Asn Ser Asp Phe Arg Asn Arg Gly Met Thr Ala
        710                 715                 720

TTA CTG AAG GTT TCT AGT TGT GAC AAG AAC ACT GGT GAT TAT TAC GAG                3222
Leu Leu Lys Val Ser Ser Cys Asp Lys Asn Thr Gly Asp Tyr Tyr Glu
    725                 730                 735

GAC AGT TAT GAA GAT ATT TCA GCA TAC TTG CTG AGT AAA AAC AAT GCC                3270
Asp Ser Tyr Glu Asp Ile Ser Ala Tyr Leu Leu Ser Lys Asn Asn Ala
740                 745                 750                 755

ATT GAA CCA AGA AGC TTC TCC CAG AAC CCA CCA GTC TTG AAA CGC CAT                3318
Ile Glu Pro Arg Ser Phe Ser Gln Asn Pro Pro Val Leu Lys Arg His
                760                 765                 770

CAA CGG GAA ATA ACT CGT ACT ACT CTT CAG TCA GAT CAA GAG GAA ATT                3366
Gln Arg Glu Ile Thr Arg Thr Thr Leu Gln Ser Asp Gln Glu Glu Ile
            775                 780                 785

GAC TAT GAT GAT ACC ATA TCA GTT GAA ATG AAG AAG GAA GAT TTT GAC                3414
Asp Tyr Asp Asp Thr Ile Ser Val Glu Met Lys Lys Glu Asp Phe Asp
        790                 795                 800

ATT TAT GAT GAG GAT GAA AAT CAG AGC CCC CGC AGC TTT CAA AAG AAA                3462
Ile Tyr Asp Glu Asp Glu Asn Gln Ser Pro Arg Ser Phe Gln Lys Lys
    805                 810                 815

ACA CGA CAC TAT TTT ATT GCT GCA GTG GAG AGG CTC TGG GAT TAT GGG                3510
Thr Arg His Tyr Phe Ile Ala Ala Val Glu Arg Leu Trp Asp Tyr Gly
820                 825                 830                 835

ATG AGT AGC TCC CCA CAT GTT CTA AGA AAC AGG GCT CAG AGT GGC AGT                3558
Met Ser Ser Ser Pro His Val Leu Arg Asn Arg Ala Gln Ser Gly Ser
                840                 845                 850

GTC CCT CAG TTC AAG AAA GTT GTT TTC CAG GAA TTT ACT GAT GGC TCC                3606
Val Pro Gln Phe Lys Lys Val Val Phe Gln Glu Phe Thr Asp Gly Ser
            855                 860                 865
```

```
TTT ACT CAG CCC TTA TAC CGT GGA GAA CTA AAT GAA CAT TTG GGA CTC        3654
Phe Thr Gln Pro Leu Tyr Arg Gly Glu Leu Asn Glu His Leu Gly Leu
            870                 875                 880

CTG GGG CCA TAT ATA AGA GCA GAA GTT GAA GAT AAT ATC ATG GTA ACT        3702
Leu Gly Pro Tyr Ile Arg Ala Glu Val Glu Asp Asn Ile Met Val Thr
        885                 890                 895

TTC AGA AAT CAG GCC TCT CGT CCC TAT TCC TTC TAT TCT AGC CTT ATT        3750
Phe Arg Asn Gln Ala Ser Arg Pro Tyr Ser Phe Tyr Ser Ser Leu Ile
900                 905                 910                 915

TCT TAT GAG GAA GAT CAG AGG CAA GGA GCA GAA CCT AGA AAA AAC TTT        3798
Ser Tyr Glu Glu Asp Gln Arg Gln Gly Ala Glu Pro Arg Lys Asn Phe
            920                 925                 930

GTC AAG CCT AAT GAA ACC AAA ACT TAC TTT TGG AAA GTG CAA CAT CAT        3846
Val Lys Pro Asn Glu Thr Lys Thr Tyr Phe Trp Lys Val Gln His His
        935                 940                 945

ATG GCA CCC ACT AAA GAT GAG TTT GAC TGC AAA GCC TGG GCT TAT TTC        3894
Met Ala Pro Thr Lys Asp Glu Phe Asp Cys Lys Ala Trp Ala Tyr Phe
950                 955                 960

TCT GAT GTT GAC CTG GAA AAA GAT GTG CAC TCA GGC CTG ATT GGA CCC        3942
Ser Asp Val Asp Leu Glu Lys Asp Val His Ser Gly Leu Ile Gly Pro
965                 970                 975

CTT CTG GTC TGC CAC ACT AAC ACA CTG AAC CCT GCT CAT GGG AGA CAA        3990
Leu Leu Val Cys His Thr Asn Thr Leu Asn Pro Ala His Gly Arg Gln
980                 985                 990                 995

GTG ACA GTA CAG GAA TTT GCT CTG TTT TTC ACC ATC TTT GAT GAG ACC        4038
Val Thr Val Gln Glu Phe Ala Leu Phe Phe Thr Ile Phe Asp Glu Thr
            1000                1005                1010

AAA AGC TGG TAC TTC ACT GAA AAT ATG GAA AGA AAC TGC AGG GCT CCC        4086
Lys Ser Trp Tyr Phe Thr Glu Asn Met Glu Arg Asn Cys Arg Ala Pro
        1015                1020                1025

TGC AAT ATC CAG ATG GAA GAT CCC ACT TTT AAA GAG AAT TAT CGC TTC        4134
Cys Asn Ile Gln Met Glu Asp Pro Thr Phe Lys Glu Asn Tyr Arg Phe
1030                1035                1040

CAT GCA ATC AAT GGC TAC ATA ATG GAT ACA CTA CCT GGC TTA GTA ATG        4182
His Ala Ile Asn Gly Tyr Ile Met Asp Thr Leu Pro Gly Leu Val Met
            1045                1050                1055

GCT CAG GAT CAA AGG ATT CGA TGG TAT CTG CTC AGC ATG GGC AGC AAT        4230
Ala Gln Asp Gln Arg Ile Arg Trp Tyr Leu Leu Ser Met Gly Ser Asn
1060                1065                1070                1075

GAA AAC ATC CAT TCT ATT CAT TTC AGT GGA CAT GTG TTC ACT GTA CGA        4278
Glu Asn Ile His Ser Ile His Phe Ser Gly His Val Phe Thr Val Arg
            1080                1085                1090

AAA AAA GAG GAG TAT AAA ATG GCA CTG TAC AAT CTC TAT CCA GGT GTT        4326
Lys Lys Glu Glu Tyr Lys Met Ala Leu Tyr Asn Leu Tyr Pro Gly Val
        1095                1100                1105

TTT GAG ACA GTG GAA ATG TTA CCA TCC AAA GCT GGA ATT TGG CGG GTG        4374
Phe Glu Thr Val Glu Met Leu Pro Ser Lys Ala Gly Ile Trp Arg Val
1110                1115                1120

GAA TGC CTT ATT GGC GAG CAT CTA CAT GCT GGG ATG AGC ACA CTT TTT        4422
Glu Cys Leu Ile Gly Glu His Leu His Ala Gly Met Ser Thr Leu Phe
            1125                1130                1135

CTG GTG TAC AGC AAT AAG TGT CAG ACT CCC CTG GGA ATG GCT TCT GGA        4470
Leu Val Tyr Ser Asn Lys Cys Gln Thr Pro Leu Gly Met Ala Ser Gly
1140                1145                1150                1155

CAC ATT AGA GAT TTT CAG ATT ACA GCT TCA GGA CAA TAT GGA CAG TGG        4518
His Ile Arg Asp Phe Gln Ile Thr Ala Ser Gly Gln Tyr Gly Gln Trp
            1160                1165                1170

GCC CCA AAG CTG GCC AGA CTT CAT TAT TCC GGA TCA ATC AAT GCC TGG        4566
Ala Pro Lys Leu Ala Arg Leu His Tyr Ser Gly Ser Ile Asn Ala Trp
        1175                1180                1185
```

```
AGC ACC AAG GAG CCC TTT TCT TGG ATC AAG GTG GAT CTG TTG GCA CCA    4614
Ser Thr Lys Glu Pro Phe Ser Trp Ile Lys Val Asp Leu Leu Ala Pro
            1190                1195                1200

ATG ATT ATT CAC GGC ATC AAG ACC CAG GGT GCC CGT CAG AAG TTC TCC    4662
Met Ile Ile His Gly Ile Lys Thr Gln Gly Ala Arg Gln Lys Phe Ser
        1205                1210                1215

AGC CTC TAC ATC TCT CAG TTT ATC ATC ATG TAT AGT CTT GAT GGG AAG    4710
Ser Leu Tyr Ile Ser Gln Phe Ile Ile Met Tyr Ser Leu Asp Gly Lys
1220                1225                1230                1235

AAG TGG CAG ACT TAT CGA GGA AAT TCC ACT GGA ACC TTA ATG GTC TTC    4758
Lys Trp Gln Thr Tyr Arg Gly Asn Ser Thr Gly Thr Leu Met Val Phe
                1240                1245                1250

TTT GGC AAT GTG GAT TCA TCT GGG ATA AAA CAC AAT ATT TTT AAC CCT    4806
Phe Gly Asn Val Asp Ser Ser Gly Ile Lys His Asn Ile Phe Asn Pro
            1255                1260                1265

CCA ATT ATT GCT CGA TAC ATC CGT TTG CAC CCA ACT CAT TAT AGC ATT    4854
Pro Ile Ile Ala Arg Tyr Ile Arg Leu His Pro Thr His Tyr Ser Ile
        1270                1275                1280

CGC AGC ACT CTT CGC ATG GAG TTG ATG GGC TGT GAT TTA AAT AGT TGC    4902
Arg Ser Thr Leu Arg Met Glu Leu Met Gly Cys Asp Leu Asn Ser Cys
    1285                1290                1295

AGC ATG CCA TTG GGA ATG GAG AGT AAA GCA ATA TCA GAT GCA CAG ATT    4950
Ser Met Pro Leu Gly Met Glu Ser Lys Ala Ile Ser Asp Ala Gln Ile
1300                1305                1310                1315

ACT GCT TCA TCC TAC TTT ACC AAT ATG TTT GCC ACC TGG TCT CCT TCA    4998
Thr Ala Ser Ser Tyr Phe Thr Asn Met Phe Ala Thr Trp Ser Pro Ser
                1320                1325                1330

AAA GCT CGA CTT CAC CTC CAA GGG AGG AGT AAT GCC TGG AGA CCT CAG    5046
Lys Ala Arg Leu His Leu Gln Gly Arg Ser Asn Ala Trp Arg Pro Gln
            1335                1340                1345

GTG AAT AAT CCA AAA GAG TGG CTG CAA GTG GAC TTC CAG AAG ACA ATG    5094
Val Asn Asn Pro Lys Glu Trp Leu Gln Val Asp Phe Gln Lys Thr Met
        1350                1355                1360

AAA GTC ACA GGA GTA ACT ACT CAG GGA GTA AAA TCT CTG CTT ACC AGC    5142
Lys Val Thr Gly Val Thr Thr Gln Gly Val Lys Ser Leu Leu Thr Ser
    1365                1370                1375

ATG TAT GTG AAG GAG TTC CTC ATC TCC AGC AGT CAA GAT GGC CAT CAG    5190
Met Tyr Val Lys Glu Phe Leu Ile Ser Ser Ser Gln Asp Gly His Gln
1380                1385                1390                1395

TGG ACT CTC TTT TTT CAG AAT GGC AAA GTA AAG GTT TTT CAG GGA AAT    5238
Trp Thr Leu Phe Phe Gln Asn Gly Lys Val Lys Val Phe Gln Gly Asn
                1400                1405                1410

CAA GAC TCC TTC ACA CCT GTG GTG AAC TCT CTA GAC CCA CCG TTA CTG    5286
Gln Asp Ser Phe Thr Pro Val Val Asn Ser Leu Asp Pro Pro Leu Leu
            1415                1420                1425

ACT CGC TAC CTT CGA ATT CAC CCC CAG AGT TGG GTG CAC CAG ATT GCC    5334
Thr Arg Tyr Leu Arg Ile His Pro Gln Ser Trp Val His Gln Ile Ala
        1430                1435                1440

CTG AGG ATG GAG GTT CTG GGC TGC GAG GCA CAG GAC CTC TAC             5376
Leu Arg Met Glu Val Leu Gly Cys Glu Ala Gln Asp Leu Tyr
    1445                1450                1455

TGAGGGTGGC CACTGCAGCA CCTGCCACTG CCGTCACCTC TCCCTCCTCA GCTCCAGGGC   5436

AGTGTCCCTC CCTGGCTTGC CTTCTACCTT TGTGCTAAAT CCTAGCAGAC ACTGCCTTGA   5496

AGCCTCCTGA ATTAACTATC ATCAGTCCTG CATTTCTTTG GTGGGGGGCC AGGAGGGTGC   5556

ATCCAATTTA ACTTAACTCT TACCTATTTT CTGCAGCTGC TCCAGATTA CTCCTTCCTT    5616

CCAATATAAC TAGGCAAAAA GAAGTGAGGA GAAACCTGCA TGAAAGCATT CTTCCCTGAA   5676
```

```
AAGTTAGGCC TCTCAGAGTC ACCACTTCCT CTGTTGTAGA AAAACTATGT GATGAAACTT    5736

TGAAAAAGAT ATTTATGATG TTAACTTGTT TATTGCAGCT TATAATGGTT ACAAATAAAG    5796

CAATAGCATC ACAAATTTCA CAAATAAAGC ATTTTTTTCA CTGCATTCTA GTTGTGGTTT    5856

GTCCAAACTC ATCAATGTAT CTTATCATGT CTGGATCCCC GGGTGGCATC CCTGTGACCC    5916

CTCCCCAGTG CCTCTCCTGG CCCTGGAAGT TGCCACTCCA GTGCCCACCA GCCTTGTCCT    5976

AATAAAATTA AGTTGCATCA TTTTGTCTGA CTAGGTGTCC TTCTATAATA TTATGGGGTG    6036

GAGGGGGGTG GTATGGAGCA AGGGGCAAGT TGGGAAGACA ACCTGTAGGG CCTGCGGGGT    6096

CTATTCGGGA ACCAAGCTGG AGTGCAGTGG CACAATCTTG GCTCACTGCA ATCTCCGCCT    6156

CCTGGGTTCA AGCGATTCTC CTGCCTCAGC CTCCCGAGTT GTTGGGATTC CAGGCATGCA    6216

TGACCAGGCT CAGCTAATTT TTGTTTTTTT GGTAGAGACG GGGTTTCACC ATATTGGCCA    6276

GGCTGGTCTC CAACTCCTAA TCTCAGGTGA TCTACCCACC TTGGCCTCCC AAATTGCTGG    6336

GATTACAGGC GTGAACCACT GCTCCCTTCC CTGTCCTTCT GATTTTAAAA TAACTATACC    6396

AGCAGGAGGA CGTCCAGACA CAGCATAGGC TACCTGCCAT GCCCAACCGG TGGGACATTT    6456

GAGTTGCTTG CTTGGCACTG TCCTCTCATG CGTTGGGTCC ACTCAGTAGA TGCCTGTTGA    6516

ATTCGTAATC ATGGTCATAG CTGTTTCCTG TGTGAAATTG TTATCCGCTC ACAATTCCAC    6576

ACAACATACG AGCCGGAAGC ATAAAGTGTA AAGCCTGGGG TGCCTAATGA GTGAGCTAAC    6636

TCACATTAAT TGCGTTGCGC TCACTGCCCG CTTTCCAGTC GGGAAACCTG TCGTGCCAGC    6696

TGCATTAATG AATCGGCCAA CGCGCGGGGA GAGGCGGTTT GCGTATTGGG CGCTCTTCCG    6756

CTTCCTCGCT CACTGACTCG CTGCGCTCGG TCGTTCGGCT GCGGCGAGCG GTATCAGCTC    6816

ACTCAAAGGC GGTAATACGG TTATCCACAG AATCAGGGGA TAACGCAGGA AAGAACATGT    6876

GAGCAAAAGG CCAGCAAAAG GCCAGGAACC GTAAAAAGGC CGCGTTGCTG GCGTTTTTCC    6936

ATAGGCTCCG CCCCCCTGAC GAGCATCACA AAAATCGACG CTCAAGTCAG AGGTGGCGAA    6996

ACCCGACAGG ACTATAAAGA TACCAGGCGT TTCCCCCTGG AAGCTCCCTC GTGCGCTCTC    7056

CTGTTCCGAC CCTGCCGCTT ACCGGATACC TGTCCGCCTT TCTCCCTTCG GGAAGCGTGG    7116

CGCTTTCTCA TAGCTCACGC TGTAGGTATC TCAGTTCGGT GTAGGTCGTT CGCTCCAAGC    7176

TGGGCTGTGT GCACGAACCC CCCGTTCAGC CCGACCGCTG CGCCTTATCC GGTAACTATC    7236

GTCTTGAGTC CAACCCGGTA AGACACGACT TATCGCCACT GGCAGCAGCC ACTGGTAACA    7296

GGATTAGCAG AGCGAGGTAT GTAGGCGGTG CTACAGAGTT CTTGAAGTGG TGGCCTAACT    7356

ACGGCTACAC TAGAAGGACA GTATTTGGTA TCTGCGCTCT GCTGAAGCCA GTTACCTTCG    7416

GAAAAAGAGT TGGTAGCTCT TGATCCGGCA ACAAACCAC CGCTGGTAGC GGTGGTTTTT    7476

TTGTTTGCAA GCAGCAGATT ACGCGCAGAA AAAAAGGATC TCAAGAAGAT CCTTTGATCT    7536

TTTCTACGGG GTCTGACGCT CAGTGGAACG AAAACTCACG TTAAGGGATT TTGGTCATGA    7596

GATTATCAAA AAGGATCTTC ACCTAGATCC TTTTAAATTA AAAATGAAGT TTTAAATCAA    7656

TCTAAAGTAT ATATGAGTAA ACTTGGTCTG ACAGTTACCA ATGCTTAATC AGTGAGGCAC    7716

CTATCTCAGC GATCTGTCTA TTTCGTTCAT CCATAGTTGC CTGACTCCCC GTCGTGTAGA    7776

TAACTACGAT ACGGGAGGGC TTACCATCTG GCCCCAGTGC TGCAATGATA CCGCGAGACC    7836

CACGCTCACC GGCTCCAGAT TTATCAGCAA TAAACCAGCC AGCCGGAAGG GCCGAGCGCA    7896

GAAGTGGTCC TGCAACTTTA TCCGCCTCCA TCCAGTCTAT TAATTGTTGC CGGGAAGCTA    7956

GAGTAAGTAG TTCGCCAGTT AATAGTTTGC GCAACGTTGT TGCCATTGCT ACAGGCATCG    8016

TGGTGTCACG CTCGTCGTTT GGTATGGCTT CATTCAGCTC CGGTTCCCAA CGATCAAGGC    8076
```

```
GAGTTACATG ATCCCCCATG TTGTGCAAAA AAGCGGTTAG CTCCTTCGGT CCTCCGATCG      8136

TTGTCAGAAG TAAGTTGGCC GCAGTGTTAT CACTCATGGT TATGGCAGCA CTGCATAATT      8196

CTCTTACTGT CATGCCATCC GTAAGATGCT TTTCTGTGAC TGGTGAGTAC TCAACCAAGT      8256

CATTCTGAGA ATAGTGTATG CGGCGACCGA GTTGCTCTTG CCCGGCGTCA ATACGGGATA      8316

ATACCGCGCC ACATAGCAGA ACTTTAAAAG TGCTCATCAT TGGAAAACGT TCTTCGGGGC      8376

GAAAACTCTC AAGGATCTTA CCGCTGTTGA GATCCAGTTC GATGTAACCC ACTCGTGCAC      8436

CCAACTGATC TTCAGCATCT TTTACTTTCA CCAGCGTTTC TGGGTGAGCA AAAACAGGAA      8496

GGCAAAATGC CGCAAAAAAG GGAATAAGGG CGACACGGAA ATGTTGAATA CTCATACTCT      8556

TCCTTTTTCA ATATTATTGA AGCATTTATC AGGGTTATTG TCTCATGAGC GGATACATAT      8616

TTGAATGTAT TTAGAAAAAT AAACAAATAG GGGTTCCGCG CACATTTCCC CGAAAAGTGC      8676

CACCTGACGT CTAAGAAACC ATTATTATCA TGACATTAAC CTATAAAAAT AGGCGTATCA      8736

CGAGGCCCTT TCGTCTCGCG CGTTTCGGTG ATGACGGTGA AAACCTCTGA CACATGCAGC      8796

TCCCGGAGAC GGTCACAGCT TGTCTGTAAG CGGATGCCGG GAGCAGACAA GCCCGTCAGG      8856

GCGCGTCAGC GGGTGTTGGC GGGTGTCGGG GCTGGCTTAA CTATGCGGCA TCAGAGCAGA      8916

TTGTACTGAG AGTGCACCAT ATGCGGTGTG AAATACCGCA CAGATGCGTA AGGAGAAAAT      8976

ACCGCATCAG GCGCCATTCG CCATTCAGGC TGCGCAACTG TTGGGAAGGG CGATCGGTGC      9036

GGGCCTCTTC GCTATTACGC CAGCTGGCGA AAGGGGGATG TGCTGCAAGG CGATTAAGTT      9096

GGGTAACGCC AGGGTTTTCC CAGTCACGAC GTTGTAAAAC GACGGCCAGT GCCAAGCTTG      9156

GGCTGCAG                                                              9164

(2) INFORMATION FOR SEQ ID NO:3:

(i) SEQUENCE CHARACTERISTICS:
        (A) LENGTH: 12022 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1006..3294

(ix) FEATURE:
        (A) NAME/KEY: CDS
        (B) LOCATION: 6153..8234

(xi) SEQUENCE DESCRIPTION: SEQ ID NO:3:

GTCGACGGTA TCGATAAGCT TGATATCGAA TTCCTGCAGC CCGGGGATC CACTAGTACT        60

CGAGACCTAG GAGTTAATTT TTAAAAAGCA GTCAAAAGTC CAAGTGGCCC TTGCGAGCAT      120

TTACTCTCTC TGTTTGCTCT GGTTAATAAT CTCAGGAGCA CAAACATTCC TTACTAGTCC      180

TAGAAGTTAA TTTTTAAAAA GCAGTCAAAA GTCCAAGTGG CCCTTGCGAG CATTTACTCT      240

CTCTGTTTGC TCTGGTTAAT AATCTCAGGA GCACAAACAT TCCTTACTAG TTCTAGAGCG      300

GCCGCCAGTG TGCTGGAATT CGGCTTTTTT AGGGCTGGAA GCTACCTTTG ACATCATTTC      360

CTCTGCGAAT GCATGTATAA TTTCTACAGA ACCTATTAGA AAGGATCACC CAGCCTCTGC      420

TTTTGTACAA CTTTCCCTTA AAAAACTGCC AATTCCACTG CTGTTTGGCC AATAGTGAG      480

AACTTTTTCC TGCTGCCTCT TGGTGCTTTT GCCTATGGCC CCTATTCTGC CTGCTGAAGA      540

CACTCTTGCC AGCATGGACT TAAACCCCTC CAGCTCTGAC AATCCTCTTT CTCTTTTGTT      600
```

```
TTACATGAAG GGTCTGGCAG CCAAAGCAAT CACTCAAAGT TCAAACCTTA TCATTTTTTG      660

CTTTGTTCCT CTTGGCCTTG GTTTTGTACA TCAGCTTTGA AAATACCATC CCAGGGTTAA      720

TGCTGGGGTT AATTTATAAC TAAGAGTGCT CTAGTTTTGC AATACAGGAC ATGCTATAAA      780

AATGGAAAGA TGTTGCTTTC TGAGAGATCT CGAGGAAGCT AACAACAAAG AACAACAAAC      840

AACAATCAGG TAAGTATCCT TTTTACAGCA CAACTTAATG AGACAGATAG AAACTGGTCT      900

TGTAGAAACA GAGTAGTCGC CTGCTTTTCT GCCAGGTGCT GACTTCTCTC CCCTTCTCTT      960

TTTTCCTTTT CTCAGGATAA CAAGAACGAA ACAATAACAG CCACC ATG GAA ATA        1014
                                                 Met Glu Ile
                                                  1

GAG CTC TCC ACC TGC TTC TTT CTG TGC CTT TTG CGA TTC TGC TTT AGT       1062
Glu Leu Ser Thr Cys Phe Phe Leu Cys Leu Leu Arg Phe Cys Phe Ser
     5              10                  15

GCC ACC AGA AGA TAC TAC CTG GGT GCA GTG GAA CTG TCA TGG GAC TAT       1110
Ala Thr Arg Arg Tyr Tyr Leu Gly Ala Val Glu Leu Ser Trp Asp Tyr
 20              25                  30                  35

ATG CAA AGT GAT CTC GGT GAG CTG CCT GTG GAC GCA AGA TTT CCT CCT       1158
Met Gln Ser Asp Leu Gly Glu Leu Pro Val Asp Ala Arg Phe Pro Pro
             40                  45                  50

AGA GTG CCA AAA TCT TTT CCA TTC AAC ACC TCA GTC GTG TAC AAA AAG       1206
Arg Val Pro Lys Ser Phe Pro Phe Asn Thr Ser Val Val Tyr Lys Lys
             55                  60                  65

ACT CTG TTT GTA GAA TTC ACG GTT CAC CTT TTC AAC ATC GCT AAG CCA       1254
Thr Leu Phe Val Glu Phe Thr Val His Leu Phe Asn Ile Ala Lys Pro
         70                  75                  80

AGG CCA CCC TGG ATG GGT CTG CTA GGT CCT ACC ATC CAG GCT GAG GTT       1302
Arg Pro Pro Trp Met Gly Leu Leu Gly Pro Thr Ile Gln Ala Glu Val
 85                  90                  95

TAT GAT ACA GTG GTC ATT ACA CTT AAG AAC ATG GCT TCC CAT CCT GTC       1350
Tyr Asp Thr Val Val Ile Thr Leu Lys Asn Met Ala Ser His Pro Val
100                 105                 110                 115

AGT CTT CAT GCT GTT GGT GTA TCC TAC TGG AAA GCT TCT GAG GGA GCT       1398
Ser Leu His Ala Val Gly Val Ser Tyr Trp Lys Ala Ser Glu Gly Ala
                120                 125                 130

GAA TAT GAT GAT CAG ACC AGT CAA AGG GAG AAA GAA GAT GAT AAA GTC       1446
Glu Tyr Asp Asp Gln Thr Ser Gln Arg Glu Lys Glu Asp Asp Lys Val
                135                 140                 145

TTC CCT GGT GGA AGC CAT ACA TAT GTC TGG CAG GTC CTG AAA GAG AAT       1494
Phe Pro Gly Gly Ser His Thr Tyr Val Trp Gln Val Leu Lys Glu Asn
        150                 155                 160

GGT CCA ATG GCC TCT GAC CCA CTG TGC CTT ACC TAC TCA TAT CTT TCT       1542
Gly Pro Met Ala Ser Asp Pro Leu Cys Leu Thr Tyr Ser Tyr Leu Ser
 165                 170                 175

CAT GTG GAC CTG GTA AAA GAC TTG AAT TCA GGC CTC ATT GGA GCC CTA       1590
His Val Asp Leu Val Lys Asp Leu Asn Ser Gly Leu Ile Gly Ala Leu
180                 185                 190                 195

CTA GTA TGT AGA GAA GGG AGT CTG GCC AAG GAA AAG ACA CAG ACC TTG       1638
Leu Val Cys Arg Glu Gly Ser Leu Ala Lys Glu Lys Thr Gln Thr Leu
                200                 205                 210

CAC AAA TTT ATA CTA CTT TTT GCT GTA TTT GAT GAA GGG AAA AGT TGG       1686
His Lys Phe Ile Leu Leu Phe Ala Val Phe Asp Glu Gly Lys Ser Trp
            215                 220                 225

CAC TCA GAA ACA AAG AAC TCC TTG ATG CAG GAT AGG GAT GCT GCA TCT       1734
His Ser Glu Thr Lys Asn Ser Leu Met Gln Asp Arg Asp Ala Ala Ser
            230                 235                 240

GCT CGG GCC TGG CCT AAA ATG CAC ACA GTC AAT GGT TAT GTA AAC AGG       1782
Ala Arg Ala Trp Pro Lys Met His Thr Val Asn Gly Tyr Val Asn Arg
```

```
                    245                 250                 255
TCT CTG CCA GGT CTG ATT GGA TGC CAC AGG AAA TCA GTC TAT TGG CAT        1830
Ser Leu Pro Gly Leu Ile Gly Cys His Arg Lys Ser Val Tyr Trp His
260                 265                 270                 275

GTG ATT GGA ATG GGC ACC ACT CCT GAA GTG CAC TCA ATA TTC CTC GAA        1878
Val Ile Gly Met Gly Thr Thr Pro Glu Val His Ser Ile Phe Leu Glu
                280                 285                 290

GGT CAC ACA TTT CTT GTG AGG AAC CAT CGC CAG GCG TCC TTG GAA ATC        1926
Gly His Thr Phe Leu Val Arg Asn His Arg Gln Ala Ser Leu Glu Ile
            295                 300                 305

TCG CCA ATA ACT TTC CTT ACT GCT CAA ACA CTC TTG ATG GAC CTT GGA        1974
Ser Pro Ile Thr Phe Leu Thr Ala Gln Thr Leu Leu Met Asp Leu Gly
        310                 315                 320

CAG TTT CTA CTG TTT TGT CAT ATC TCT TCC CAC CAA CAT GAT GGC ATG        2022
Gln Phe Leu Leu Phe Cys His Ile Ser Ser His Gln His Asp Gly Met
325                 330                 335

GAA GCT TAT GTC AAA GTA GAC AGC TGT CCA GAG GAA CCC CAA CTA CGA        2070
Glu Ala Tyr Val Lys Val Asp Ser Cys Pro Glu Glu Pro Gln Leu Arg
340                 345                 350                 355

ATG AAA AAT AAT GAA GAA GCG GAA GAC TAT GAT GAT GAT CTT ACT GAT        2118
Met Lys Asn Asn Glu Glu Ala Glu Asp Tyr Asp Asp Asp Leu Thr Asp
                360                 365                 370

TCT GAA ATG GAT GTG GTC AGG TTT GAT GAT GAC AAC TCT CCT TCC TTT        2166
Ser Glu Met Asp Val Val Arg Phe Asp Asp Asp Asn Ser Pro Ser Phe
            375                 380                 385

ATC CAA ATT CGC TCA GTT GCC AAG AAG CAT CCT AAA ACT TGG GTA CAT        2214
Ile Gln Ile Arg Ser Val Ala Lys Lys His Pro Lys Thr Trp Val His
        390                 395                 400

TAC ATT GCT GCT GAA GAG GAG GAC TGG GAC TAT GCT CCC TTA GTC CTC        2262
Tyr Ile Ala Ala Glu Glu Glu Asp Trp Asp Tyr Ala Pro Leu Val Leu
405                 410                 415

GCC CCC GAT GAC AGA AGT TAT AAA AGT CAA TAT TTG AAC AAT GGC CCT        2310
Ala Pro Asp Asp Arg Ser Tyr Lys Ser Gln Tyr Leu Asn Asn Gly Pro
420                 425                 430                 435

CAG CGG ATT GGT AGG AAG TAC AAA AAA GTC CGA TTT ATG GCA TAC ACA        2358
Gln Arg Ile Gly Arg Lys Tyr Lys Lys Val Arg Phe Met Ala Tyr Thr
                440                 445                 450

GAT GAA ACC TTT AAG ACT CGT GAA GCT ATT CAG CAT GAA TCA GGA ATC        2406
Asp Glu Thr Phe Lys Thr Arg Glu Ala Ile Gln His Glu Ser Gly Ile
            455                 460                 465

TTG GGA CCT TTA CTT TAT GGG GAA GTT GGA GAC ACA CTG TTG ATT ATA        2454
Leu Gly Pro Leu Leu Tyr Gly Glu Val Gly Asp Thr Leu Leu Ile Ile
        470                 475                 480

TTT AAG AAT CAA GCA AGC AGA CCA TAT AAC ATC TAC CCT CAC GGA ATC        2502
Phe Lys Asn Gln Ala Ser Arg Pro Tyr Asn Ile Tyr Pro His Gly Ile
485                 490                 495

ACT GAT GTC CGT CCT TTG TAT TCA AGG AGA TTA CCA AAA GGT GTA AAA        2550
Thr Asp Val Arg Pro Leu Tyr Ser Arg Arg Leu Pro Lys Gly Val Lys
500                 505                 510                 515

CAT TTG AAG GAT TTT CCA ATT CTG CCA GGA GAA ATA TTC AAA TAT AAA        2598
His Leu Lys Asp Phe Pro Ile Leu Pro Gly Glu Ile Phe Lys Tyr Lys
                520                 525                 530

TGG ACA GTG ACT GTA GAA GAT GGG CCA ACT AAA TCA GAT CCT CGG TGC        2646
Trp Thr Val Thr Val Glu Asp Gly Pro Thr Lys Ser Asp Pro Arg Cys
            535                 540                 545

CTG ACC CGC TAT TAC TCT AGT TTC GTT AAT ATG GAG AGA GAT CTA GCT        2694
Leu Thr Arg Tyr Tyr Ser Ser Phe Val Asn Met Glu Arg Asp Leu Ala
        550                 555                 560

TCA GGA CTC ATT GGC CCT CTC CTC ATC TGC TAC AAA GAA TCT GTA GAT        2742
```

```
Ser Gly Leu Ile Gly Pro Leu Leu Ile Cys Tyr Lys Glu Ser Val Asp
565                 570                 575

CAA AGA GGA AAC CAG ATA ATG TCA GAC AAG AGG AAT GTC ATC CTG TTT     2790
Gln Arg Gly Asn Gln Ile Met Ser Asp Lys Arg Asn Val Ile Leu Phe
580                 585                 590                 595

TCT GTA TTT GAT GAG AAC CGA AGC TGG TAC CTC ACA GAG AAT ATA CAA     2838
Ser Val Phe Asp Glu Asn Arg Ser Trp Tyr Leu Thr Glu Asn Ile Gln
            600                 605                 610

CGC TTT CTC CCC AAT CCA GCT GGA GTG CAG CTT GAG GAT CCA GAG TTC     2886
Arg Phe Leu Pro Asn Pro Ala Gly Val Gln Leu Glu Asp Pro Glu Phe
                615                 620                 625

CAA GCC TCC AAC ATC ATG CAC AGC ATC AAT GGC TAT GTT TTT GAT AGT     2934
Gln Ala Ser Asn Ile Met His Ser Ile Asn Gly Tyr Val Phe Asp Ser
630                 635                 640

TTG CAG TTG TCA GTT TGT TTG CAT GAG GTG GCA TAC TGG TAC ATT CTA     2982
Leu Gln Leu Ser Val Cys Leu His Glu Val Ala Tyr Trp Tyr Ile Leu
645                 650                 655

AGC ATT GGA GCA CAG ACT GAC TTC CTT TCT GTC TTC TTC TCT GGA TAT     3030
Ser Ile Gly Ala Gln Thr Asp Phe Leu Ser Val Phe Phe Ser Gly Tyr
660                 665                 670                 675

ACC TTC AAA CAC AAA ATG GTC TAT GAA GAC ACA CTC ACC CTA TTC CCA     3078
Thr Phe Lys His Lys Met Val Tyr Glu Asp Thr Leu Thr Leu Phe Pro
            680                 685                 690

TTC TCA GGA GAA ACT GTC TTC ATG TCG ATG GAA AAC CCA GGT CTA TGG     3126
Phe Ser Gly Glu Thr Val Phe Met Ser Met Glu Asn Pro Gly Leu Trp
                695                 700                 705

ATT CTG GGG TGC CAC AAC TCA GAC TTT CGG AAC AGA GGC ATG ACC GCC     3174
Ile Leu Gly Cys His Asn Ser Asp Phe Arg Asn Arg Gly Met Thr Ala
710                 715                 720

TTA CTG AAG GTT TCT AGT TGT GAC AAG AAC ACT GGT GAT TAT TAC GAG     3222
Leu Leu Lys Val Ser Ser Cys Asp Lys Asn Thr Gly Asp Tyr Tyr Glu
725                 730                 735

GAC AGT TAT GAA GAT ATT TCA GCA TAC TTG CTG AGT AAA AAC AAT GCC     3270
Asp Ser Tyr Glu Asp Ile Ser Ala Tyr Leu Leu Ser Lys Asn Asn Ala
740                 745                 750                 755

ATT GAA CCA AGA AGC TTC TCC CAG GTAAGTTATT ATATAAATTC AAGACACCCT    3324
Ile Glu Pro Arg Ser Phe Ser Gln
                760

AGCACTAGGC AAAAGCAATT TAATGCCACC ACAATTCCAG AAAATGACAT AGAGAAGACT   3384

GACCCTTGGT TTGCACACAG AACACCTATG CCTAAAATAC AAAATGTCTC CTCTAGTGAT   3444

TTGTTGATGC TCTTGCGACA GAGTCCTACT CCACATGGGC TATCCTTATC TGATCTCCAA   3504

GAAGCCAAAT ATGAGACTTT TTCTGATGAT CCATCACCTG GAGCAATAGA CAGTAATAAC   3564

AGCCTGTCTG AAATGACACA CTTCAGGCCA CAGCTCCATC ACAGTGGGGA CATGGTATTT   3624

ACCCCTGAGT CAGGCCTCCA ATTAAGATTA AATGAGAAAC TGGGGACAAC TGCAGCAACA   3684

GAGTTGAAGA AACTTGATTT CAAAGTTTCT AGTACATCAA ATAATCTGAT TCAACAATT    3744

CCATCAGACA ATTTGGCAGC AGGTACTGAT AATACAAGTT CCTTAGGACC CCCAAGTATG   3804

CCAGTTCATT ATGATAGTCA ATTAGATACC ACTCTATTTG GCAAAAAGTC ATCTCCCCTT   3864

ACTGAGTCTG GTGGACCTCT GAGCTTGAGT GAAGAAAATA ATGATTCAAA GTTGTTAGAA   3924

TCAGGTTTAA TGAATAGCCA AGAAAGTTCA TGGGGAAAAA ATGTATCGTC AACAGAGAGT   3984

GGTAGGTTAT TTAAAGGGAA AAGAGCTCAT GGACCTGCTT TGTTGACTAA AGATAATGCC   4044

TTATTCAAAG TTAGCATCTC TTTGTTAAAG ACAAACAAAA CTTCCAATAA TTCAGCAACT   4104

AATAGAAAGA CTCACATTGA TGGCCCATCA TTATTAATTG AGAATAGTCC ATCAGTCTGG   4164
```

```
CAAAATATAT TAGAAAGTGA CACTGAGTTT AAAAAAGTGA CACCTTTGAT TCATGACAGA    4224

ATGCTTATGG ACAAAAATGC TACAGCTTTG AGGCTAAATC ATATGTCAAA TAAAACTACT    4284

TCATCAAAAA ACATGGAAAT GGTCCAACAG AAAAAAGAGG GCCCCATTCC ACCAGATGCA    4344

CAAAATCCAG ATATGTCGTT CTTTAAGATG CTATTCTTGC CAGAATCAGC AAGGTGGATA    4404

CAAAGGACTC ATGGAAAGAA CTCTCTGAAC TCTGGGCAAG GCCCCAGTCC AAAGCAATTA    4464

GTATCCTTAG GACCAGAAAA ATCTGTGGAA GGTCAGAATT TCTTGTCTGA GAAAACAAA    4524

GTGGTAGTAG GAAAGGGTGA ATTTACAAAG GACGTAGGAC TCAAAGAGAT GGTTTTTCCA    4584

AGCAGCAGAA ACCTATTTCT TACTAACTTG GATAATTTAC ATGAAAATAA TACACACAAT    4644

CAAGAAAAAA AAATTCAGGA AGAAATAGAA AAGAAGGAAA CATTAATCCA AGAGAATGTA    4704

GTTTTGCCTC AGATACATAC AGTGACTGGC ACTAAGAATT TCATGAAGAA CCTTTTCTTA    4764

CTGAGCACTA GGCAAAATGT AGAAGGTTCA TATGAGGGGG CATATGCTCC AGTACTTCAA    4824

GATTTTAGGT CATTAAATGA TTCAACAAAT AGAACAAAGA AACACACAGC TCATTTCTCA    4884

AAAAAAGGGG AGGAAGAAAA CTTGGAAGGC TTGGGAAATC AAACCAAGCA AATTGTAGAG    4944

AAATATGCAT GCACCACAAG GATATCTCCT AATACAAGCC AGCAGAATTT TGTCACGCAA    5004

CGTAGTAAGA GAGCTTTGAA ACAATTCAGA CTCCCACTAG AAGAAACAGA ACTTGAAAAA    5064

AGGATAATTG TGGATGACAC CTCAACCCAG TGGTCCAAAA ACATGAAACA TTTGACCCCG    5124

AGCACCCTCA CACAGATAGA CTACAATGAG AAGGAGAAAG GGGCCATTAC TCAGTCTCCC    5184

TTATCAGATT GCCTTACGAG GAGTCATAGC ATCCCTCAAG CAAATAGATC TCCATTACCC    5244

ATTGCAAAGG TATCATCATT TCCATCTATT AGACCTATAT ATCTGACCAG GGTCCTATTC    5304

CAAGACAACT CTTCTCATCT TCCAGCAGCA TCTTATAGAA AGAAAGATTC TGGGGTCCAA    5364

GAAAGCAGTC ATTTCTTACA AGGAGCCAAA AAAATAACC TTTCTTTAGC CATTCTAACC    5424

TTGGAGATGA CTGGTGATCA AGAGAGGTT GGCTCCCTGG GGACAAGTGC CACAAATTCA    5484

GTCACATACA AGAAAGTTGA GAACACTGTT CTCCCGAAAC CAGACTTGCC CAAAACATCT    5544

GGCAAAGTTG AATTGCTTCC AAAAGTTCAC ATTTATCAGA AGGACCTATT CCCTACGGAA    5604

ACTAGCAATG GGTCTCCTGG CCATCTGGAT CTCGTGGAAG GGAGCCTTCT TCAGGGAACA    5664

GAGGGAGCGA TTAAGTGGAA TGAAGCAAAC AGACCTGGAA AAGTTCCCTT TCTGAGAGTA    5724

GCAACAGAAA GCTCTGCAAA GACTCCCTCC AAGCTATTGG ATCCTCTTGC TTGGGATAAC    5784

CACTATGGTA CTCAGATACC AAAAGAAGAG TGGAAATCCC AAGAGAAGTC ACCAGAAAAA    5844

ACAGCTTTTA AGAAAAAGGA TACCATTTTG TCCCTGAACG CTTGTGAAAG CAATCATGCA    5904

ATAGCAGCAA TAAATGAGGG ACAAAATAAG CCCGAAATAG AAGTCACCTG GGCAAAGCAA    5964

GGTAGGACTG AAAGGCTGTG CTCTCAATTG TGCTAATAAA GCTTGGCAAG AGTATTTCAA    6024

GGAAGATGAA GTCATTAACT ATGCAAAATG CTTCTCAGGC ACCTAGGAAA ATGAGGATGT    6084

GAGGCATTTC TACCCACTTG GTACATAAAA TTATTGGGTC ACCCTTTTCC TCTTCTTTTT    6144

TTCTCCAG AAC CCA CCA GTC TTG AAA CGC CAT CAA CGG GAA ATA ACT CGT    6194
         Asn Pro Pro Val Leu Lys Arg His Gln Arg Glu Ile Thr Arg
          1               5                  10

ACT ACT CTT CAG TCA GAT CAA GAG GAA ATT GAC TAT GAT GAT ACC ATA    6242
Thr Thr Leu Gln Ser Asp Gln Glu Glu Ile Asp Tyr Asp Asp Thr Ile
 15              20                  25                  30

TCA GTT GAA ATG AAG AAG GAA GAT TTT GAC ATT TAT GAT GAG GAT GAA    6290
Ser Val Glu Met Lys Lys Glu Asp Phe Asp Ile Tyr Asp Glu Asp Glu
             35                  40                  45

AAT CAG AGC CCC CGC AGC TTT CAA AAG AAA ACA CGA CAC TAT TTT ATT    6338
```

-continued

```
            Asn Gln Ser Pro Arg Ser Phe Gln Lys Lys Thr Arg His Tyr Phe Ile
                     50                  55                  60

GCT GCA GTG GAG AGG CTC TGG GAT TAT GGG ATG AGT AGC TCC CCA CAT        6386
Ala Ala Val Glu Arg Leu Trp Asp Tyr Gly Met Ser Ser Ser Pro His
             65                  70                  75

GTT CTA AGA AAC AGG GCT CAG AGT GGC AGT GTC CCT CAG TTC AAG AAA        6434
Val Leu Arg Asn Arg Ala Gln Ser Gly Ser Val Pro Gln Phe Lys Lys
         80                  85                  90

GTT GTT TTC CAG GAA TTT ACT GAT GGC TCC TTT ACT CAG CCC TTA TAC        6482
Val Val Phe Gln Glu Phe Thr Asp Gly Ser Phe Thr Gln Pro Leu Tyr
 95                 100                 105                 110

CGT GGA GAA CTA AAT GAA CAT TTG GGA CTC CTG GGG CCA TAT ATA AGA        6530
Arg Gly Glu Leu Asn Glu His Leu Gly Leu Leu Gly Pro Tyr Ile Arg
                115                 120                 125

GCA GAA GTT GAA GAT AAT ATC ATG GTA ACT TTC AGA AAT CAG GCC TCT        6578
Ala Glu Val Glu Asp Asn Ile Met Val Thr Phe Arg Asn Gln Ala Ser
            130                 135                 140

CGT CCC TAT TCC TTC TAT TCT AGC CTT ATT TCT TAT GAG GAA GAT CAG        6626
Arg Pro Tyr Ser Phe Tyr Ser Ser Leu Ile Ser Tyr Glu Glu Asp Gln
        145                 150                 155

AGG CAA GGA GCA GAA CCT AGA AAA AAC TTT GTC AAG CCT AAT GAA ACC        6674
Arg Gln Gly Ala Glu Pro Arg Lys Asn Phe Val Lys Pro Asn Glu Thr
160                 165                 170

AAA ACT TAC TTT TGG AAA GTG CAA CAT CAT ATG GCA CCC ACT AAA GAT        6722
Lys Thr Tyr Phe Trp Lys Val Gln His His Met Ala Pro Thr Lys Asp
175                 180                 185                 190

GAG TTT GAC TGC AAA GCC TGG GCT TAT TTC TCT GAT GTT GAC CTG GAA        6770
Glu Phe Asp Cys Lys Ala Trp Ala Tyr Phe Ser Asp Val Asp Leu Glu
                195                 200                 205

AAA GAT GTG CAC TCA GGC CTG ATT GGA CCC CTT CTG GTC TGC CAC ACT        6818
Lys Asp Val His Ser Gly Leu Ile Gly Pro Leu Leu Val Cys His Thr
            210                 215                 220

AAC ACA CTG AAC CCT GCT CAT GGG AGA CAA GTG ACA GTA CAG GAA TTT        6866
Asn Thr Leu Asn Pro Ala His Gly Arg Gln Val Thr Val Gln Glu Phe
        225                 230                 235

GCT CTG TTT TTC ACC ATC TTT GAT GAG ACC AAA AGC TGG TAC TTC ACT        6914
Ala Leu Phe Phe Thr Ile Phe Asp Glu Thr Lys Ser Trp Tyr Phe Thr
    240                 245                 250

GAA AAT ATG GAA AGA AAC TGC AGG GCT CCC TGC AAT ATC CAG ATG GAA        6962
Glu Asn Met Glu Arg Asn Cys Arg Ala Pro Cys Asn Ile Gln Met Glu
255                 260                 265                 270

GAT CCC ACT TTT AAA GAG AAT TAT CGC TTC CAT GCA ATC AAT GGC TAC        7010
Asp Pro Thr Phe Lys Glu Asn Tyr Arg Phe His Ala Ile Asn Gly Tyr
                275                 280                 285

ATA ATG GAT ACA CTA CCT GGC TTA GTA ATG GCT CAG GAT CAA AGG ATT        7058
Ile Met Asp Thr Leu Pro Gly Leu Val Met Ala Gln Asp Gln Arg Ile
            290                 295                 300

CGA TGG TAT CTG CTC AGC ATG GGC AGC AAT GAA AAC ATC CAT TCT ATT        7106
Arg Trp Tyr Leu Leu Ser Met Gly Ser Asn Glu Asn Ile His Ser Ile
        305                 310                 315

CAT TTC AGT GGA CAT GTG TTC ACT GTA CGA AAA AAA GAG GAG TAT AAA        7154
His Phe Ser Gly His Val Phe Thr Val Arg Lys Lys Glu Glu Tyr Lys
    320                 325                 330

ATG GCA CTG TAC AAT CTC TAT CCA GGT GTT TTT GAG ACA GTG GAA ATG        7202
Met Ala Leu Tyr Asn Leu Tyr Pro Gly Val Phe Glu Thr Val Glu Met
335                 340                 345                 350

TTA CCA TCC AAA GCT GGA ATT TGG CGG GTG GAA TGC CTT ATT GGC GAG        7250
Leu Pro Ser Lys Ala Gly Ile Trp Arg Val Glu Cys Leu Ile Gly Glu
                355                 360                 365
```

-continued

| | | |
|---|---|---|
| CAT CTA CAT GCT GGG ATG AGC ACA CTT TTT CTG GTG TAC AGC AAT AAG<br>His Leu His Ala Gly Met Ser Thr Leu Phe Leu Val Tyr Ser Asn Lys<br>370 375 380 | | 7298 |
| TGT CAG ACT CCC CTG GGA ATG GCT TCT GGA CAC ATT AGA GAT TTT CAG<br>Cys Gln Thr Pro Leu Gly Met Ala Ser Gly His Ile Arg Asp Phe Gln<br>385 390 395 | | 7346 |
| ATT ACA GCT TCA GGA CAA TAT GGA CAG TGG GCC CCA AAG CTG GCC AGA<br>Ile Thr Ala Ser Gly Gln Tyr Gly Gln Trp Ala Pro Lys Leu Ala Arg<br>400 405 410 | | 7394 |
| CTT CAT TAT TCC GGA TCA ATC AAT GCC TGG AGC ACC AAG GAG CCC TTT<br>Leu His Tyr Ser Gly Ser Ile Asn Ala Trp Ser Thr Lys Glu Pro Phe<br>415 420 425 430 | | 7442 |
| TCT TGG ATC AAG GTG GAT CTG TTG GCA CCA ATG ATT ATT CAC GGC ATC<br>Ser Trp Ile Lys Val Asp Leu Leu Ala Pro Met Ile Ile His Gly Ile<br>435 440 445 | | 7490 |
| AAG ACC CAG GGT GCC CGT CAG AAG TTC TCC AGC CTC TAC ATC TCT CAG<br>Lys Thr Gln Gly Ala Arg Gln Lys Phe Ser Ser Leu Tyr Ile Ser Gln<br>450 455 460 | | 7538 |
| TTT ATC ATC ATG TAT AGT CTT GAT GGG AAG AAG TGG CAG ACT TAT CGA<br>Phe Ile Ile Met Tyr Ser Leu Asp Gly Lys Lys Trp Gln Thr Tyr Arg<br>465 470 475 | | 7586 |
| GGA AAT TCC ACT GGA ACC TTA ATG GTC TTC TTT GGC AAT GTG GAT TCA<br>Gly Asn Ser Thr Gly Thr Leu Met Val Phe Phe Gly Asn Val Asp Ser<br>480 485 490 | | 7634 |
| TCT GGG ATA AAA CAC AAT ATT TTT AAC CCT CCA ATT ATT GCT CGA TAC<br>Ser Gly Ile Lys His Asn Ile Phe Asn Pro Pro Ile Ile Ala Arg Tyr<br>495 500 505 510 | | 7682 |
| ATC CGT TTG CAC CCA ACT CAT TAT AGC ATT CGC AGC ACT CTT CGC ATG<br>Ile Arg Leu His Pro Thr His Tyr Ser Ile Arg Ser Thr Leu Arg Met<br>515 520 525 | | 7730 |
| GAG TTG ATG GGC TGT GAT TTA AAT AGT TGC AGC ATG CCA TTG GGA ATG<br>Glu Leu Met Gly Cys Asp Leu Asn Ser Cys Ser Met Pro Leu Gly Met<br>530 535 540 | | 7778 |
| GAG AGT AAA GCA ATA TCA GAT GCA CAG ATT ACT GCT TCA TCC TAC TTT<br>Glu Ser Lys Ala Ile Ser Asp Ala Gln Ile Thr Ala Ser Ser Tyr Phe<br>545 550 555 | | 7826 |
| ACC AAT ATG TTT GCC ACC TGG TCT CCT TCA AAA GCT CGA CTT CAC CTC<br>Thr Asn Met Phe Ala Thr Trp Ser Pro Ser Lys Ala Arg Leu His Leu<br>560 565 570 | | 7874 |
| CAA GGG AGG AGT AAT GCC TGG AGA CCT CAG GTG AAT AAT CCA AAA GAG<br>Gln Gly Arg Ser Asn Ala Trp Arg Pro Gln Val Asn Asn Pro Lys Glu<br>575 580 585 590 | | 7922 |
| TGG CTG CAA GTG GAC TTC CAG AAG ACA ATG AAA GTC ACA GGA GTA ACT<br>Trp Leu Gln Val Asp Phe Gln Lys Thr Met Lys Val Thr Gly Val Thr<br>595 600 605 | | 7970 |
| ACT CAG GGA GTA AAA TCT CTG CTT ACC AGC ATG TAT GTG AAG GAG TTC<br>Thr Gln Gly Val Lys Ser Leu Leu Thr Ser Met Tyr Val Lys Glu Phe<br>610 615 620 | | 8018 |
| CTC ATC TCC AGC AGT CAA GAT GGC CAT CAG TGG ACT CTC TTT TTT CAG<br>Leu Ile Ser Ser Ser Gln Asp Gly His Gln Trp Thr Leu Phe Phe Gln<br>625 630 635 | | 8066 |
| AAT GGC AAA GTA AAG GTT TTT CAG GGA AAT CAA GAC TCC TTC ACA CCT<br>Asn Gly Lys Val Lys Val Phe Gln Gly Asn Gln Asp Ser Phe Thr Pro<br>640 645 650 | | 8114 |
| GTG GTG AAC TCT CTA GAC CCA CCG TTA CTG ACT CGC TAC CTT CGA ATT<br>Val Val Asn Ser Leu Asp Pro Pro Leu Leu Thr Arg Tyr Leu Arg Ile<br>655 660 665 670 | | 8162 |
| CAC CCC CAG AGT TGG GTG CAC CAG ATT GCC CTG AGG ATG GAG GTT CTG<br>His Pro Gln Ser Trp Val His Gln Ile Ala Leu Arg Met Glu Val Leu<br>675 680 685 | | 8210 |

-continued

```
GGC TGC GAG GCA CAG GAC CTC TAC TGAGGGTGGC CACTGCAGCA CCTGCCACTG    8264
Gly Cys Glu Ala Gln Asp Leu Tyr
                    690
CCGTCACCTC TCCCTCCTCA GCTCCAGGGC AGTGTCCCTC CCTGGCTTGC CTTCTACCTT   8324
TGTGCTAAAT CCTAGCAGAC ACTGCCTTGA AGCCTCCTGA ATTAACTATC ATCAGTCCTG   8384
CATTTCTTTG GTGGGGGGCC AGGAGGGTGC ATCCAATTTA ACTTAACTCT TACCTATTTT   8444
CTGCAGCTGC TCCCAGATTA CTCCTTCCTT CCAATATAAC TAGGCAAAAA GAAGTGAGGA   8504
GAAACCTGCA TGAAAGCATT CTTCCCTGAA AAGTTAGGCC TCTCAGAGTC ACCACTTCCT   8564
CTGTTGTAGA AAAACTATGT GATGAAACTT TGAAAAAGAT ATTTATGATG TTAACTTGTT   8624
TATTGCAGCT TATAATGGTT ACAAATAAAG CAATAGCATC ACAAATTTCA CAAATAAAGC   8684
ATTTTTTTCA CTGCATTCTA GTTGTGGTTT GTCCAAACTC ATCAATGTAT CTTATCATGT   8744
CTGGATCCCC GGGTGGCATC CCTGTGACCC CTCCCCAGTG CCTCTCCTGG CCCTGGAAGT   8804
TGCCACTCCA GTGCCCACCA GCCTTGTCCT AATAAAATTA AGTTGCATCA TTTTGTCTGA   8864
CTAGGTGTCC TTCTATAATA TTATGGGGTG GAGGGGGGTG GTATGGAGCA AGGGGCAAGT   8924
TGGGAAGACA ACCTGTAGGG CCTGCGGGGT CTATTCGGGA ACCAAGCTGG AGTGCAGTGG   8984
CACAATCTTG GCTCACTGCA ATCTCCGCCT CCTGGGTTCA AGCGATTCTC CTGCCTCAGC   9044
CTCCCGAGTT GTTGGGATTC CAGGCATGCA TGACCAGGCT CAGCTAATTT TGTTTTTTT    9104
GGTAGAGACG GGGTTTCACC ATATTGGCCA GGCTGGTCTC CAACTCCTAA TCTCAGGTGA   9164
TCTACCCACC TTGGCCTCCC AAATTGCTGG GATTACAGGC GTGAACCACT GCTCCCTTCC   9224
CTGTCCTTCT GATTTTAAAA TAACTATACC AGCAGGAGGA CGTCCAGACA CAGCATAGGC   9284
TACCTGCCAT GCCCAACCGG TGGGACATTT GAGTTGCTTG CTTGGCACTG TCCTCTCATG   9344
CGTTGGGTCC ACTCAGTAGA TGCCTGTTGA ATTCGTAATC ATGGTCATAG CTGTTTCCTG   9404
TGTGAAATTG TTATCCGCTC ACAATTCCAC ACAACATACG AGCCGGAAGC ATAAAGTGTA   9464
AAGCCTGGGG TGCCTAATGA GTGAGCTAAC TCACATTAAT TGCGTTGCGC TCACTGCCCG   9524
CTTTCCAGTC GGGAAACCTG TCGTGCCAGC TGCATTAATG AATCGGCCAA CGCGCGGGGA   9584
GAGGCGGTTT GCGTATTGGG CGCTCTTCCG CTTCCTCGCT CACTGACTCG CTGCGCTCGG   9644
TCGTTCGGCT GCGGCGAGCG GTATCAGCTC ACTCAAAGGC GGTAATACGG TTATCCACAG   9704
AATCAGGGGA TAACGCAGGA AAGAACATGT GAGCAAAAGG CCAGCAAAAG GCCAGGAACC   9764
GTAAAAAGGC CGCGTTGCTG GCGTTTTTCC ATAGGCTCCG CCCCCCTGAC GAGCATCACA   9824
AAAATCGACG CTCAAGTCAG AGGTGGCGAA ACCCGACAGG ACTATAAAGA TACCAGGCGT   9884
TTCCCCCTGG AAGCTCCCTC GTGCGCTCTC CTGTTCCGAC CCTGCCGCTT ACCGGATACC   9944
TGTCCGCCTT TCTCCCTTCG GGAAGCGTGG CGCTTTCTCA TAGCTCACGC TGTAGGTATC  10004
TCAGTTCGGT GTAGGTCGTT CGCTCCAAGC TGGGCTGTGT GCACGAACCC CCCGTTCAGC  10064
CCGACCGCTG CGCCTTATCC GGTAACTATC GTCTTGAGTC AACCCGGTA AGACACGACT   10124
TATCGCCACT GGCAGCAGCC ACTGGTAACA GGATTAGCAG AGCGAGGTAT GTAGGCGGTG  10184
CTACAGAGTT CTTGAAGTGG TGGCCTAACT ACGGCTACAC TAGAAGGACA GTATTTGGTA  10244
TCTGCGCTCT GCTGAAGCCA GTTACCTTCG GAAAAAGAGT TGGTAGCTCT TGATCCGGCA  10304
AACAAACCAC CGCTGGTAGC GGTGGTTTTT TTGTTTGCAA GCAGCAGATT ACGCGCAGAA  10364
AAAAAGGATC TCAAGAAGAT CCTTTGATCT TTTCTACGGG GTCTGACGCT CAGTGGAACG  10424
AAAACTCACG TTAAGGGATT TTGGTCATGA GATTATCAAA AAGGATCTTC ACCTAGATCC  10484
```

-continued

| | |
|---|---|
| TTTTAAATTA AAAATGAAGT TTTAAATCAA TCTAAAGTAT ATATGAGTAA ACTTGGTCTG | 10544 |
| ACAGTTACCA ATGCTTAATC AGTGAGGCAC CTATCTCAGC GATCTGTCTA TTTCGTTCAT | 10604 |
| CCATAGTTGC CTGACTCCCC GTCGTGTAGA TAACTACGAT ACGGGAGGGC TTACCATCTG | 10664 |
| GCCCCAGTGC TGCAATGATA CCGCGAGACC CACGCTCACC GGCTCCAGAT TTATCAGCAA | 10724 |
| TAAACCAGCC AGCCGGAAGG GCCGAGCGCA GAAGTGGTCC TGCAACTTTA TCCGCCTCCA | 10784 |
| TCCAGTCTAT TAATTGTTGC CGGGAAGCTA GAGTAAGTAG TTCGCCAGTT AATAGTTTGC | 10844 |
| GCAACGTTGT TGCCATTGCT ACAGGCATCG TGGTGTCACG CTCGTCGTTT GGTATGGCTT | 10904 |
| CATTCAGCTC CGGTTCCCAA CGATCAAGGC GAGTTACATG ATCCCCCATG TTGTGCAAAA | 10964 |
| AAGCGGTTAG CTCCTTCGGT CCTCCGATCG TTGTCAGAAG TAAGTTGGCC GCAGTGTTAT | 11024 |
| CACTCATGGT TATGGCAGCA CTGCATAATT CTCTTACTGT CATGCCATCC GTAAGATGCT | 11084 |
| TTTCTGTGAC TGGTGAGTAC TCAACCAAGT CATTCTGAGA ATAGTGTATG CGGCGACCGA | 11144 |
| GTTGCTCTTG CCCGGCGTCA ATACGGGATA ATACCGCGCC ACATAGCAGA ACTTTAAAAG | 11204 |
| TGCTCATCAT TGGAAAACGT TCTTCGGGGC GAAAACTCTC AAGGATCTTA CCGCTGTTGA | 11264 |
| GATCCAGTTC GATGTAACCC ACTCGTGCAC CCAACTGATC TTCAGCATCT TTTACTTTCA | 11324 |
| CCAGCGTTTC TGGGTGAGCA AAAACAGGAA GGCAAAATGC CGCAAAAAAG GGAATAAGGG | 11384 |
| CGACACGGAA ATGTTGAATA CTCATACTCT TCCTTTTTCA ATATTATTGA AGCATTTATC | 11444 |
| AGGGTTATTG TCTCATGAGC GGATACATAT TTGAATGTAT TTAGAAAAAT AAACAAATAG | 11504 |
| GGGTTCCGCG CACATTTCCC CGAAAAGTGC CACCTGACGT CTAAGAAACC ATTATTATCA | 11564 |
| TGACATTAAC CTATAAAAAT AGGCGTATCA CGAGGCCCTT TCGTCTCGCG CGTTTCGGTG | 11624 |
| ATGACGGTGA AAACCTCTGA CACATGCAGC TCCCGGAGAC GGTCACAGCT TGTCTGTAAG | 11684 |
| CGGATGCCGG GAGCAGACAA GCCCGTCAGG GCGCGTCAGC GGGTGTTGGC GGGTGTCGGG | 11744 |
| GCTGGCTTAA CTATGCGGCA TCAGAGCAGA TTGTACTGAG AGTGCACCAT ATGCGGTGTG | 11804 |
| AAATACCGCA CAGATGCGTA AGGAGAAAAT ACCGCATCAG GCGCCATTCG CCATTCAGGC | 11864 |
| TGCGCAACTG TTGGGAAGGG CGATCGGTGC GGGCCTCTTC GCTATTACGC CAGCTGGCGA | 11924 |
| AAGGGGGATG TGCTGCAAGG CGATTAAGTT GGGTAACGCC AGGGTTTTCC CAGTCACGAC | 11984 |
| GTTGTAAAAC GACGGCCAGT GCCAAGCTTG GGCTGCAG | 12022 |

(2) INFORMATION FOR SEQ ID NO:4:

(i) SEQUENCE CHARACTERISTICS:
        (A) LENGTH: 11846 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1006..8058

(xi) SEQUENCE DESCRIPTION: SEQ ID NO:4:

| | |
|---|---|
| GTCGACGGTA TCGATAAGCT TGATATCGAA TTCCTGCAGC CCGGGGATCC CACTAGTACT | 60 |
| CGAGACCTAG GAGTTAATTT TTAAAAAGCA GTCAAAAGTC CAAGTGGCCC TTGCGAGCAT | 120 |
| TTACTCTCTC TGTTTGCTCT GGTTAATAAT CTCAGGAGCA CAAACATTCC TTACTAGTCC | 180 |
| TAGAAGTTAA TTTTTAAAAA GCAGTCAAAA GTCCAAGTGG CCCTTGCGAG CATTTACTCT | 240 |
| CTCTGTTTGC TCTGGTTAAT AATCTCAGGA GCACAAACAT TCCTTACTAG TTCTAGAGCG | 300 |

-continued

```
GCCGCCAGTG TGCTGGAATT CGGCTTTTTT AGGGCTGGAA GCTACCTTTG ACATCATTTC    360

CTCTGCGAAT GCATGTATAA TTTCTACAGA ACCTATTAGA AAGGATCACC CAGCCTCTGC    420

TTTTGTACAA CTTTCCCTTA AAAAACTGCC AATTCCACTG CTGTTTGGCC CAATAGTGAG    480

AACTTTTTCC TGCTGCCTCT TGGTGCTTTT GCCTATGGCC CCTATTCTGC CTGCTGAAGA    540

CACTCTTGCC AGCATGGACT TAAACCCCTC CAGCTCTGAC AATCCTCTTT CTCTTTTGTT    600

TTACATGAAG GGTCTGGCAG CCAAAGCAAT CACTCAAAGT TCAAACCTTA TCATTTTTTG    660

CTTTGTTCCT CTTGGCCTTG GTTTTGTACA TCAGCTTTGA AAATACCATC CCAGGGTTAA    720

TGCTGGGGTT AATTTATAAC TAAGAGTGCT CTAGTTTTGC AATACAGGAC ATGCTATAAA    780

AATGGAAAGA TGTTGCTTTC TGAGAGATCT CGAGGAAGCT AACAACAAAG AACAACAAAC    840

AACAATCAGG TAAGTATCCT TTTTACAGCA CAACTTAATG AGACAGATAG AAACTGGTCT    900

TGTAGAAACA GAGTAGTCGC CTGCTTTTCT GCCAGGTGCT GACTTCTCTC CCCTTCTCTT    960

TTTTCCTTTT CTCAGGATAA CAAGAACGAA ACAATAACAG CCACC ATG GAA ATA      1014
                                                  Met Glu Ile
                                                    1

GAG CTC TCC ACC TGC TTC TTT CTG TGC CTT TTG CGA TTC TGC TTT AGT    1062
Glu Leu Ser Thr Cys Phe Phe Leu Cys Leu Leu Arg Phe Cys Phe Ser
      5                  10                  15

GCC ACC AGA AGA TAC TAC CTG GGT GCA GTG GAA CTG TCA TGG GAC TAT    1110
Ala Thr Arg Arg Tyr Tyr Leu Gly Ala Val Glu Leu Ser Trp Asp Tyr
 20                  25                  30                  35

ATG CAA AGT GAT CTC GGT GAG CTG CCT GTG GAC GCA AGA TTT CCT CCT    1158
Met Gln Ser Asp Leu Gly Glu Leu Pro Val Asp Ala Arg Phe Pro Pro
              40                  45                  50

AGA GTG CCA AAA TCT TTT CCA TTC AAC ACC TCA GTC GTG TAC AAA AAG    1206
Arg Val Pro Lys Ser Phe Pro Phe Asn Thr Ser Val Val Tyr Lys Lys
          55                  60                  65

ACT CTG TTT GTA GAA TTC ACG GTT CAC CTT TTC AAC ATC GCT AAG CCA    1254
Thr Leu Phe Val Glu Phe Thr Val His Leu Phe Asn Ile Ala Lys Pro
      70                  75                  80

AGG CCA CCC TGG ATG GGT CTG CTA GGT CCT ACC ATC CAG GCT GAG GTT    1302
Arg Pro Pro Trp Met Gly Leu Leu Gly Pro Thr Ile Gln Ala Glu Val
 85                  90                  95

TAT GAT ACA GTG GTC ATT ACA CTT AAG AAC ATG GCT TCC CAT CCT GTC    1350
Tyr Asp Thr Val Val Ile Thr Leu Lys Asn Met Ala Ser His Pro Val
100                 105                 110                 115

AGT CTT CAT GCT GTT GGT GTA TCC TAC TGG AAA GCT TCT GAG GGA GCT    1398
Ser Leu His Ala Val Gly Val Ser Tyr Trp Lys Ala Ser Glu Gly Ala
              120                 125                 130

GAA TAT GAT GAT CAG ACC AGT CAA AGG GAG AAA GAA GAT GAT AAA GTC    1446
Glu Tyr Asp Asp Gln Thr Ser Gln Arg Glu Lys Glu Asp Asp Lys Val
          135                 140                 145

TTC CCT GGT GGA AGC CAT ACA TAT GTC TGG CAG GTC CTG AAA GAG AAT    1494
Phe Pro Gly Gly Ser His Thr Tyr Val Trp Gln Val Leu Lys Glu Asn
     150                 155                 160

GGT CCA ATG GCC TCT GAC CCA CTG TGC CTT ACC TAC TCA TAT CTT TCT    1542
Gly Pro Met Ala Ser Asp Pro Leu Cys Leu Thr Tyr Ser Tyr Leu Ser
 165                 170                 175

CAT GTG GAC CTG GTA AAA GAC TTG AAT TCA GGC CTC ATT GGA GCC CTA    1590
His Val Asp Leu Val Lys Asp Leu Asn Ser Gly Leu Ile Gly Ala Leu
180                 185                 190                 195

CTA GTA TGT AGA GAA GGG AGT CTG GCC AAG GAA AAG ACA CAG ACC TTG    1638
Leu Val Cys Arg Glu Gly Ser Leu Ala Lys Glu Lys Thr Gln Thr Leu
              200                 205                 210

CAC AAA TTT ATA CTA CTT TTT GCT GTA TTT GAT GAA GGG AAA AGT TGG    1686
```

```
                                                          -continued

His Lys Phe Ile Leu Leu Phe Ala Val Phe Asp Glu Gly Lys Ser Trp
            215                 220                 225

CAC TCA GAA ACA AAG AAC TCC TTG ATG CAG GAT AGG GAT GCT GCA TCT      1734
His Ser Glu Thr Lys Asn Ser Leu Met Gln Asp Arg Asp Ala Ala Ser
            230                 235                 240

GCT CGG GCC TGG CCT AAA ATG CAC ACA GTC AAT GGT TAT GTA AAC AGG      1782
Ala Arg Ala Trp Pro Lys Met His Thr Val Asn Gly Tyr Val Asn Arg
245                 250                 255

TCT CTG CCA GGT CTG ATT GGA TGC CAC AGG AAA TCA GTC TAT TGG CAT      1830
Ser Leu Pro Gly Leu Ile Gly Cys His Arg Lys Ser Val Tyr Trp His
260                 265                 270                 275

GTG ATT GGA ATG GGC ACC ACT CCT GAA GTG CAC TCA ATA TTC CTC GAA      1878
Val Ile Gly Met Gly Thr Thr Pro Glu Val His Ser Ile Phe Leu Glu
                280                 285                 290

GGT CAC ACA TTT CTT GTG AGG AAC CAT CGC CAG GCG TCC TTG GAA ATC      1926
Gly His Thr Phe Leu Val Arg Asn His Arg Gln Ala Ser Leu Glu Ile
                295                 300                 305

TCG CCA ATA ACT TTC CTT ACT GCT CAA ACA CTC TTG ATG GAC CTT GGA      1974
Ser Pro Ile Thr Phe Leu Thr Ala Gln Thr Leu Leu Met Asp Leu Gly
                310                 315                 320

CAG TTT CTA CTG TTT TGT CAT ATC TCT TCC CAC CAA CAT GAT GGC ATG      2022
Gln Phe Leu Leu Phe Cys His Ile Ser Ser His Gln His Asp Gly Met
            325                 330                 335

GAA GCT TAT GTC AAA GTA GAC AGC TGT CCA GAG GAA CCC CAA CTA CGA      2070
Glu Ala Tyr Val Lys Val Asp Ser Cys Pro Glu Glu Pro Gln Leu Arg
340                 345                 350                 355

ATG AAA AAT AAT GAA GAA GCG GAA GAC TAT GAT GAT GAT CTT ACT GAT      2118
Met Lys Asn Asn Glu Glu Ala Glu Asp Tyr Asp Asp Asp Leu Thr Asp
                360                 365                 370

TCT GAA ATG GAT GTG GTC AGG TTT GAT GAT GAC AAC TCT CCT TCC TTT      2166
Ser Glu Met Asp Val Val Arg Phe Asp Asp Asp Asn Ser Pro Ser Phe
                375                 380                 385

ATC CAA ATT CGC TCA GTT GCC AAG AAG CAT CCT AAA ACT TGG GTA CAT      2214
Ile Gln Ile Arg Ser Val Ala Lys Lys His Pro Lys Thr Trp Val His
                390                 395                 400

TAC ATT GCT GCT GAA GAG GAG GAC TGG GAC TAT GCT CCC TTA GTC CTC      2262
Tyr Ile Ala Ala Glu Glu Glu Asp Trp Asp Tyr Ala Pro Leu Val Leu
            405                 410                 415

GCC CCC GAT GAC AGA AGT TAT AAA AGT CAA TAT TTG AAC AAT GGC CCT      2310
Ala Pro Asp Asp Arg Ser Tyr Lys Ser Gln Tyr Leu Asn Asn Gly Pro
420                 425                 430                 435

CAG CGG ATT GGT AGG AAG TAC AAA AAA GTC CGA TTT ATG GCA TAC ACA      2358
Gln Arg Ile Gly Arg Lys Tyr Lys Lys Val Arg Phe Met Ala Tyr Thr
                440                 445                 450

GAT GAA ACC TTT AAG ACT CGT GAA GCT ATT CAG CAT GAA TCA GGA ATC      2406
Asp Glu Thr Phe Lys Thr Arg Glu Ala Ile Gln His Glu Ser Gly Ile
            455                 460                 465

TTG GGA CCT TTA CTT TAT GGG GAA GTT GGA GAC ACA CTG TTG ATT ATA      2454
Leu Gly Pro Leu Leu Tyr Gly Glu Val Gly Asp Thr Leu Leu Ile Ile
            470                 475                 480

TTT AAG AAT CAA GCA AGC AGA CCA TAT AAC ATC TAC CCT CAC GGA ATC      2502
Phe Lys Asn Gln Ala Ser Arg Pro Tyr Asn Ile Tyr Pro His Gly Ile
            485                 490                 495

ACT GAT GTC CGT CCT TTG TAT TCA AGG AGA TTA CCA AAA GGT GTA AAA      2550
Thr Asp Val Arg Pro Leu Tyr Ser Arg Arg Leu Pro Lys Gly Val Lys
500                 505                 510                 515

CAT TTG AAG GAT TTT CCA ATT CTG CCA GGA GAA ATA TTC AAA TAT AAA      2598
His Leu Lys Asp Phe Pro Ile Leu Pro Gly Glu Ile Phe Lys Tyr Lys
            520                 525                 530
```

```
TGG ACA GTG ACT GTA GAA GAT GGG CCA ACT AAA TCA GAT CCT CGG TGC       2646
Trp Thr Val Thr Val Glu Asp Gly Pro Thr Lys Ser Asp Pro Arg Cys
            535                 540                 545

CTG ACC CGC TAT TAC TCT AGT TTC GTT AAT ATG GAG AGA GAT CTA GCT       2694
Leu Thr Arg Tyr Tyr Ser Ser Phe Val Asn Met Glu Arg Asp Leu Ala
        550                 555                 560

TCA GGA CTC ATT GGC CCT CTC CTC ATC TGC TAC AAA GAA TCT GTA GAT       2742
Ser Gly Leu Ile Gly Pro Leu Leu Ile Cys Tyr Lys Glu Ser Val Asp
565                 570                 575

CAA AGA GGA AAC CAG ATA ATG TCA GAC AAG AGG AAT GTC ATC CTG TTT       2790
Gln Arg Gly Asn Gln Ile Met Ser Asp Lys Arg Asn Val Ile Leu Phe
580                 585                 590                 595

TCT GTA TTT GAT GAG AAC CGA AGC TGG TAC CTC ACA GAG AAT ATA CAA       2838
Ser Val Phe Asp Glu Asn Arg Ser Trp Tyr Leu Thr Glu Asn Ile Gln
                600                 605                 610

CGC TTT CTC CCC AAT CCA GCT GGA GTG CAG CTT GAG GAT CCA GAG TTC       2886
Arg Phe Leu Pro Asn Pro Ala Gly Val Gln Leu Glu Asp Pro Glu Phe
            615                 620                 625

CAA GCC TCC AAC ATC ATG CAC AGC ATC AAT GGC TAT GTT TTT GAT AGT       2934
Gln Ala Ser Asn Ile Met His Ser Ile Asn Gly Tyr Val Phe Asp Ser
        630                 635                 640

TTG CAG TTG TCA GTT TGT TTG CAT GAG GTG GCA TAC TGG TAC ATT CTA       2982
Leu Gln Leu Ser Val Cys Leu His Glu Val Ala Tyr Trp Tyr Ile Leu
645                 650                 655

AGC ATT GGA GCA CAG ACT GAC TTC CTT TCT GTC TTC TTC TCT GGA TAT       3030
Ser Ile Gly Ala Gln Thr Asp Phe Leu Ser Val Phe Phe Ser Gly Tyr
660                 665                 670                 675

ACC TTC AAA CAC AAA ATG GTC TAT GAA GAC ACA CTC ACC CTA TTC CCA       3078
Thr Phe Lys His Lys Met Val Tyr Glu Asp Thr Leu Thr Leu Phe Pro
                680                 685                 690

TTC TCA GGA GAA ACT GTC TTC ATG TCG ATG GAA AAC CCA GGT CTA TGG       3126
Phe Ser Gly Glu Thr Val Phe Met Ser Met Glu Asn Pro Gly Leu Trp
            695                 700                 705

ATT CTG GGG TGC CAC AAC TCA GAC TTT CGG AAC AGA GGC ATG ACC GCC       3174
Ile Leu Gly Cys His Asn Ser Asp Phe Arg Asn Arg Gly Met Thr Ala
        710                 715                 720

TTA CTG AAG GTT TCT AGT TGT GAC AAG AAC ACT GGT GAT TAT TAC GAG       3222
Leu Leu Lys Val Ser Ser Cys Asp Lys Asn Thr Gly Asp Tyr Tyr Glu
725                 730                 735

GAC AGT TAT GAA GAT ATT TCA GCA TAC TTG CTG AGT AAA AAC AAT GCC       3270
Asp Ser Tyr Glu Asp Ile Ser Ala Tyr Leu Leu Ser Lys Asn Asn Ala
740                 745                 750                 755

ATT GAA CCA AGA AGC TTC TCC CAG AAT TCA AGA CAC CCT AGC ACT AGG       3318
Ile Glu Pro Arg Ser Phe Ser Gln Asn Ser Arg His Pro Ser Thr Arg
                760                 765                 770

CAA AAG CAA TTT AAT GCC ACC ACA ATT CCA GAA AAT GAC ATA GAG AAG       3366
Gln Lys Gln Phe Asn Ala Thr Thr Ile Pro Glu Asn Asp Ile Glu Lys
            775                 780                 785

ACT GAC CCT TGG TTT GCA CAC AGA ACA CCT ATG CCT AAA ATA CAA AAT       3414
Thr Asp Pro Trp Phe Ala His Arg Thr Pro Met Pro Lys Ile Gln Asn
        790                 795                 800

GTC TCC TCT AGT GAT TTG TTG ATG CTC TTG CGA CAG AGT CCT ACT CCA       3462
Val Ser Ser Ser Asp Leu Leu Met Leu Leu Arg Gln Ser Pro Thr Pro
805                 810                 815

CAT GGG CTA TCC TTA TCT GAT CTC CAA GAA GCC AAA TAT GAG ACT TTT       3510
His Gly Leu Ser Leu Ser Asp Leu Gln Glu Ala Lys Tyr Glu Thr Phe
820                 825                 830                 835

TCT GAT GAT CCA TCA CCT GGA GCA ATA GAC AGT AAT AAC AGC CTG TCT       3558
Ser Asp Asp Pro Ser Pro Gly Ala Ile Asp Ser Asn Asn Ser Leu Ser
                840                 845                 850
```

```
GAA ATG ACA CAC TTC AGG CCA CAG CTC CAT CAC AGT GGG GAC ATG GTA      3606
Glu Met Thr His Phe Arg Pro Gln Leu His His Ser Gly Asp Met Val
            855                 860                 865

TTT ACC CCT GAG TCA GGC CTC CAA TTA AGA TTA AAT GAG AAA CTG GGG      3654
Phe Thr Pro Glu Ser Gly Leu Gln Leu Arg Leu Asn Glu Lys Leu Gly
            870                 875                 880

ACA ACT GCA GCA ACA GAG TTG AAG AAA CTT GAT TTC AAA GTT TCT AGT      3702
Thr Thr Ala Ala Thr Glu Leu Lys Lys Leu Asp Phe Lys Val Ser Ser
            885                 890                 895

ACA TCA AAT AAT CTG ATT TCA ACA ATT CCA TCA GAC AAT TTG GCA GCA      3750
Thr Ser Asn Asn Leu Ile Ser Thr Ile Pro Ser Asp Asn Leu Ala Ala
900                 905                 910                 915

GGT ACT GAT AAT ACA AGT TCC TTA GGA CCC CCA AGT ATG CCA GTT CAT      3798
Gly Thr Asp Asn Thr Ser Ser Leu Gly Pro Pro Ser Met Pro Val His
            920                 925                 930

TAT GAT AGT CAA TTA GAT ACC ACT CTA TTT GGC AAA AAG TCA TCT CCC      3846
Tyr Asp Ser Gln Leu Asp Thr Thr Leu Phe Gly Lys Lys Ser Ser Pro
            935                 940                 945

CTT ACT GAG TCT GGT GGA CCT CTG AGC TTG AGT GAA GAA AAT AAT GAT      3894
Leu Thr Glu Ser Gly Gly Pro Leu Ser Leu Ser Glu Glu Asn Asn Asp
            950                 955                 960

TCA AAG TTG TTA GAA TCA GGT TTA ATG AAT AGC CAA GAA AGT TCA TGG      3942
Ser Lys Leu Leu Glu Ser Gly Leu Met Asn Ser Gln Glu Ser Ser Trp
            965                 970                 975

GGA AAA AAT GTA TCG TCA ACA GAG AGT GGT AGG TTA TTT AAA GGG AAA      3990
Gly Lys Asn Val Ser Ser Thr Glu Ser Gly Arg Leu Phe Lys Gly Lys
980                 985                 990                 995

AGA GCT CAT GGA CCT GCT TTG TTG ACT AAA GAT AAT GCC TTA TTC AAA      4038
Arg Ala His Gly Pro Ala Leu Leu Thr Lys Asp Asn Ala Leu Phe Lys
            1000                1005                1010

GTT AGC ATC TCT TTG TTA AAG ACA AAC AAA ACT TCC AAT AAT TCA GCA      4086
Val Ser Ile Ser Leu Leu Lys Thr Asn Lys Thr Ser Asn Asn Ser Ala
            1015                1020                1025

ACT AAT AGA AAG ACT CAC ATT GAT GGC CCA TCA TTA TTA ATT GAG AAT      4134
Thr Asn Arg Lys Thr His Ile Asp Gly Pro Ser Leu Leu Ile Glu Asn
            1030                1035                1040

AGT CCA TCA GTC TGG CAA AAT ATA TTA GAA AGT GAC ACT GAG TTT AAA      4182
Ser Pro Ser Val Trp Gln Asn Ile Leu Glu Ser Asp Thr Glu Phe Lys
            1045                1050                1055

AAA GTG ACA CCT TTG ATT CAT GAC AGA ATG CTT ATG GAC AAA AAT GCT      4230
Lys Val Thr Pro Leu Ile His Asp Arg Met Leu Met Asp Lys Asn Ala
1060                1065                1070                1075

ACA GCT TTG AGG CTA AAT CAT ATG TCA AAT AAA ACT ACT TCA TCA AAA      4278
Thr Ala Leu Arg Leu Asn His Met Ser Asn Lys Thr Thr Ser Ser Lys
            1080                1085                1090

AAC ATG GAA ATG GTC CAA CAG AAA AAA GAG GGC CCC ATT CCA CCA GAT      4326
Asn Met Glu Met Val Gln Gln Lys Lys Glu Gly Pro Ile Pro Pro Asp
            1095                1100                1105

GCA CAA AAT CCA GAT ATG TCG TTC TTT AAG ATG CTA TTC TTG CCA GAA      4374
Ala Gln Asn Pro Asp Met Ser Phe Phe Lys Met Leu Phe Leu Pro Glu
            1110                1115                1120

TCA GCA AGG TGG ATA CAA AGG ACT CAT GGA AAG AAC TCT CTG AAC TCT      4422
Ser Ala Arg Trp Ile Gln Arg Thr His Gly Lys Asn Ser Leu Asn Ser
            1125                1130                1135

GGG CAA GGC CCC AGT CCA AAG CAA TTA GTA TCC TTA GGA CCA GAA AAA      4470
Gly Gln Gly Pro Ser Pro Lys Gln Leu Val Ser Leu Gly Pro Glu Lys
1140                1145                1150                1155

TCT GTG GAA GGT CAG AAT TTC TTG TCT GAG AAA AAC AAA GTG GTA GTA      4518
Ser Val Glu Gly Gln Asn Phe Leu Ser Glu Lys Asn Lys Val Val Val
```

-continued

```
              1160               1165               1170
GGA AAG GGT GAA TTT ACA AAG GAC GTA GGA CTC AAA GAG ATG GTT TTT      4566
Gly Lys Gly Glu Phe Thr Lys Asp Val Gly Leu Lys Glu Met Val Phe
            1175               1180               1185

CCA AGC AGC AGA AAC CTA TTT CTT ACT AAC TTG GAT AAT TTA CAT GAA      4614
Pro Ser Ser Arg Asn Leu Phe Leu Thr Asn Leu Asp Asn Leu His Glu
            1190               1195               1200

AAT AAT ACA CAC AAT CAA GAA AAA AAA ATT CAG GAA GAA ATA GAA AAG      4662
Asn Asn Thr His Asn Gln Glu Lys Lys Ile Gln Glu Glu Ile Glu Lys
            1205               1210               1215

AAG GAA ACA TTA ATC CAA GAG AAT GTA GTT TTG CCT CAG ATA CAT ACA      4710
Lys Glu Thr Leu Ile Gln Glu Asn Val Val Leu Pro Gln Ile His Thr
1220               1225               1230               1235

GTG ACT GGC ACT AAG AAT TTC ATG AAG AAC CTT TTC TTA CTG AGC ACT      4758
Val Thr Gly Thr Lys Asn Phe Met Lys Asn Leu Phe Leu Leu Ser Thr
            1240               1245               1250

AGG CAA AAT GTA GAA GGT TCA TAT GAG GGG GCA TAT GCT CCA GTA CTT      4806
Arg Gln Asn Val Glu Gly Ser Tyr Glu Gly Ala Tyr Ala Pro Val Leu
            1255               1260               1265

CAA GAT TTT AGG TCA TTA AAT GAT TCA ACA AAT AGA ACA AAG AAA CAC      4854
Gln Asp Phe Arg Ser Leu Asn Asp Ser Thr Asn Arg Thr Lys Lys His
            1270               1275               1280

ACA GCT CAT TTC TCA AAA AAA GGG GAG GAA GAA AAC TTG GAA GGC TTG      4902
Thr Ala His Phe Ser Lys Lys Gly Glu Glu Glu Asn Leu Glu Gly Leu
            1285               1290               1295

GGA AAT CAA ACC AAG CAA ATT GTA GAG AAA TAT GCA TGC ACC ACA AGG      4950
Gly Asn Gln Thr Lys Gln Ile Val Glu Lys Tyr Ala Cys Thr Thr Arg
1300               1305               1310               1315

ATA TCT CCT AAT ACA AGC CAG CAG AAT TTT GTC ACG CAA CGT AGT AAG      4998
Ile Ser Pro Asn Thr Ser Gln Gln Asn Phe Val Thr Gln Arg Ser Lys
            1320               1325               1330

AGA GCT TTG AAA CAA TTC AGA CTC CCA CTA GAA GAA ACA GAA CTT GAA      5046
Arg Ala Leu Lys Gln Phe Arg Leu Pro Leu Glu Glu Thr Glu Leu Glu
            1335               1340               1345

AAA AGG ATA ATT GTG GAT GAC ACC TCA ACC CAG TGG TCC AAA AAC ATG      5094
Lys Arg Ile Ile Val Asp Asp Thr Ser Thr Gln Trp Ser Lys Asn Met
            1350               1355               1360

AAA CAT TTG ACC CCG AGC ACC CTC ACA CAG ATA GAC TAC AAT GAG AAG      5142
Lys His Leu Thr Pro Ser Thr Leu Thr Gln Ile Asp Tyr Asn Glu Lys
            1365               1370               1375

GAG AAA GGG GCC ATT ACT CAG TCT CCC TTA TCA GAT TGC CTT ACG AGG      5190
Glu Lys Gly Ala Ile Thr Gln Ser Pro Leu Ser Asp Cys Leu Thr Arg
1380               1385               1390               1395

AGT CAT AGC ATC CCT CAA GCA AAT AGA TCT CCA TTA CCC ATT GCA AAG      5238
Ser His Ser Ile Pro Gln Ala Asn Arg Ser Pro Leu Pro Ile Ala Lys
            1400               1405               1410

GTA TCA TCA TTT CCA TCT ATT AGA CCT ATA TAT CTG ACC AGG GTC CTA      5286
Val Ser Ser Phe Pro Ser Ile Arg Pro Ile Tyr Leu Thr Arg Val Leu
            1415               1420               1425

TTC CAA GAC AAC TCT TCT CAT CTT CCA GCA GCA TCT TAT AGA AAG AAA      5334
Phe Gln Asp Asn Ser Ser His Leu Pro Ala Ala Ser Tyr Arg Lys Lys
            1430               1435               1440

GAT TCT GGG GTC CAA GAA AGC AGT CAT TTC TTA CAA GGA GCC AAA AAA      5382
Asp Ser Gly Val Gln Glu Ser Ser His Phe Leu Gln Gly Ala Lys Lys
            1445               1450               1455

AAT AAC CTT TCT TTA GCC ATT CTA ACC TTG GAG ATG ACT GGT GAT CAA      5430
Asn Asn Leu Ser Leu Ala Ile Leu Thr Leu Glu Met Thr Gly Asp Gln
1460               1465               1470               1475

AGA GAG GTT GGC TCC CTG GGG ACA AGT GCC ACA AAT TCA GTC ACA TAC      5478
```

```
                                                                    -continued Arg Glu Val Gly Ser Leu Gly Thr Ser Ala Thr Asn Ser Val Thr Tyr
            1480                1485                1490

AAG AAA GTT GAG AAC ACT GTT CTC CCG AAA CCA GAC TTG CCC AAA ACA     5526
Lys Lys Val Glu Asn Thr Val Leu Pro Lys Pro Asp Leu Pro Lys Thr
            1495                1500                1505

TCT GGC AAA GTT GAA TTG CTT CCA AAA GTT CAC ATT TAT CAG AAG GAC     5574
Ser Gly Lys Val Glu Leu Leu Pro Lys Val His Ile Tyr Gln Lys Asp
            1510                1515                1520

CTA TTC CCT ACG GAA ACT AGC AAT GGG TCT CCT GGC CAT CTG GAT CTC     5622
Leu Phe Pro Thr Glu Thr Ser Asn Gly Ser Pro Gly His Leu Asp Leu
    1525                1530                1535

GTG GAA GGG AGC CTT CTT CAG GGA ACA GAG GGA GCG ATT AAG TGG AAT     5670
Val Glu Gly Ser Leu Leu Gln Gly Thr Glu Gly Ala Ile Lys Trp Asn
1540                1545                1550                1555

GAA GCA AAC AGA CCT GGA AAA GTT CCC TTT CTG AGA GTA GCA ACA GAA     5718
Glu Ala Asn Arg Pro Gly Lys Val Pro Phe Leu Arg Val Ala Thr Glu
                1560                1565                1570

AGC TCT GCA AAG ACT CCC TCC AAG CTA TTG GAT CCT CTT GCT TGG GAT     5766
Ser Ser Ala Lys Thr Pro Ser Lys Leu Leu Asp Pro Leu Ala Trp Asp
            1575                1580                1585

AAC CAC TAT GGT ACT CAG ATA CCA AAA GAA GAG TGG AAA TCC CAA GAG     5814
Asn His Tyr Gly Thr Gln Ile Pro Lys Glu Glu Trp Lys Ser Gln Glu
        1590                1595                1600

AAG TCA CCA GAA AAA ACA GCT TTT AAG AAA AAG GAT ACC ATT TTG TCC     5862
Lys Ser Pro Glu Lys Thr Ala Phe Lys Lys Lys Asp Thr Ile Leu Ser
    1605                1610                1615

CTG AAC GCT TGT GAA AGC AAT CAT GCA ATA GCA GCA ATA AAT GAG GGA     5910
Leu Asn Ala Cys Glu Ser Asn His Ala Ile Ala Ala Ile Asn Glu Gly
1620                1625                1630                1635

CAA AAT AAG CCC GAA ATA GAA GTC ACC TGG GCA AAG CAA GGT AGG ACT     5958
Gln Asn Lys Pro Glu Ile Glu Val Thr Trp Ala Lys Gln Gly Arg Thr
                1640                1645                1650

GAA AGG CTG TGC TCT CAA AAC CCA CCA GTC TTG AAA CGC CAT CAA CGG     6006
Glu Arg Leu Cys Ser Gln Asn Pro Pro Val Leu Lys Arg His Gln Arg
            1655                1660                1665

GAA ATA ACT CGT ACT ACT CTT CAG TCA GAT CAA GAG GAA ATT GAC TAT     6054
Glu Ile Thr Arg Thr Thr Leu Gln Ser Asp Gln Glu Glu Ile Asp Tyr
        1670                1675                1680

GAT GAT ACC ATA TCA GTT GAA ATG AAG AAG GAA GAT TTT GAC ATT TAT     6102
Asp Asp Thr Ile Ser Val Glu Met Lys Lys Glu Asp Phe Asp Ile Tyr
    1685                1690                1695

GAT GAG GAT GAA AAT CAG AGC CCC CGC AGC TTT CAA AAG AAA ACA CGA     6150
Asp Glu Asp Glu Asn Gln Ser Pro Arg Ser Phe Gln Lys Lys Thr Arg
1700                1705                1710                1715

CAC TAT TTT ATT GCT GCA GTG GAG AGG CTC TGG GAT TAT GGG ATG AGT     6198
His Tyr Phe Ile Ala Ala Val Glu Arg Leu Trp Asp Tyr Gly Met Ser
                1720                1725                1730

AGC TCC CCA CAT GTT CTA AGA AAC AGG GCT CAG AGT GGC AGT GTC CCT     6246
Ser Ser Pro His Val Leu Arg Asn Arg Ala Gln Ser Gly Ser Val Pro
            1735                1740                1745

CAG TTC AAG AAA GTT GTT TTC CAG GAA TTT ACT GAT GGC TCC TTT ACT     6294
Gln Phe Lys Lys Val Val Phe Gln Glu Phe Thr Asp Gly Ser Phe Thr
        1750                1755                1760

CAG CCC TTA TAC CGT GGA GAA CTA AAT GAA CAT TTG GGA CTC CTG GGG     6342
Gln Pro Leu Tyr Arg Gly Glu Leu Asn Glu His Leu Gly Leu Leu Gly
    1765                1770                1775

CCA TAT ATA AGA GCA GAA GTT GAA GAT AAT ATC ATG GTA ACT TTC AGA     6390
Pro Tyr Ile Arg Ala Glu Val Glu Asp Asn Ile Met Val Thr Phe Arg
1780                1785                1790                1795
```

```
AAT CAG GCC TCT CGT CCC TAT TCC TTC TAT TCT AGC CTT ATT TCT TAT        6438
Asn Gln Ala Ser Arg Pro Tyr Ser Phe Tyr Ser Ser Leu Ile Ser Tyr
        1800                1805                1810

GAG GAA GAT CAG AGG CAA GGA GCA GAA CCT AGA AAA AAC TTT GTC AAG        6486
Glu Glu Asp Gln Arg Gln Gly Ala Glu Pro Arg Lys Asn Phe Val Lys
        1815                1820                1825

CCT AAT GAA ACC AAA ACT TAC TTT TGG AAA GTG CAA CAT CAT ATG GCA        6534
Pro Asn Glu Thr Lys Thr Tyr Phe Trp Lys Val Gln His His Met Ala
        1830                1835                1840

CCC ACT AAA GAT GAG TTT GAC TGC AAA GCC TGG GCT TAT TTC TCT GAT        6582
Pro Thr Lys Asp Glu Phe Asp Cys Lys Ala Trp Ala Tyr Phe Ser Asp
        1845                1850                1855

GTT GAC CTG GAA AAA GAT GTG CAC TCA GGC CTG ATT GGA CCC CTT CTG        6630
Val Asp Leu Glu Lys Asp Val His Ser Gly Leu Ile Gly Pro Leu Leu
1860                1865                1870                1875

GTC TGC CAC ACT AAC ACA CTG AAC CCT GCT CAT GGG AGA CAA GTG ACA        6678
Val Cys His Thr Asn Thr Leu Asn Pro Ala His Gly Arg Gln Val Thr
                1880                1885                1890

GTA CAG GAA TTT GCT CTG TTT TTC ACC ATC TTT GAT GAG ACC AAA AGC        6726
Val Gln Glu Phe Ala Leu Phe Phe Thr Ile Phe Asp Glu Thr Lys Ser
        1895                1900                1905

TGG TAC TTC ACT GAA AAT ATG GAA AGA AAC TGC AGG GCT CCC TGC AAT        6774
Trp Tyr Phe Thr Glu Asn Met Glu Arg Asn Cys Arg Ala Pro Cys Asn
        1910                1915                1920

ATC CAG ATG GAA GAT CCC ACT TTT AAA GAG AAT TAT CGC TTC CAT GCA        6822
Ile Gln Met Glu Asp Pro Thr Phe Lys Glu Asn Tyr Arg Phe His Ala
        1925                1930                1935

ATC AAT GGC TAC ATA ATG GAT ACA CTA CCT GGC TTA GTA ATG GCT CAG        6870
Ile Asn Gly Tyr Ile Met Asp Thr Leu Pro Gly Leu Val Met Ala Gln
1940                1945                1950                1955

GAT CAA AGG ATT CGA TGG TAT CTG CTC AGC ATG GGC AGC AAT GAA AAC        6918
Asp Gln Arg Ile Arg Trp Tyr Leu Leu Ser Met Gly Ser Asn Glu Asn
                1960                1965                1970

ATC CAT TCT ATT CAT TTC AGT GGA CAT GTG TTC ACT GTA CGA AAA AAA        6966
Ile His Ser Ile His Phe Ser Gly His Val Phe Thr Val Arg Lys Lys
        1975                1980                1985

GAG GAG TAT AAA ATG GCA CTG TAC AAT CTC TAT CCA GGT GTT TTT GAG        7014
Glu Glu Tyr Lys Met Ala Leu Tyr Asn Leu Tyr Pro Gly Val Phe Glu
        1990                1995                2000

ACA GTG GAA ATG TTA CCA TCC AAA GCT GGA ATT TGG CGG GTG GAA TGC        7062
Thr Val Glu Met Leu Pro Ser Lys Ala Gly Ile Trp Arg Val Glu Cys
        2005                2010                2015

CTT ATT GGC GAG CAT CTA CAT GCT GGG ATG AGC ACA CTT TTT CTG GTG        7110
Leu Ile Gly Glu His Leu His Ala Gly Met Ser Thr Leu Phe Leu Val
2020                2025                2030                2035

TAC AGC AAT AAG TGT CAG ACT CCC CTG GGA ATG GCT TCT GGA CAC ATT        7158
Tyr Ser Asn Lys Cys Gln Thr Pro Leu Gly Met Ala Ser Gly His Ile
                2040                2045                2050

AGA GAT TTT CAG ATT ACA GCT TCA GGA CAA TAT GGA CAG TGG GCC CCA        7206
Arg Asp Phe Gln Ile Thr Ala Ser Gly Gln Tyr Gly Gln Trp Ala Pro
        2055                2060                2065

AAG CTG GCC AGA CTT CAT TAT TCC GGA TCA ATC AAT GCC TGG AGC ACC        7254
Lys Leu Ala Arg Leu His Tyr Ser Gly Ser Ile Asn Ala Trp Ser Thr
        2070                2075                2080

AAG GAG CCC TTT TCT TGG ATC AAG GTG GAT CTG TTG GCA CCA ATG ATT        7302
Lys Glu Pro Phe Ser Trp Ile Lys Val Asp Leu Leu Ala Pro Met Ile
        2085                2090                2095

ATT CAC GGC ATC AAG ACC CAG GGT GCC CGT CAG AAG TTC TCC AGC CTC        7350
Ile His Gly Ile Lys Thr Gln Gly Ala Arg Gln Lys Phe Ser Ser Leu
2100                2105                2110                2115
```

-continued

| | | |
|---|---|---|
| TAC ATC TCT CAG TTT ATC ATC ATG TAT AGT CTT GAT GGG AAG AAG TGG<br>Tyr Ile Ser Gln Phe Ile Ile Met Tyr Ser Leu Asp Gly Lys Lys Trp<br>       2120        2125       2130 | 7398 |
| CAG ACT TAT CGA GGA AAT TCC ACT GGA ACC TTA ATG GTC TTC TTT GGC<br>Gln Thr Tyr Arg Gly Asn Ser Thr Gly Thr Leu Met Val Phe Phe Gly<br>       2135        2140        2145 | 7446 |
| AAT GTG GAT TCA TCT GGG ATA AAA CAC AAT ATT TTT AAC CCT CCA ATT<br>Asn Val Asp Ser Ser Gly Ile Lys His Asn Ile Phe Asn Pro Pro Ile<br>       2150        2155        2160 | 7494 |
| ATT GCT CGA TAC ATC CGT TTG CAC CCA ACT CAT TAT AGC ATT CGC AGC<br>Ile Ala Arg Tyr Ile Arg Leu His Pro Thr His Tyr Ser Ile Arg Ser<br>       2165        2170        2175 | 7542 |
| ACT CTT CGC ATG GAG TTG ATG GGC TGT GAT TTA AAT AGT TGC AGC ATG<br>Thr Leu Arg Met Glu Leu Met Gly Cys Asp Leu Asn Ser Cys Ser Met<br>2180        2185        2190        2195 | 7590 |
| CCA TTG GGA ATG GAG AGT AAA GCA ATA TCA GAT GCA CAG ATT ACT GCT<br>Pro Leu Gly Met Glu Ser Lys Ala Ile Ser Asp Ala Gln Ile Thr Ala<br>       2200        2205        2210 | 7638 |
| TCA TCC TAC TTT ACC AAT ATG TTT GCC ACC TGG TCT CCT TCA AAA GCT<br>Ser Ser Tyr Phe Thr Asn Met Phe Ala Thr Trp Ser Pro Ser Lys Ala<br>       2215        2220        2225 | 7686 |
| CGA CTT CAC CTC CAA GGG AGG AGT AAT GCC TGG AGA CCT CAG GTG AAT<br>Arg Leu His Leu Gln Gly Arg Ser Asn Ala Trp Arg Pro Gln Val Asn<br>       2230        2235        2240 | 7734 |
| AAT CCA AAA GAG TGG CTG CAA GTG GAC TTC CAG AAG ACA ATG AAA GTC<br>Asn Pro Lys Glu Trp Leu Gln Val Asp Phe Gln Lys Thr Met Lys Val<br>       2245        2250        2255 | 7782 |
| ACA GGA GTA ACT ACT CAG GGA GTA AAA TCT CTG CTT ACC AGC ATG TAT<br>Thr Gly Val Thr Thr Gln Gly Val Lys Ser Leu Leu Thr Ser Met Tyr<br>2260        2265        2270        2275 | 7830 |
| GTG AAG GAG TTC CTC ATC TCC AGC AGT CAA GAT GGC CAT CAG TGG ACT<br>Val Lys Glu Phe Leu Ile Ser Ser Ser Gln Asp Gly His Gln Trp Thr<br>       2280        2285        2290 | 7878 |
| CTC TTT TTT CAG AAT GGC AAA GTA AAG GTT TTT CAG GGA AAT CAA GAC<br>Leu Phe Phe Gln Asn Gly Lys Val Lys Val Phe Gln Gly Asn Gln Asp<br>       2295        2300        2305 | 7926 |
| TCC TTC ACA CCT GTG GTG AAC TCT CTA GAC CCA CCG TTA CTG ACT CGC<br>Ser Phe Thr Pro Val Val Asn Ser Leu Asp Pro Pro Leu Leu Thr Arg<br>       2310        2315        2320 | 7974 |
| TAC CTT CGA ATT CAC CCC CAG AGT TGG GTG CAC CAG ATT GCC CTG AGG<br>Tyr Leu Arg Ile His Pro Gln Ser Trp Val His Gln Ile Ala Leu Arg<br>       2325        2330        2335 | 8022 |
| ATG GAG GTT CTG GGC TGC GAG GCA CAG GAC CTC TAC TGAGGGTGGC<br>Met Glu Val Leu Gly Cys Glu Ala Gln Asp Leu Tyr<br>2340        2345        2350 | 8068 |
| CACTGCAGCA CCTGCCACTG CCGTCACCTC TCCCTCCTCA GCTCCAGGGC AGTGTCCCTC | 8128 |
| CCTGGCTTGC CTTCTACCTT TGTGCTAAAT CCTAGCAGAC ACTGCCTTGA AGCCTCCTGA | 8188 |
| ATTAACTATC ATCAGTCCTG CATTTCTTTG GTGGGGGGCC AGGAGGGTGC ATCCAATTTA | 8248 |
| ACTTAACTCT TACCTATTTT CTGCAGCTGC TCCCAGATTA CTCCTTCCTT CCAATATAAC | 8308 |
| TAGGCAAAAA GAAGTGAGGA GAAACCTGCA TGAAAGCATT CTTCCCTGAA AAGTTAGGCC | 8368 |
| TCTCAGAGTC ACCACTTCCT CTGTTGTAGA AAAACTATGT GATGAAACTT TGAAAAAGAT | 8428 |
| ATTTATGATG TTAACTTGTT TATTGCAGCT TATAATGGTT ACAAATAAAG CAATAGCATC | 8488 |
| ACAAATTTCA CAAATAAAGC ATTTTTTTCA CTGCATTCTA GTTGTGGTTT GTCCAAACTC | 8548 |
| ATCAATGTAT CTTATCATGT CTGGATCCCC GGGTGGCATC CCTGTGACCC CTCCCCAGTG | 8608 |

-continued

| | |
|---|---|
| CCTCTCCTGG CCCTGGAAGT TGCCACTCCA GTGCCCACCA GCCTTGTCCT AATAAAATTA | 8668 |
| AGTTGCATCA TTTTGTCTGA CTAGGTGTCC TTCTATAATA TTATGGGGTG GAGGGGGGTG | 8728 |
| GTATGGAGCA AGGGGCAAGT TGGGAAGACA ACCTGTAGGG CCTGCGGGGT CTATTCGGGA | 8788 |
| ACCAAGCTGG AGTGCAGTGG CACAATCTTG GCTCACTGCA ATCTCCGCCT CCTGGGTTCA | 8848 |
| AGCGATTCTC CTGCCTCAGC CTCCCGAGTT GTTGGGATTC CAGGCATGCA TGACCAGGCT | 8908 |
| CAGCTAATTT TTGTTTTTTT GGTAGAGACG GGGTTTCACC ATATTGGCCA GGCTGGTCTC | 8968 |
| CAACTCCTAA TCTCAGGTGA TCTACCCACC TTGGCCTCCC AAATTGCTGG GATTACAGGC | 9028 |
| GTGAACCACT GCTCCCTTCC CTGTCCTTCT GATTTTAAAA TAACTATACC AGCAGGAGGA | 9088 |
| CGTCCAGACA CAGCATAGGC TACCTGCCAT GCCCAACCGG TGGGACATTT GAGTTGCTTG | 9148 |
| CTTGGCACTG TCCTCTCATG CGTTGGGTCC ACTCAGTAGA TGCCTGTTGA ATTCGTAATC | 9208 |
| ATGGTCATAG CTGTTTCCTG TGTGAAATTG TTATCCGCTC ACAATTCCAC ACAACATACG | 9268 |
| AGCCGGAAGC ATAAAGTGTA AAGCCTGGGG TGCCTAATGA GTGAGCTAAC TCACATTAAT | 9328 |
| TGCGTTGCGC TCACTGCCCG CTTTCCAGTC GGGAAACCTG TCGTGCCAGC TGCATTAATG | 9388 |
| AATCGGCCAA CGCGCGGGGA GAGGCGGTTT GCGTATTGGG CGCTCTTCCG CTTCCTCGCT | 9448 |
| CACTGACTCG CTGCGCTCGG TCGTTCGGCT GCGGCGAGCG GTATCAGCTC ACTCAAAGGC | 9508 |
| GGTAATACGG TTATCCACAG AATCAGGGGA TAACGCAGGA AAGAACATGT GAGCAAAAGG | 9568 |
| CCAGCAAAAG GCCAGGAACC GTAAAAAGGC CGCGTTGCTG GCGTTTTTCC ATAGGCTCCG | 9628 |
| CCCCCCTGAC GAGCATCACA AAAATCGACG CTCAAGTCAG AGGTGGCGAA ACCCGACAGG | 9688 |
| ACTATAAAGA TACCAGGCGT TTCCCCCTGG AAGCTCCCTC GTGCGCTCTC CTGTTCCGAC | 9748 |
| CCTGCCGCTT ACCGGATACC TGTCCGCCTT TCTCCCTTCG GGAAGCGTGG CGCTTTCTCA | 9808 |
| TAGCTCACGC TGTAGGTATC TCAGTTCGGT GTAGGTCGTT CGCTCCAAGC TGGGCTGTGT | 9868 |
| GCACGAACCC CCCGTTCAGC CCGACCGCTG CGCCTTATCC GGTAACTATC GTCTTGAGTC | 9928 |
| CAACCCGGTA AGACACGACT TATCGCCACT GGCAGCAGCC ACTGGTAACA GGATTAGCAG | 9988 |
| AGCGAGGTAT GTAGGCGGTG CTACAGAGTT CTTGAAGTGG TGGCCTAACT ACGGCTACAC | 10048 |
| TAGAAGGACA GTATTTGGTA TCTGCGCTCT GCTGAAGCCA GTTACCTTCG GAAAAGAGT | 10108 |
| TGGTAGCTCT TGATCCGGCA AACAAACCAC CGCTGGTAGC GGTGGTTTTT TTGTTTGCAA | 10168 |
| GCAGCAGATT ACGCGCAGAA AAAAAGGATC TCAAGAAGAT CCTTTGATCT TTTCTACGGG | 10228 |
| GTCTGACGCT CAGTGGAACG AAAACTCACG TTAAGGGATT TTGGTCATGA GATTATCAAA | 10288 |
| AAGGATCTTC ACCTAGATCC TTTTAAATTA AAAATGAAGT TTTAAATCAA TCTAAAGTAT | 10348 |
| ATATGAGTAA ACTTGGTCTG ACAGTTACCA ATGCTTAATC AGTGAGGCAC CTATCTCAGC | 10408 |
| GATCTGTCTA TTTCGTTCAT CCATAGTTGC CTGACTCCCC GTCGTGTAGA TAACTACGAT | 10468 |
| ACGGGAGGGC TTACCATCTG GCCCCAGTGC TGCAATGATA CCGCGAGACC CACGCTCACC | 10528 |
| GGCTCCAGAT TTATCAGCAA TAAACCAGCC AGCCGGAAGG GCCGAGCGCA GAAGTGGTCC | 10588 |
| TGCAACTTTA TCCGCCTCCA TCCAGTCTAT TAATTGTTGC CGGGAAGCTA GAGTAAGTAG | 10648 |
| TTCGCCAGTT AATAGTTTGC GCAACGTTGT TGCCATTGCT ACAGGCATCG TGGTGTCACG | 10708 |
| CTCGTCGTTT GGTATGGCTT CATTCAGCTC CGGTTCCCAA CGATCAAGGC GAGTTACATG | 10768 |
| ATCCCCCATG TTGTGCAAAA AAGCGGTTAG CTCCTTCGGT CCTCCGATCG TTGTCAGAAG | 10828 |
| TAAGTTGGCC GCAGTGTTAT CACTCATGGT TATGGCAGCA CTGCATAATT CTCTTACTGT | 10888 |
| CATGCCATCC GTAAGATGCT TTTCTGTGAC TGGTGAGTAC TCAACCAAGT CATTCTGAGA | 10948 |
| ATAGTGTATG CGGCGACCGA GTTGCTCTTG CCCGGCGTCA ATACGGGATA ATACCGCGCC | 11008 |

```
ACATAGCAGA ACTTTAAAAG TGCTCATCAT TGGAAAACGT TCTTCGGGGC GAAAACTCTC      11068

AAGGATCTTA CCGCTGTTGA GATCCAGTTC GATGTAACCC ACTCGTGCAC CCAACTGATC      11128

TTCAGCATCT TTTACTTTCA CCAGCGTTTC TGGGTGAGCA AAAACAGGAA GGCAAAATGC      11188

CGCAAAAAAG GGAATAAGGG CGACACGGAA ATGTTGAATA CTCATACTCT TCCTTTTTCA      11248

ATATTATTGA AGCATTTATC AGGGTTATTG TCTCATGAGC GGATACATAT TTGAATGTAT      11308

TTAGAAAAAT AAACAAATAG GGGTTCCGCG CACATTTCCC CGAAAAGTGC CACCTGACGT      11368

CTAAGAAACC ATTATTATCA TGACATTAAC CTATAAAAAT AGGCGTATCA CGAGGCCCTT      11428

TCGTCTCGCG CGTTTCGGTG ATGACGGTGA AAACCTCTGA CACATGCAGC TCCCGGAGAC      11488

GGTCACAGCT TGTCTGTAAG CGGATGCCGG GAGCAGACAA GCCCGTCAGG GCGCGTCAGC      11548

GGGTGTTGGC GGGTGTCGGG GCTGGCTTAA CTATGCGGCA TCAGAGCAGA TTGTACTGAG      11608

AGTGCACCAT ATGCGGTGTG AAATACCGCA CAGATGCGTA AGGAGAAAAT ACCGCATCAG      11668

GCGCCATTCG CCATTCAGGC TGCGCAACTG TTGGGAAGGG CGATCGGTGC GGGCCTCTTC      11728

GCTATTACGC CAGCTGGCGA AAGGGGGATG TGCTGCAAGG CGATTAAGTT GGGTAACGCC      11788

AGGGTTTTCC CAGTCACGAC GTTGTAAAAC GACGGCCAGT GCCAAGCTTG GCTGCAG        11846

(2) INFORMATION FOR SEQ ID NO:5:

(i) SEQUENCE CHARACTERISTICS:
        (A) LENGTH: 211 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

ATTGAACCAA GAAGCTTCTC CCAGGTAAGT TGCTAATAAA GCTTGGCAAG AGTATTTCAA        60

GGAAGATGAA GTCATTAACT ATGCAAAATG CTTCTCAGGC ACCTAGGAAA ATGAGGATGT       120

GAGGCATTTC TACCCACTTG GTACATAAAA TTATTGCTTT TCCTCTTCTT TTTTTCTCCA       180

GAACCCACCA GTCTTGAAAC GCCATCAACG G                                      211

(2) INFORMATION FOR SEQ ID NO:6:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GTTGGTATCC TTTTTACAGC ACAACTTAAT GAGACAGATA GAAACTGGTC TTGTAGAAAC        60

AGAGTAGTCG CCTGCTTTTC TGCCAGGTGC TGACTTCTCT CCCCTGGGCT GTTTTCATTT       120

TCTCAG                                                                  126

(2) INFORMATION FOR SEQ ID NO:7:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO:7:

```
GTAAGTATCC TTTTTACAGC ACAACTTAAT GAGACAGATA GAAACTGGTC TTGTAGAAAC      60

AGAGTAGTCG CCTGCTTTTC TGCCAGGTGC TGACTTCTCT CCCCTTCTCT TTTTTCCTTT     120

TCTCAG                                                                126
```

(2) INFORMATION FOR SEQ ID NO:8:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
GCCACCAUGG                                                             10
```

(2) INFORMATION FOR SEQ ID NO:9:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
AGGTTAATTT TTAAAAAGCA GTCAAAAGTC CAAGTGGCCC TTGCGAGCAT TTACTCTCTC      60

TGTTTGCTCT GGTTAATAAT CTCAGGAGCA CAAACATTCC                           100
```

(2) INFORMATION FOR SEQ ID NO:10:

(i) SEQUENCE CHARACTERISTICS:
        (A) LENGTH: 223 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
CTTTCTCTTT TCTTTTACAT GAAGGGTCTG GCAGCCAAAG CAATCACTCA AAGTTCAAAC      60

CTTATCATTT TTTGCTTTGT TCCTCTTGGC CTTGGTTTTG TACATCAGCT TTGAAAATAC     120

CATCCCAGGG TTAATGCTGG GGTTAATTTA TAACTAAGAG TGCTCTAGTT TTGCAATACA     180

GGACATGCTA TAAAAATGGA AAGATGTTGC TTTCTGAGAG ATA                      223
```

(2) INFORMATION FOR SEQ ID NO:11:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
AGAUCUCGAG AAAGCUAACA ACAAAGAACA ACAAACAACA AUCAGGAUAA CAAGAACGAA      60

ACAAUAACAG CCACCAUGGA AAUAGAGCUC                                       90
```